US012673985B2

(12) United States Patent
Stephens et al.

(10) Patent No.: US 12,673,985 B2
(45) Date of Patent: Jul. 7, 2026

(54) METHOD FOR THE TREATMENT OR PROPHYLAXIS OF CANCER BY TARGETING THE EXTRACELLULAR PORTION OF KERATIN 14 (KRT14) RESIDING ON CANCER CELLS

(71) Applicant: Hudson Institute of Medical Research, Clayton (AU)

(72) Inventors: Andrew Nicholas Stephens, Knoxfield (AU); Maree Bilandzic, Endeavour Hills (AU)

(73) Assignee: Hudson Institute of Medical Research, Clayton (AU)

( * ) Notice: Subject to any disclaimer, the term of this patent is extended or adjusted under 35 U.S.C. 154(b) by 1301 days.

(21) Appl. No.: 17/429,093

(22) PCT Filed: Feb. 7, 2020

(86) PCT No.: PCT/AU2020/050106
§ 371 (c)(1),
(2) Date: Aug. 6, 2021

(87) PCT Pub. No.: WO2020/160628
PCT Pub. Date: Aug. 13, 2020

(65) Prior Publication Data
US 2022/0127341 A1 Apr. 28, 2022

(30) Foreign Application Priority Data
Feb. 7, 2019 (AU) ................................. 2019900382

(51) Int. Cl.
| | |
|---|---|
| C07K 14/47 | (2006.01) |
| A61K 33/243 | (2019.01) |
| A61K 39/00 | (2006.01) |
| A61K 39/395 | (2006.01) |
| A61K 45/06 | (2006.01) |
| A61K 47/68 | (2017.01) |
| A61P 35/00 | (2006.01) |
| C07K 16/18 | (2006.01) |
| C07K 16/30 | (2006.01) |
| G01N 33/575 | (2026.01) |
| G01N 33/57545 | (2026.01) |

(52) U.S. Cl.
CPC ............ *C07K 16/18* (2013.01); *A61K 33/243* (2019.01); *A61K 39/0011* (2013.01); *A61K 39/3955* (2013.01); *A61K 39/39558* (2013.01); *A61K 45/06* (2013.01); *A61K 47/6843* (2017.08); *A61P 35/00* (2018.01); *C07K 14/4741* (2013.01); *G01N 33/57545* (2026.01); *G01N 33/57575* (2026.01); *G01N 33/57585* (2026.01); *A61K 2039/505* (2013.01); *C07K 2317/33* (2013.01); *C07K 2317/34* (2013.01); *C07K 2317/565* (2013.01); *C07K 2317/567* (2013.01); *C07K 2317/76* (2013.01); *C07K*
*2319/40* (2013.01); *C07K 2319/60* (2013.01); *C07K 2319/61* (2013.01); *G01N 2333/4742* (2013.01)

(58) Field of Classification Search
CPC ........ C07K 16/18; C07K 16/44; C07K 16/30; C07K 2317/73; C07K 2317/56; C07K 2317/565; C07K 2319/40; C07K 2319/60; C07K 2319/61; C07K 2317/76; C07K 2317/34; A61K 39/395; A61K 39/0011; A61K 39/3955; A61K 39/39558
See application file for complete search history.

(56) References Cited

U.S. PATENT DOCUMENTS

2014/0336282 A1 11/2014 Ewald et al.

FOREIGN PATENT DOCUMENTS

WO 2011/017126 A1 2/2011

OTHER PUBLICATIONS

Chu et al. Keratin expression in human tissues and neoplasms. Histopathol 40: 403-439, 2002.*
Edwards et al. The remarkable flexibility of the human antibody repertoire; isolation of over one thousand different antibodies to a single protein, BLyS. J Mol Biol 334: 103-118, 2003.*
Iwasaki et al. Immunohistochemical detection of the expression of keratin 14 in the lingual epithelium of rats during the morphogenesis of filiform papillae. Arch Oral Biol 48: 605-613, 2003.*
Lipman et al. Monoclonal Versus Polyclonal Antibodies: Distinguishing Characteristics, Applications, and Information Resources. ILAR J 46(3): 258-268, 2005.*
Lloyd et al. Modelling the human immune response: performance of a 10/\11 human antibody repertoire against a broad panel of therapeutically relevant antigens. Protein Eng Design Selection 22(3): 159-168, 2009.*
Purkis et al. Antibody markers of basal cells in complex epithelia. J Cell Sci 97: 39-50, 1990.*

(Continued)

*Primary Examiner* — Bridget E Bunner
(74) *Attorney, Agent, or Firm* — McCarter & English, LLP; Marcie B. Clarke

(57) ABSTRACT

Disclosed herein are methods, uses and compositions for the treatment or prophylaxis of cancer in a mammalian subject comprising administering to the subject an amount of an agent which targets an extracellular portion of KRT14 or its functional homolog or variant thereof resident on cancer cells or an agent which induces production of an antagonist of the extracellular portion of KRT14 or its functional homolog or variant on cancer cells. The present disclosure also extends to methods of monitoring and/or diagnosing cancer in a subject.

15 Claims, 40 Drawing Sheets
Specification includes a Sequence Listing.

(56)            References Cited

OTHER PUBLICATIONS

Santeusanio et al. Antibodies to cytokeratin 14 specifically identify oncocytes (Hurthle cells) in thyroid lesions and tumors. App Immunohistochem 5(4): 223-228, 1997.*

Smedts et al. Keratin Expression in Cervical Cancer. Am J Pathol 141(2): 497-511, 1992.*

Stausbol-Gron et al. De novo identification of cell-type specific antibody-antigen pairs by phage display subtraction. Isolation of a human single chain antibody fragment against human keratin 14. Eur J Biochem 268: 3099-3107, 2001.*

Wetzels et al. Detection of Basement Membrane Components and Basal Cell Keratin 14 in Noninvasive and Invasive Carcinomas of the Breast. Am J Pathol 134(3): 571-579, 1989.*

Wetzels et al. Basal Cell-specific and Hyperproliferation-related Keratins in Human Breast Cancer. Am J Pathol 138(3): 751-763, 1991.*

White et al. Cancer Prevention for the next generation. J Adolesc Health 52: S1-S7, 2013.*

Cheung et al., Polyclonal breast cancer metastases arise from collective dissemination of keratin 14-expressing tumor cell clusters. Proc Natl Acad Sci U S A. Feb. 16, 2016;113(7):E854-63.

Wang et al., KRT14 promoting invasion and migration of lung cancer cells through ROCK-1 signaling pathway. Int J Clin Exp Pathol. 2017;10(1):795-803.

International Search Report and Written Opinion for Application No. PCT/AU2020/050106, dated Apr. 16, 2020, 11 pages.

International Preliminary Report on Patentability for Application No. PCT/AU2020/050106, dated Aug. 19, 2021, 8 pages.

* cited by examiner

A

18 hour Invasion Time Point

B

Alamar Blue cell viability

Figure 7

AN3CA – Endometrial carcinoma sw620 – Colorectal Carcinoma

Control mAb AN-17

FIGURE 16A
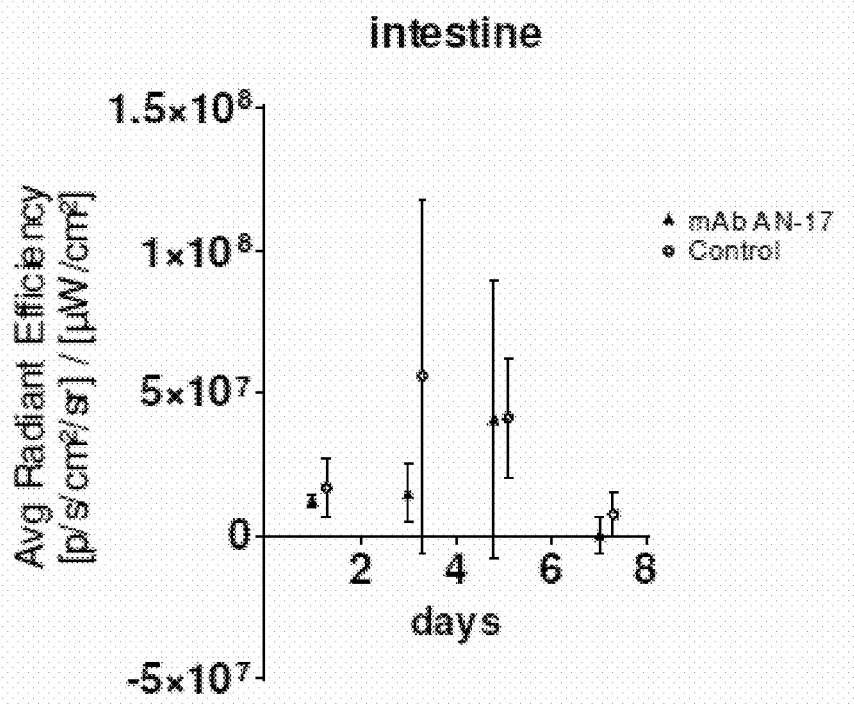
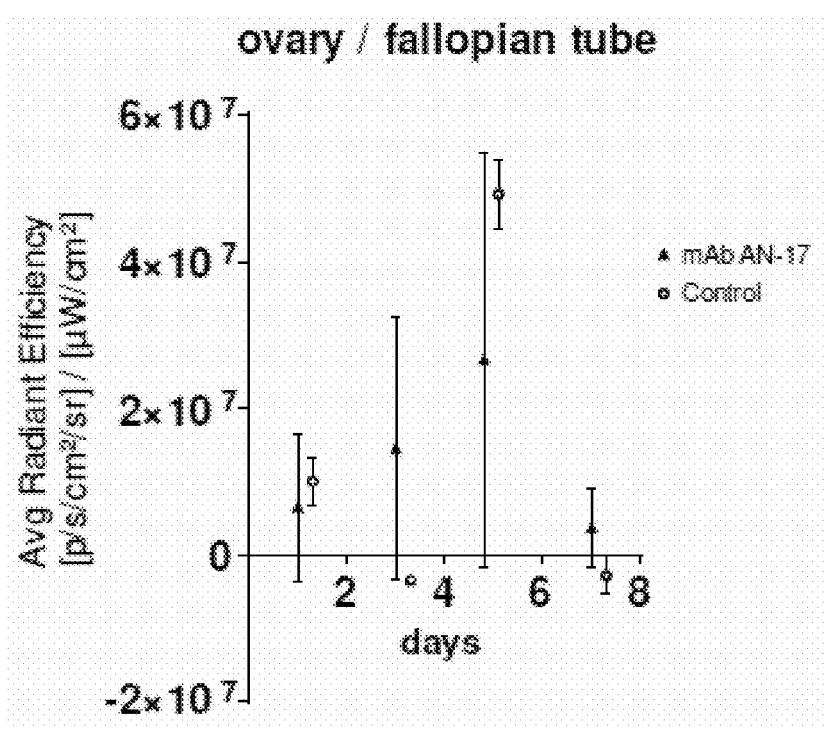

FIGURE 16B
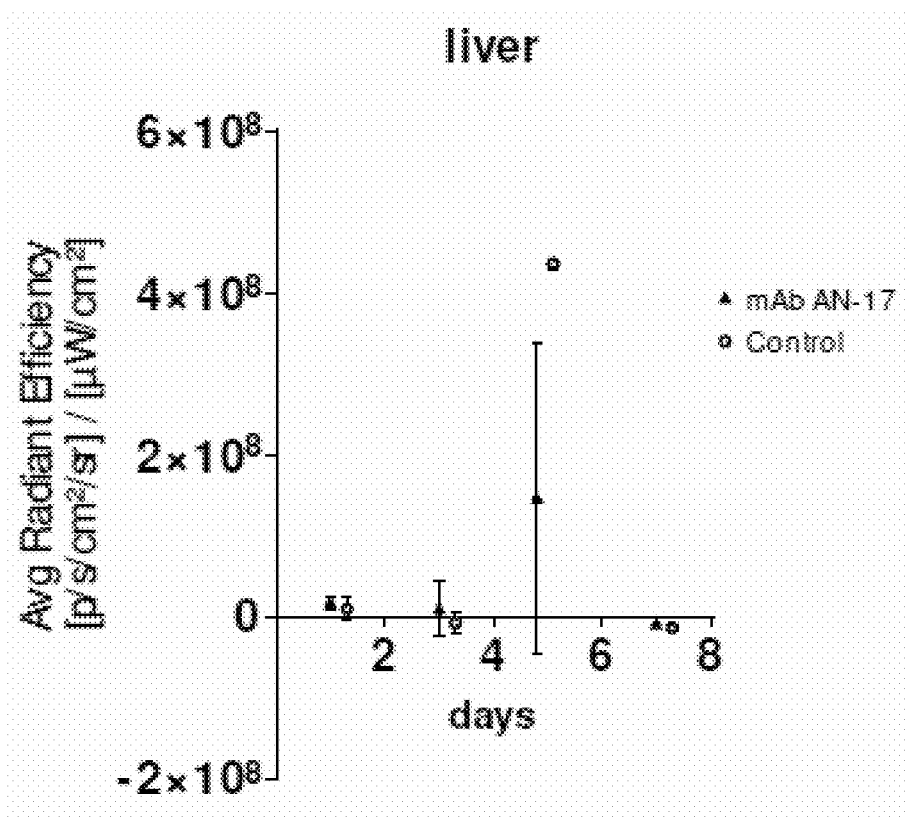
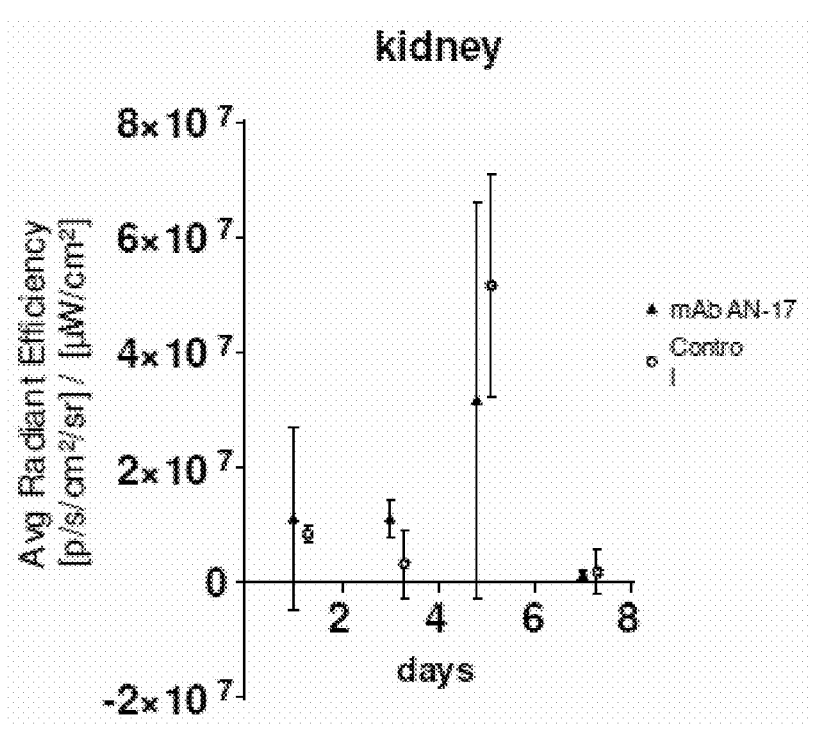

FIGURE 16C
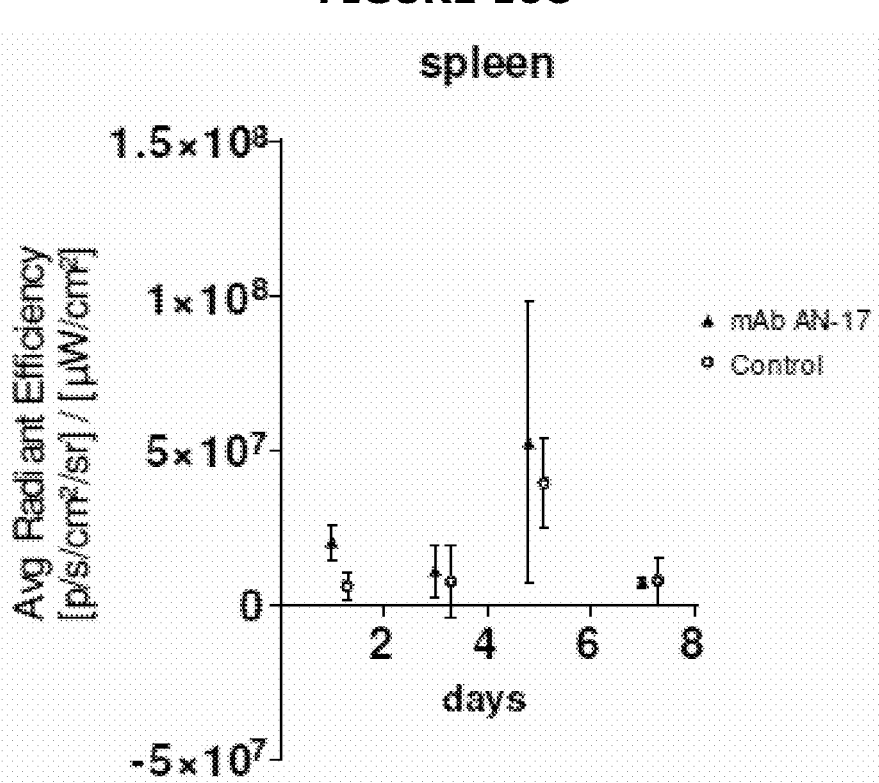
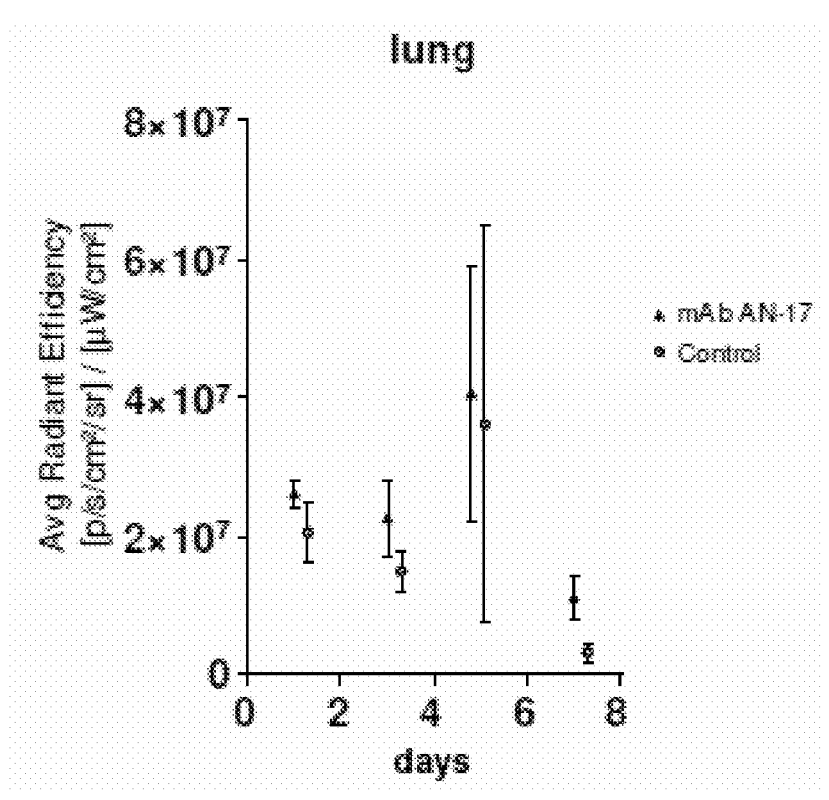

FIGURE 16D
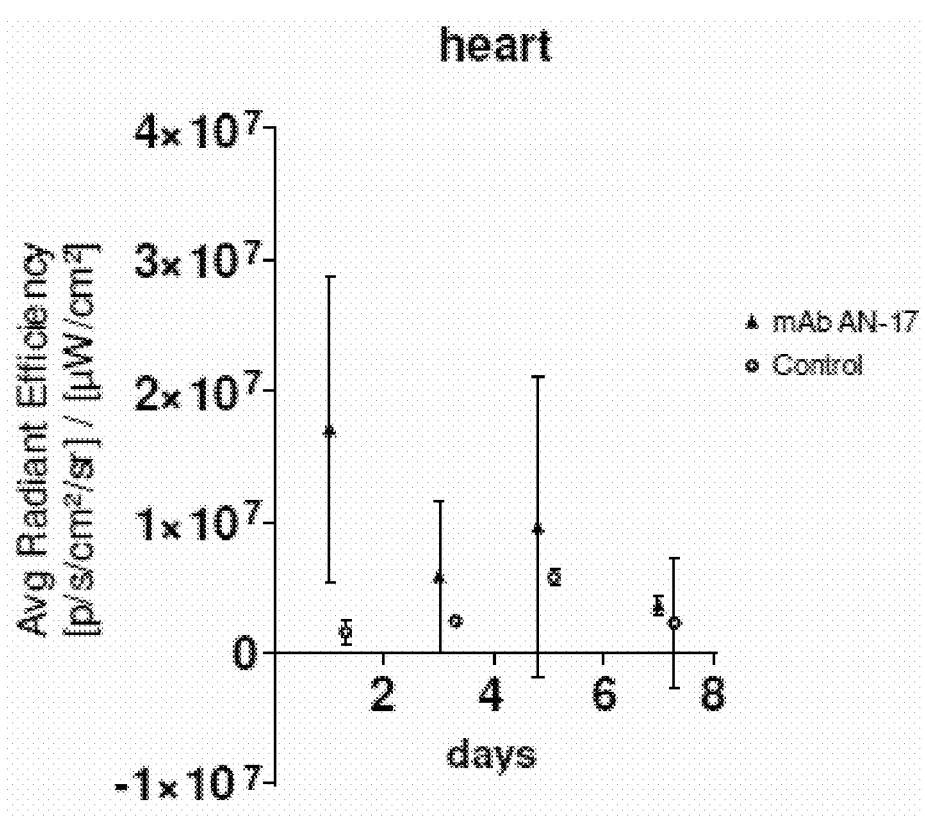
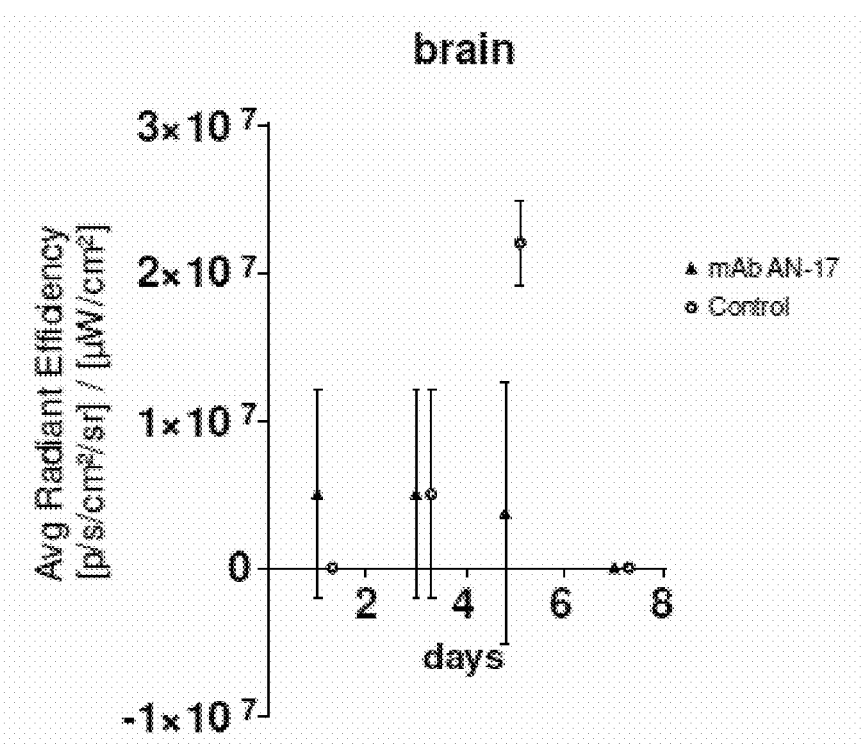

FIGURE 17A
Antibody retention after 7 days
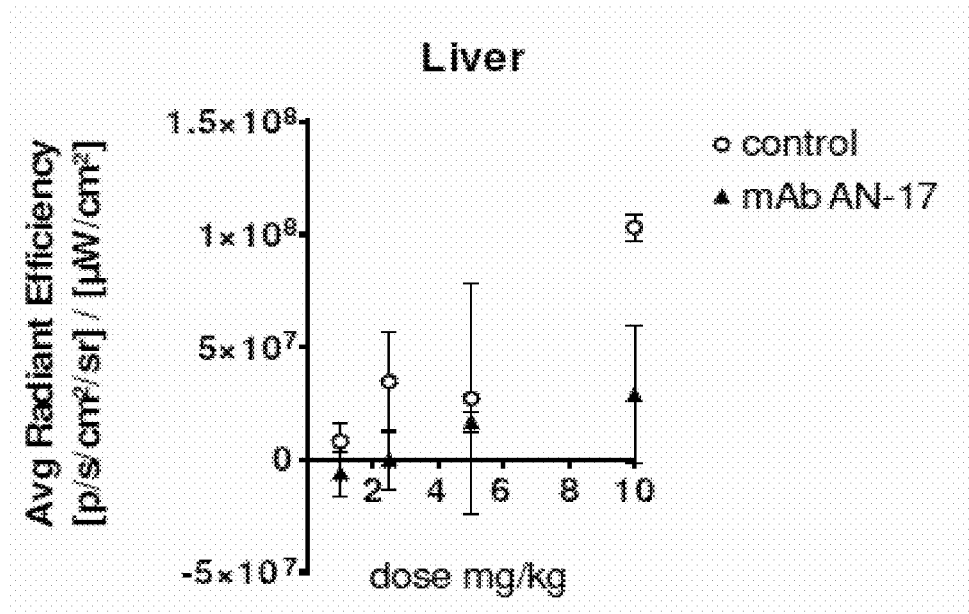
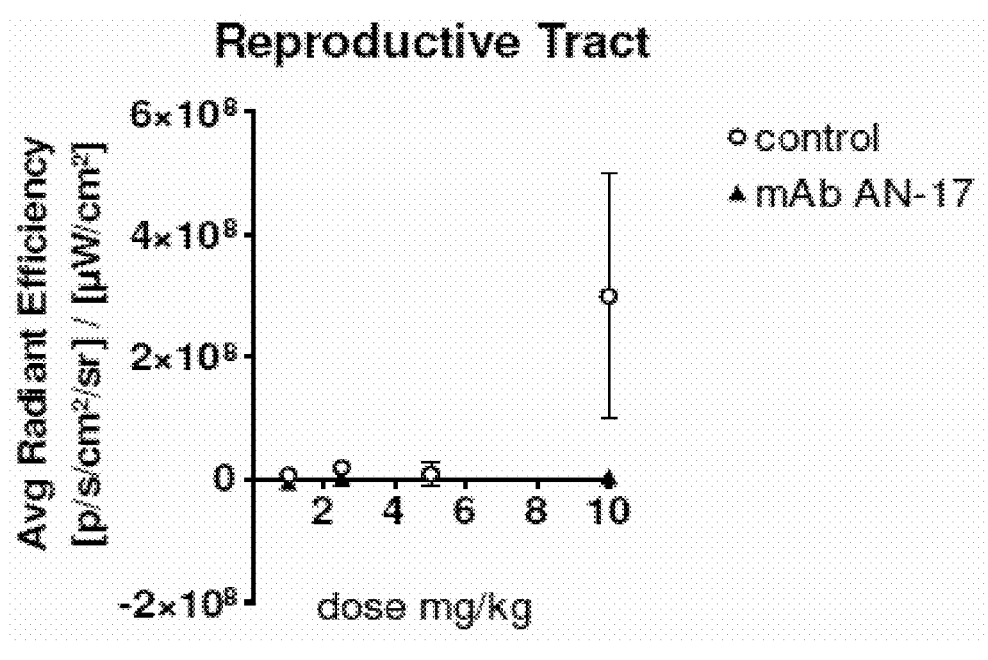

FIGURE 17B
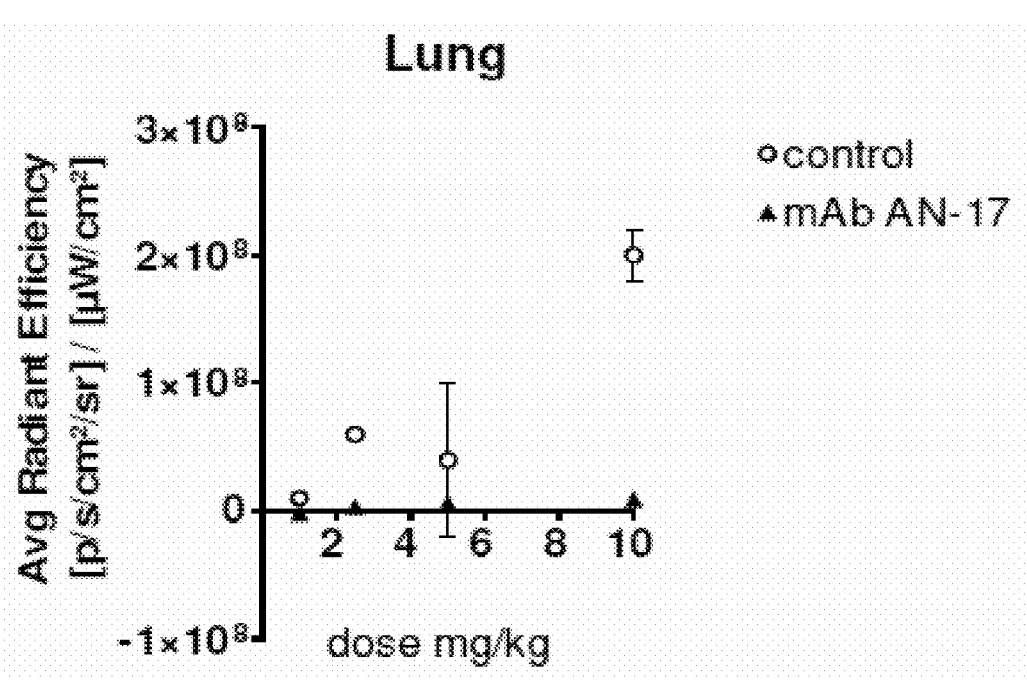
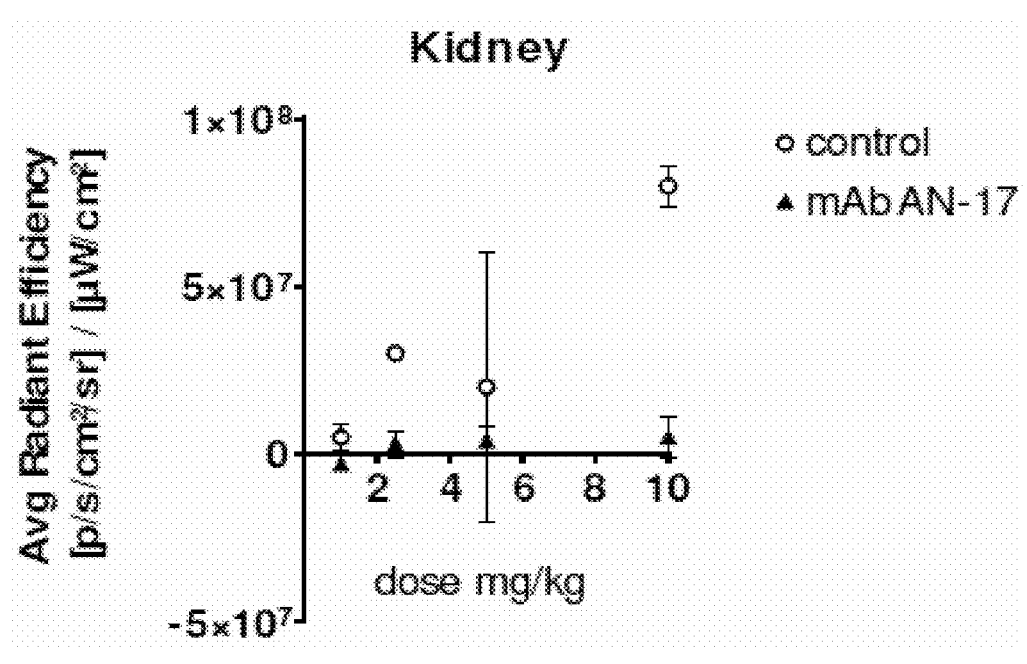

FIGURE 17C
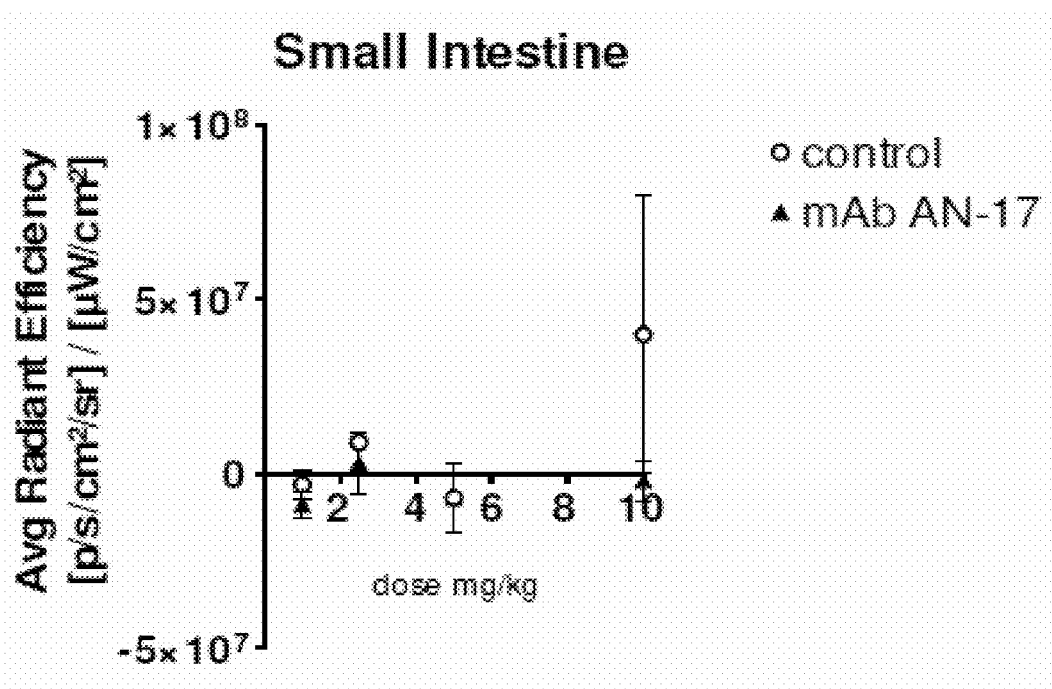
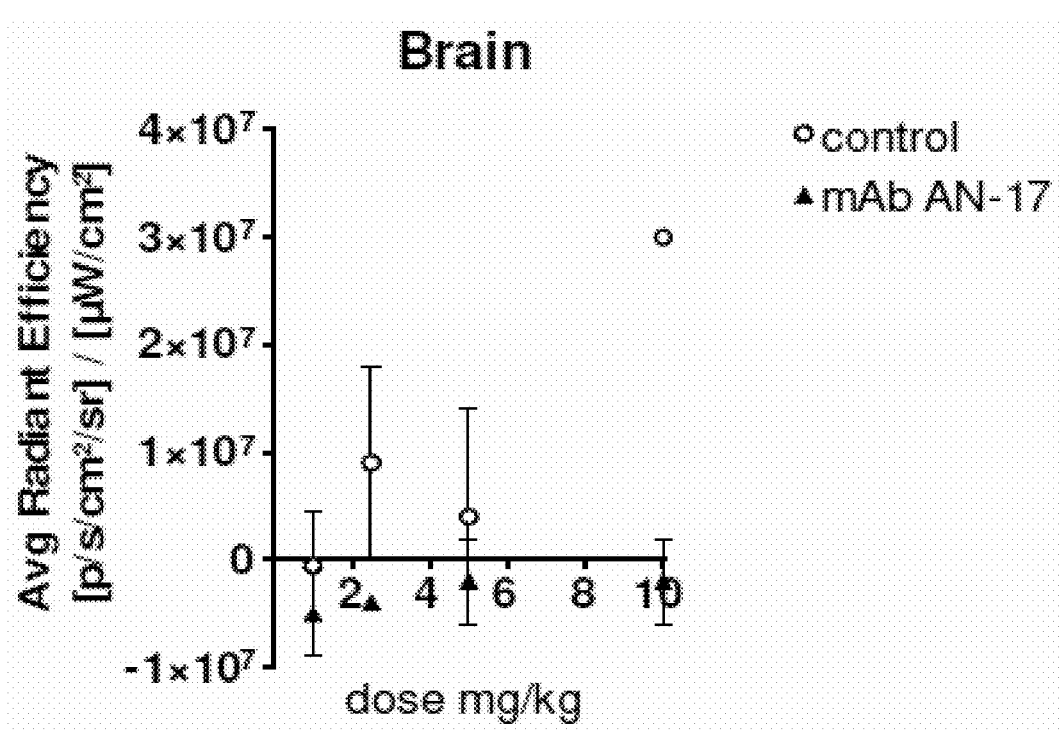

FIGURE 17D
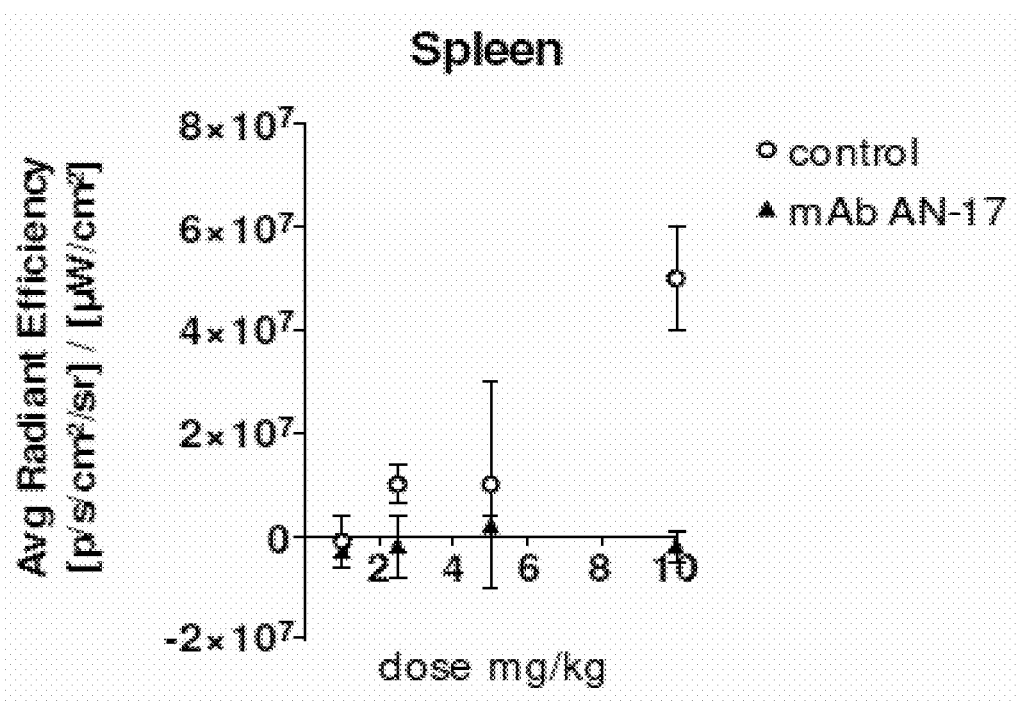
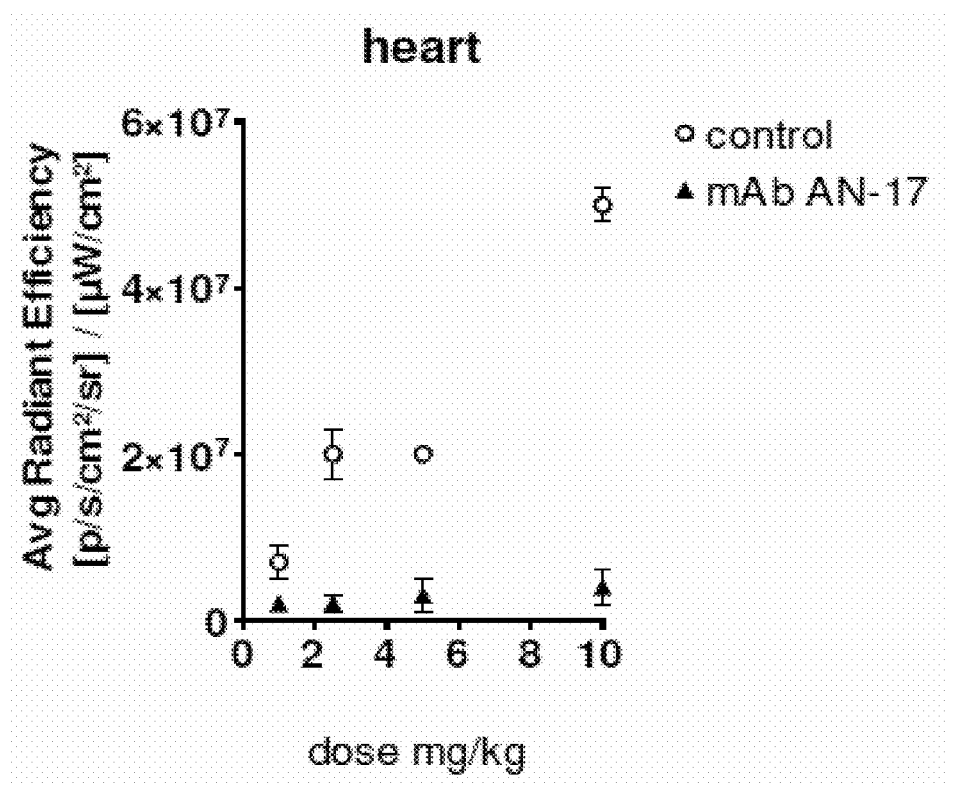

Figure 20:
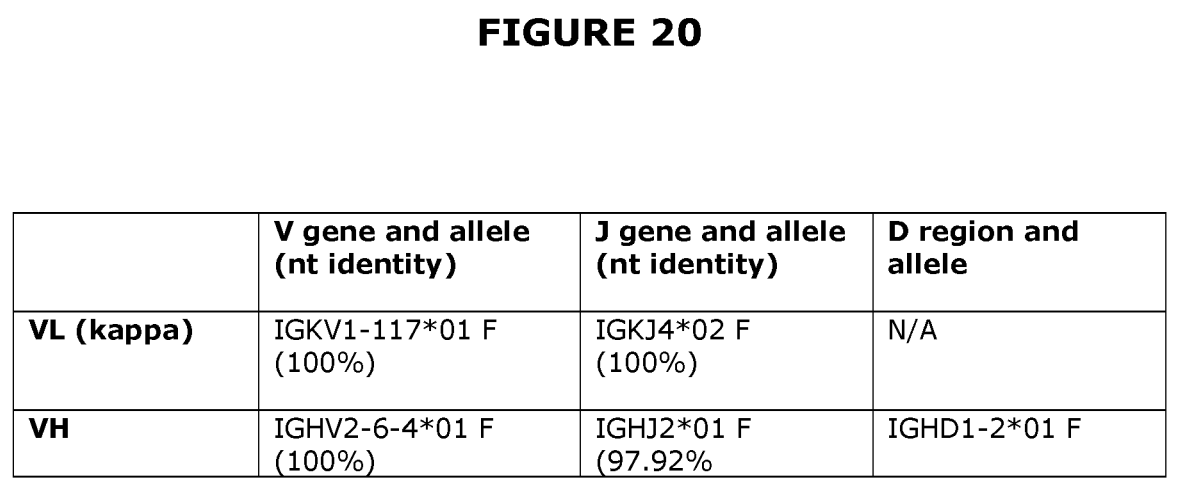

|  | V gene and allele (nt identity) | J gene and allele (nt identity) | D region and allele |
|---|---|---|---|
| VL (kappa) | IGKV1-117*01 F (100%) | IGKJ4*02 F (100%) | N/A |
| VH | IGHV2-6-4*01 F (100%) | IGHJ2*01 F (97.92% | IGHD1-2*01 F |

FIGURE 21

*Heavy-chain variable region (VH)*
*Nucleotide sequence*
CAGGTGCAGCTGAAGGAGTCAGGACCTGGCCTGGTGGCACCCTCACAGAGCC
TGTCCATCACATGCACTGTCTCTGGGTTCTCATTATCCAGATATAGTGTACACT
GGGTTCGCCAGCCTCCAGGAAAGGGTCTGGAGTGGCTGGGAATGATATGGGG
TGGTGGAAGCACAGACTATAATTCAGCTCTCAAATCCAGACTGAGCATCAGCAA
GGACAACTCCAAGAGCCAAGTTTTCTTAAAAATGAACAGTCTGCAAACTGATGA
CACAGCCATGTACTACTGTGCCAGAAAGACTACGGCTACTCCTACTTTGACTA
CTGGGGCCAAGGCACCACTCTCACAGTCTCCTCA

*Amino acid sequence*
QVQLKESGPGLVAPSQSLSITCTVSGFSLSRYSVHWVRQPPGKGLEWLGMIWGG
GSTDYNSALKSRLSISKDNSKSQVFLKMNSLQTDDTAMYYCARKDYGYSYFDYW
GQGTTLTVSS

*Light-chain variable region (VL); (kappa light chain)*
*Nucleotide sequence*
GATGTTTTGATGACCCAAACTCCACTCTCCCTGCCTGTCAGTCTTGGAGATCAA
GCCTCCATCTCTTGCAGATCTAGTCAGAGCATTGTACATAGTAATGGAAACACC
TATTTAGAATGGTACCTGCAGAAACCAGGCCAGTCTCCAAAGCTCCTGATCTAC
AAAGTTTCCAACCGATTTTCTGGGGTCCCAGACAGGTTCAGTGGCAGTGGATC
AGGGACAGATTTCACACTCAAGATCAGCAGAGTGGAGGCTGAGGATCTGGGA
GTTTATTACTGCTTTCAAGGTTCACATGTTCCATTCACGTTCGGCTCGGGGACA
AAGTTGGAAATAAAACGGGCTGATGCTGCACCAACTGTATCC

*Amino acid sequence*

DVLMTQTPLSLPVSLGDQASISCRSSQSIVHSNGNTYLEWYLQKPGQSPKLLIYKV
SNRFSGVPDRFSGSGSGTDFTLKISRVEAEDLGVYYCFQGSHVPFTFGSGTKLEIK
RADAAPTVS

| FWR1 | CDR1 |
|---|---|

QVQLKESGPGLVAPSQSLSITCTVSGFSLSRYSVHWVR

| FWR2 | CDR2 | FWR3 |
|---|---|---|

QPPGKGLEWLGMIWGGGSTDYNSALKSRLSISKDNSKS

| CDR3 |
|---|

QVFLKMNSLQTDDTAMYYCARKDYGYSYFDYWGQGTTL

TVSS

B.

| FWR1 | CDR1 |
|---|---|

DVLMTQTPLSLPVSLGDQASISCRSSQSIVHSNGNT

| FWR2 | CDR2 | FWR3 |
|---|---|---|

YLEWYLQKPGQSPKLLIYKVSNRFSGVPDRFSGSGS

| CDR3 |
|---|

GTDFTLKISRVEAEDLGVYYCFQGSHVPFTFGSGTK

LEIKRADAAPTVS

METHOD FOR THE TREATMENT OR PROPHYLAXIS OF CANCER BY TARGETING THE EXTRACELLULAR PORTION OF KERATIN 14 (KRT14) RESIDING ON CANCER CELLS

CROSS-REFERENCE TO RELATED APPLICATIONS

This application is a 35 U.S.C. § 371 national stage filing of International Application No. PCT/AU2020/050106, filed on Feb. 7, 2020, which claims priority to Australian Patent Application No. 2019900382, filed on Feb. 7, 2019. The contents of each of the aforementioned applications are hereby incorporated by reference in their entireties.

SEQUENCE LISTING

The instant application contains a Sequence Listing which has been filed electronically in ASCII format and is hereby incorporated by reference in its entirety. Said ASCII copy, created on Feb. 7, 2020, is named PCTAU2020050106-sql-000001-EN-20200207.txt and is 6,950 bytes in size.

FIELD

The present invention relates generally to cancer therapy including the treatment, prevention or retardation of development or metastasis of cancer and to medicaments useful for same.

BACKGROUND

Bibliographic details of the publications referred to by author in this specification are collected alphabetically at the end of the description.

Reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavor to which this specification relates.

Cancer remains one of the most significant diseases affecting humans and animals with high rates of morbidity and mortality. Ovarian cancer, for example, is the ninth most common cancer diagnosed in women. In fact, ovarian cancer is the most lethal of all gynaecological cancers. Significant resources have been expended in the early diagnosis and treatment of ovarian cancer. Despite improvements in surgical and chemotherapeutic interventions, ovarian cancer survival rates remain steady at approximately 25% (Vaughan et al. (2011) *Nat Rev Cancer* 11(10):719-725).

Over 75% of ovarian cancer patients are diagnosed with late stage metastatic disease on first clinical presentation. The treatment is largely limited to aggressive surgery and chemotherapy. Notwithstanding, over 90% of patients relapse, often within the first year following treatment. In the vast majority of these patients, recurrent tumors exhibit chemoresistence. This phenomenon limits further therapeutic options and underlies the very high mortality rate for ovarian cancers.

Attempts at genetic screening to identify potential therapeutic targets have, despite substantial effort, been largely unsuccessful. This is likely due to the highly heterogeneous nature of ovarian cancer tissues.

Keratin-14 (KRT14) is an intracellular protein component of the cytoskeleton, typically expressed in a primitive lineage of progenitor cells residing in myoepithelial and epithelial niches in healthy adult tissues (Chu et al. (2001) *Histopathology* 39(1):9-16; Paraskevopoulou et al. (2016) *Cell Cycle* 15(23):3161-3162). In tumor tissue, KRT14 marks a population of specialized cells (alternately described as "leader cells", "cancer stem cells" or "tumor initiating cells") that control the ability of tumor deposits to invade into healthy tissues. KRT14-expressing cells are mechanistically implicated in controlling tumor invasion across a range of solid tumor types (including breast, bladder and lung). In these tumors, the presence of cells expressing KRT14 is directly correlated with tumor invasive potential and a reduction in disease-free and overall survival (Chu et al. (2001) supra; Cheah et al. (2015) *Proc Natl Acad Sci USA* 112(15):4725-4730; Volkmer et al. (2012) *Proc Natl Acad Sci USA* 109(6):2078-2083; Ho et al. (2012) *Nat Rev Urol* 9(10):583-594; Cheung et al. (2016) *Proc Natl Acad Sci USA* 113(7):E854-863; Cheung et al. (2013) *Cell* 155(7): 1639-1651; Papafotiou et al. (2016) *Nat Commun* 7:11914).

There is an urgent need for a therapeutic approach which can improve patient prognosis and quality of life.

SUMMARY

In accordance with the present invention, it is established that KRT14 is essential for ovarian cancer cell invasion through a mesothelial layer in vitro; and for the successful implantation of ovarian tumor in vivo. It is also established herein that KRT14 plays a role in the migration and invasion of other cancer cell types, including colorectal, endometrial, brain, breast and lung cancer cells. KRT14 is not expressed in the healthy tissue, including normal reproductive tract such as the ovary and fallopian tubes. Importantly, it is determined that KRT14 has an extracellular portion which is present in a range of cancers in both male and female subjects. The term "extracellular" is to be understood as meaning a portion, segment or domain of KRT14 that is located on, exposed to, or otherwise accessible from, the outside of the cell.

Accordingly, taught herein is a method for the treatment or prophylaxis of cancer in a mammalian subject, including human and animal subjects, the method comprising administering to the subject an amount of an agent which targets an extracellular portion of KRT14 or its functional homolog or variant resident on cancer cells or an agent which induces in vivo production of an antagonist of the extracellular portion of KRT14 or its functional homolog or variant on cancer cells, the amount effective to prevent cancer cell invasion, migration and/or metastisization. By "administering" to a subject includes contacting cancer cells. A "subject" may be male or female.

In an embodiment, the cancer is a gynecological cancer including but not limited to ovarian cancer or a form or stage of ovarian cancer. In an embodiment, the cancer is endometrial or colorectal cancer. In an embodiment, the cancer is selected from brain, bladder, liver, breast, lung, pancreatic, bowel, colon, gastrointestinal tract, stomach, throat, endometrial and colorectal cancer.

In an embodiment, the agent is an antibody which targets an epitope contained within a protein comprising the peptide sequence (in single letter code): GFGGGYGGGL-GAGLGGGFGGGFAGGDGL (SEQ ID NO:1), or its functional homolog or a variant having at least 80% similarity to SEQ ID NO:1 after optimal alignment. Other agents acting as antagonists or targeting agents of SEQ ID NO:1 are also contemplated herein. SEQ ID NO:1 represents the human sequence. Homologs in other species are also contemplated herein as therapeutic and diagnostic targets. The "antibody" includes a monoclonal antibody, a polyclonal antibody and KRT14-binding anti-serum as well as recombinant forms, fragments and derivatives that bind the exogenous portion of KRT14 or part thereof.

In an embodiment disclosed herein, the agent comprises an immunoglobulin heavy chain variable domain (VH) and an immunoglobulin light chain variable domain (VL), wherein the VH comprises a complementarity determining region 1 (VH CDR1) comprising the amino acid sequence of SEQ ID NO:6, a VH CDR2 comprising the amino acid sequence of SEQ ID NO:7 and a VH CDR3 comprising the amino acid sequence of SEQ ID NO:8; and wherein the VL comprises a complementarity determining region 1 (VL CDR1) comprising the amino acid sequence of SEQ ID NO:9, a VL CDR2 comprising the amino acid sequence of SEQ ID NO:10, and a VL CDR3 comprising the amino acid sequence of SEQ ID NO:11.

In an embodiment, the VH comprises:
(a) a VH framework region 1 (FR1) comprising an amino acid sequence having at least 80% sequence identity to SEQ ID NO:12;
(b) a VH FR2 comprising an amino acid sequence having at least 80% sequence identity to SEQ ID NO:13;
(c) a VH FR3 comprising an amino acid sequence having at least 80% sequence identity to SEQ ID NO:14; and
(d) a VH FR4 comprising an amino acid sequence having at least 80% sequence identity to SEQ ID NO:15;
and the VL comprises:
(e) a VL FR1 comprising an amino acid sequence having at least 80% sequence identity to SEQ ID NO:16;
(f) a VL FR2 comprising an amino acid sequence having at least 80% sequence identity to SEQ ID NO:17;
(g) a VL FR3 comprising an amino acid sequence having at least 80% sequence identity to SEQ ID NO:18; and
(h) a VL FR4 comprising an amino acid sequence having at least 80% sequence identity to SEQ ID NO:19.

In an embodiment, the VH comprises an amino acid sequence having at least 80% sequence identity to SEQ ID NO:3, and the VL comprises an amino acid sequence having at least 80% sequence identity to SEQ ID NO:5.

In an embodiment, the mammalian subject is a human female or human male. Notwithstanding, the present invention extends to veterinary applications in non-human male or female mammals.

As taught herein, a novel function for KRT14 is identified as being a critical early regulator of ovarian cancer invasion and deposition. Cells lacking a functional copy of the KRT14 gene are invasion-incompetent, and are unable to establish ovarian tumors in vivo. Targeting the epitope identified by SEQ ID NO:1 with an exogenously added agent which targets SEQ ID NO:1 completely abrogates the invasive capacity of cancer cells in vitro, micking the effects of functional KRT14 loss. Similarly, inducing an in vivo response such as an immune response specific to cells carrying SEQ ID NO:1 is also effective in reducing cancer development.

In an embodiment, the present specification teaches a method for the treatment of ovarian cancer in a human subject, the method comprising administering to the subject, an amount of an antibody which targets an extracellular portion of KRT14 defined by SEQ ID NO:1 resident on ovarian cancer cells, the amount effective to prevent or reduce ovarian cancer cell invasions, migration and/or metastisization.

Many other solid tumor types (e.g., breast, bladder, lung and others) are proposed to employ this KRT14 mediated mechanism of invasion, indicating that anti-KRT14 directed therapy is broadly applicable across a range of solid tumor types.

Medicaments which target SEQ ID NO:1 or its functional homolog or variant to thereby abrogate cancer cell invasion, migration and/or metastisization are enabled herein. In an embodiment, the medicament comprises an antibody specific for SEQ ID NO:1 or its functional homolog or variant. As indicated above, the antibody may be a polyclonal or monoclonal antibody or anti-serum comprising KRT14-binding antibodies or may be a synthetic (e.g., recombinant) antibody or a KRT14-binding fragment or derivative of any of the foregoing. The antibody may also be a cartilage animal derived antibody or a KRT14-binding fragment or derivative thereof. The medicament, in addition to being an antibody, may be any affinity reagent including but not limited to aptamers, monobodies, anti-calins, DARPins and nanobodies and the like.

The present invention extends to combination therapy where the agent targeting KRT14 or the agent inducing an in vivo KRT14 antagonist is given with another anti-cancer agent and/or radiation therapy and/or surgical intervention. Examples of additional agents include a chemotherapeutic agent such as one or more of dactinomycin, daunorubicin, doxorubicin (adriamycin), idarubicin and mitoxantrone, or platinum based agents or an antimetabolite. Antimetabolites are substances that interfere with the body's chemical processes, such as creating proteins, DNA, and other chemicals needed for cell growth and reproduction; in cancer treatment, antimetabolite drugs disrupt DNA production, which in turn prevents cell division. Examples include azaserine, D-cycloserine, nycophenolic acid, trimethoprim, 5-fluorouracil, capecitabine, methotrexate, gemcitabine, cytarabine (ara-C) and fludarabine. Other immune reagents may be administered such as primed T-cells and cytokines. Combination therapy may be provided simultaneously or sequentially in either order and within seconds, minutes, hours, days or weeks of each other.

The present disclosure also extends to an agent that binds specifically to an extracellular portion of KRT14 on cancer cells, or a KRT14-binding fragment thereof, wherein the agent comprises an immunoglobulin heavy chain variable domain (VH) and an immunoglobulin light chain variable domain (VL), wherein the VH comprises a complementarity determining region 1 (VH CDR1) comprising the amino acid sequence of SEQ ID NO:6, a VH CDR2 comprising the amino acid sequence of SEQ ID NO:7 and a VH CDR3 comprising the amino acid sequence of SEQ ID NO:8; and wherein the VL comprises a complementarity determining region 1 (VL CDR1) comprising the amino acid sequence of SEQ ID NO:9, a VL CDR2 comprising the amino acid sequence of SEQ ID NO:10, and a VL CDR3 comprising the amino acid sequence of SEQ ID NO:11.

In an embodiment, the VH comprises:
(a) a VH framework region 1 (FR1) comprising an amino acid sequence having at least 80% sequence identity to SEQ ID NO:12;
(b) a VH FR2 comprising an amino acid sequence having at least 80% sequence identity to SEQ ID NO:13;
(c) a VH FR3 comprising an amino acid sequence having at least 80% sequence identity to SEQ ID NO:14; and
(d) a VH FR4 comprising an amino acid sequence having at least 80% sequence identity to SEQ ID NO:15;

and the VL comprises:

(e) a VL FR1 comprising an amino acid sequence having at least 80% sequence identity to SEQ ID NO:16;

(f) a VL FR2 comprising an amino acid sequence having at least 80% sequence identity to SEQ ID NO:17;

(g) a VL FR3 comprising an amino acid sequence having at least 80% sequence identity to SEQ ID NO:18; and (h) a VL FR4 comprising an amino acid sequence having at least 80% sequence identity to SEQ ID NO:19.

In an embodiment, the VH comprises an amino acid sequence having at least 80% sequence identity to SEQ ID NO:3, and the VL comprises an amino acid sequence having at least 80% sequence identity to SEQ ID NO:5.

Amino acid sequences are referred to by a sequence identifier number (SEQ ID NO). The SEQ ID NOs correspond numerically to the sequence identifiers <400>1 (SEQ ID NO:1), <400>2 (SEQ ID NO:2), etc. A sequence listing is provided after the claims.

A summary of the sequence identifier used throughout the subject specification is provided in Table 1.

TABLE 1

Summary of sequence identifier

| SEQUENCE ID NO: | DESCRIPTION |
|---|---|
| 1 | Amino acid sequence of extracellular portion of human KRT14 comprising an epitope |
| 2 | Nucleic acid sequence encoding the heavy chain variable region of monoclonal antibody (mAb) AN-17 |
| 3 | Amino acid sequence of the heavy chain variable region of monoclonal antibody AN-17 |
| 4 | Nucleic acid sequence encoding the light chain variable region of monoclonal antibody AN-17 |
| 5 | Amino acid sequence of the light chain variable region of monoclonal antibody AN-17 |
| 6 | Amino acid sequence of the heavy chain CDR1 of monoclonal antibody AN-17 |
| 7 | Amino acid sequence of the heavy chain CDR2 of monoclonal antibody AN-17 |
| 8 | Amino acid sequence of the heavy chain CDR3 of monoclonal antibody AN-17 |
| 9 | Amino acid sequence of the light chain CDR1 of monoclonal antibody AN-17 |
| 10 | Amino acid sequence of the light chain CDR2 of monoclonal antibody AN-17 |
| 11 | Amino acid sequence of the light chain CDR3 of monoclonal antibody AN-17 |
| 12 | Amino acid sequence of the heavy chain FR1 of monoclonal antibody AN-17 |
| 13 | Amino acid sequence of the heavy chain FR2 of monoclonal antibody AN-17 |
| 14 | Amino acid sequence of the heavy chain FR3 of monoclonal antibody AN-17 |
| 15 | Amino acid sequence of the heavy chain FR4 of monoclonal antibody AN-17 |
| 16 | Amino acid sequence of the light chain FR1 of monoclonal antibody AN-17 |
| 17 | Amino acid sequence of the light chain FR2 of monoclonal antibody AN-17 |
| 18 | Amino acid sequence of the light chain FR3 of monoclonal antibody AN-17 |
| 19 | Amino acid sequence of the light chain FR4 of monoclonal antibody AN-17 |

Amino acids may be referred to by name or by single or three letter code (Table 2).

TABLE 2

Amino acid three and single letter

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenyialanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Pyrrolysine | Pyl | O |
| Selenocysteine | Sec | U |
| Any residue | Xaa | X |

BRIEF DESCRIPTION OF THE FIGURES

Some figures contain color representations or entities. Color photographs are available from the Patentee upon request or from an appropriate Patent Office. A fee may be imposed if obtained from a Patent Office.

(FIG. 1A) Ovarian cancer spheroids were cultured using a peritoneal microenvironment model, and invasion through a mesothelial barrier monitored. Cryosections containing spheroids actively breaching an LP9 mesothelial cell monolayer were (FIG. 1B) assessed by MALDI imaging mass spectrometry, which identified KRT14 amongst several proteins at the invasive interface. (FIG. 1C) Immunostaining of spreading ovarian cancer cells (OVCAR4) for KRT14, showing localization to the invadopodia. A magnified region is shown (upper right). KRT14 staining appears green against a black background. Nuclear staining by DAPI in blue.

(FIG. 2A) Proliferation and invasion were measured using xCELLigence. Loss of KRT14 expression had no effect on proliferation, but completely abrogated invasion through a mesothelial monolayer in vitro. (FIG. 2B) Cells lacking KRT14 fail to repair wounds overnight using an in vitro scratch test.

(FIG. 3A) ID8 cells were successfully engrafted to a single ovary in each mouse, and were detectable and localized to the site of implant. After 4 weeks, fluorescence was lost from mice implanted with K14$^{KO}$ cells. (FIG. 3B) Fluorescence increased in mice bearing wild-type tumor cells at ~3-4 weeks; no similar increase in fluorescence was detectible in mice implanted with KRT14$^{-KO}$ cells. (FIG. 3C) Mice were culled at ~7 weeks and autopsy performed. Mice implanted with wild-type ID8 cells formed large primary ovarian tumors, with metastases to the contralateral ovary, peritoneal walls, liver, intestine and diaphragm, and displayed significant accumulation of ascites fluid in the peritoneal cavity. By contrast, mice implanted with KRT14$^{KO}$ cells did not develop ascites, and no tumors were observed. Tumor cells could not be detected at autopsy in these mice.

Figure 4A:
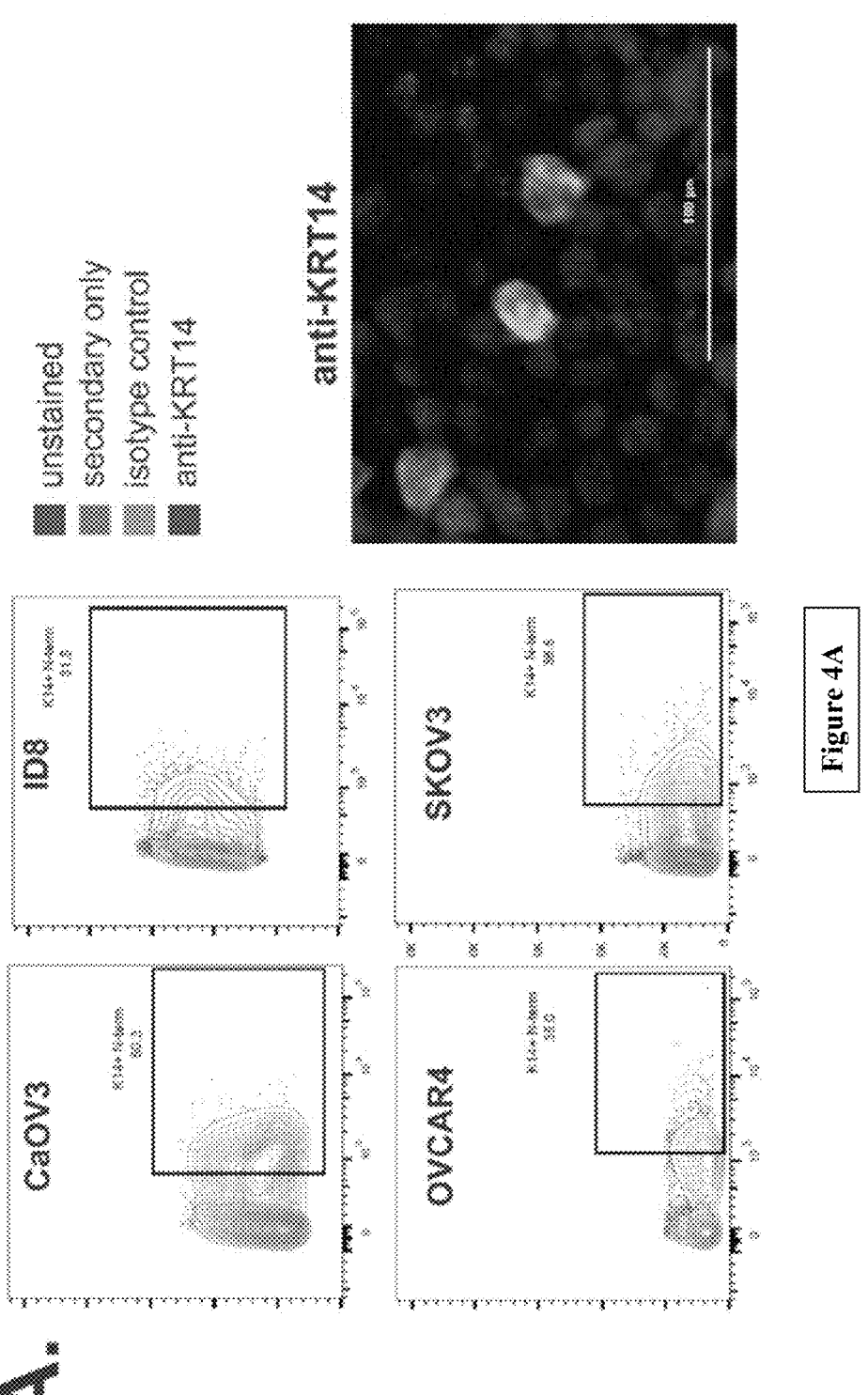
Figure 4:
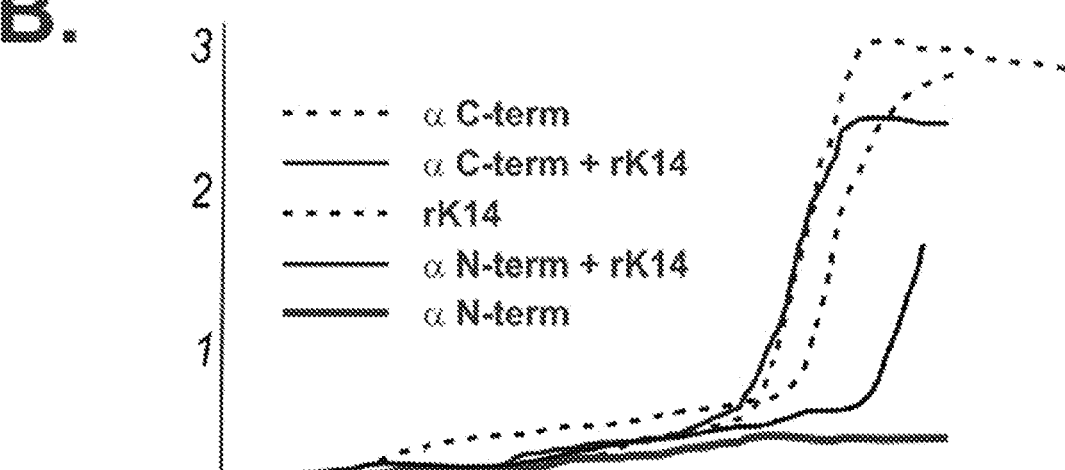

FIGS. 4A and 4B are graphical and photographical representations showing that the N-terminus of KRT14 is exposed at the cell surface, and is accessible to exogenously added antibodies. (FIG. 4A) Flow cytometry was performed on intact, non-permeabilized ovarian cancer cells (identities as indicated), using polyclonal antibodies against the N-terminal region of KRT14. Between 30-50% of cells were positively stained for cell-surface KRT14. Immunostaining of intact cells in culture confirmed staining of a subset of cells with the anti-KRT14 antibodies. (FIG. 4B) Antibodies against either the N- and C-termini of KRT14 were tested for their ability to inhibit invasion by ovarian cancer cells in vitro. Anti-C-terminal antibodies (a C-term) had no effect on invasion, whilst anti N-terminal antibodies (a N-term) completely blocked invasion. Exogenously added, full-length recombinant KRT14 protein (rK14) had no effect alone or in combination with a C-term antibody. However, rK14 successfully competed with a N-term antibody to restore invasive capacity in vitro.

Figure 5A:
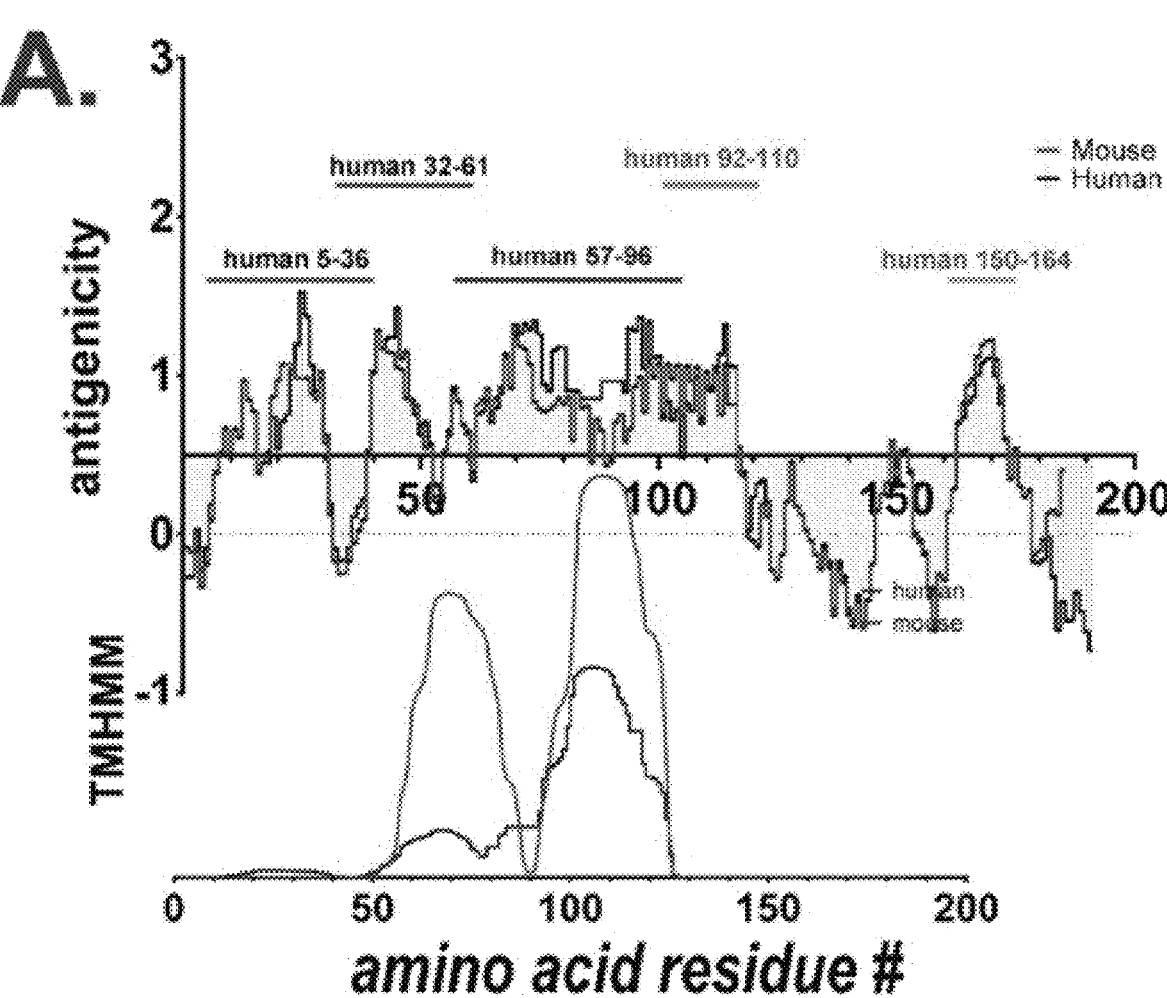
Figure 5B:
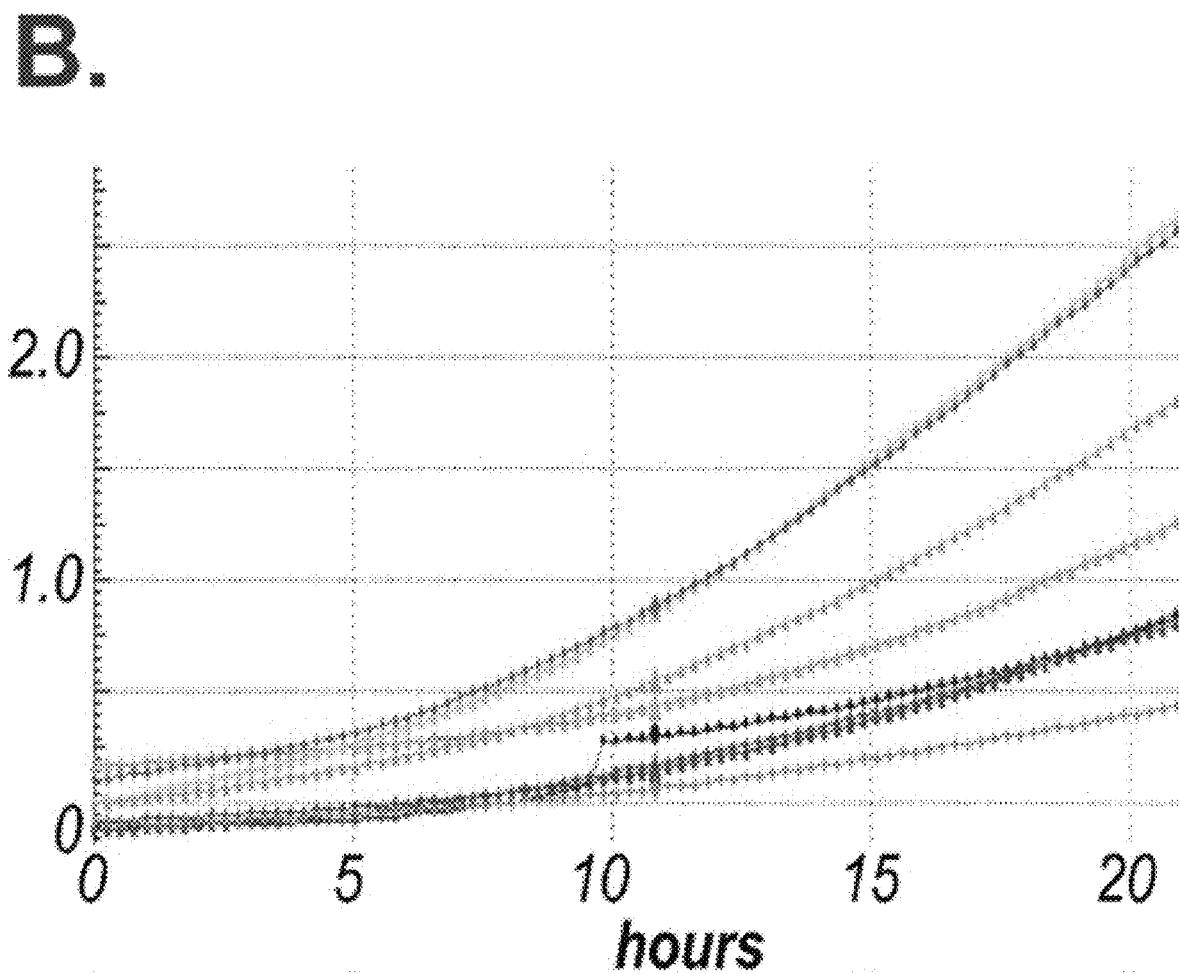
Figure 5C:
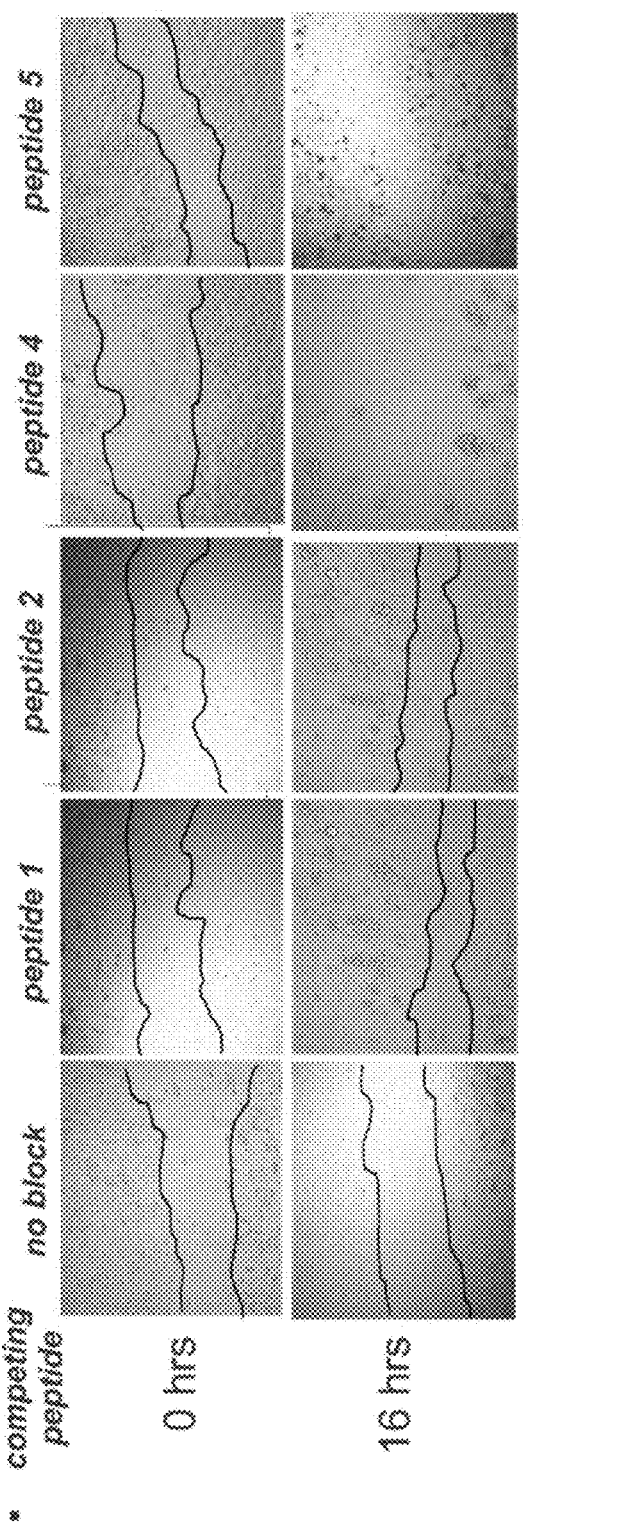

FIGS. 5A through 5C are graphical and photographical representations showing that a single antigenic region in the N-terminus of KRT14 is exposed and can be targeted to block invasion in vitro. (FIG. 5A) Antigenicity and hydrophobicity of the N-terminus of KRT14 were predicted in silico using the publicly available IEDB portal. Five regions of potential antigenicity were predicted, and six corresponding peptides synthesized. (FIG. 5B) Competition assays using individual peptides were used to map the relevant region of KRT14 recognized by polyclonal antibodies. Two peptides, encompassing amino acids 83-110 (human sequence), successfully restored invasive capacity in Xcelligence assays. (FIG. 5C) In a parallel wound healing experiment, the same two peptides (#4 and #5) successfully competed with anti N-terminal KRT14 antibodies to restore cell migration and effect complete wound closure over 16 hours.

Figure 6:
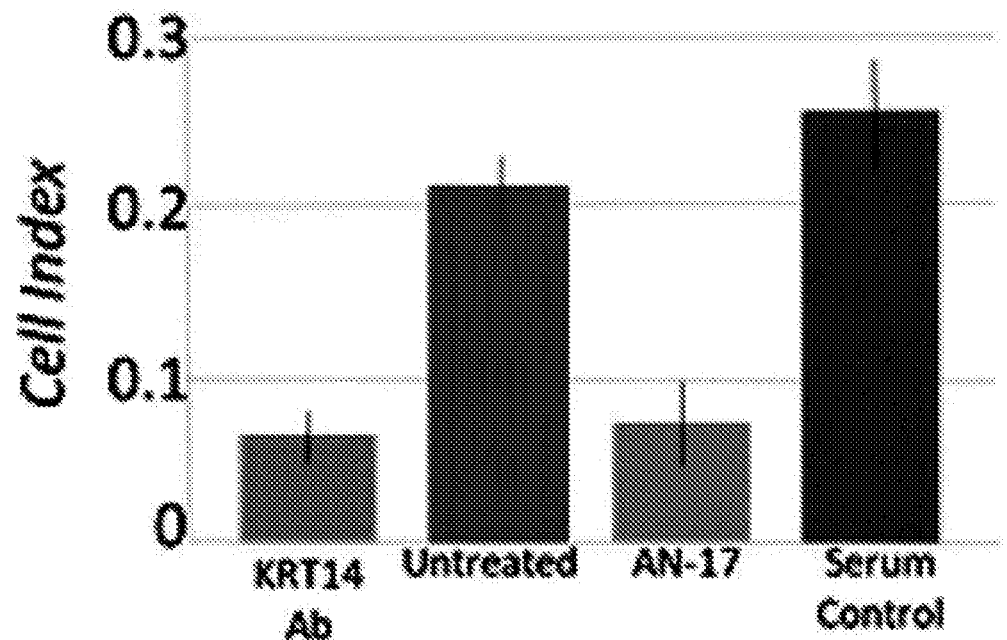

FIGS. 6A and 6B are graphical representations showing anti-sera AN-17 O20023 effectively blocks cancer cell invasion in vitro. (FIG. 6A) Anti-sera raised against the specific KRT14 epitope effectively inhibited invasion, with comparable efficacy to a commercial polyclonal antibody (Sigma SAB4501657). (FIG. 6B) Inhibition of invasion by anti-KRT14 had no impact on cell viability.

Figure 7:
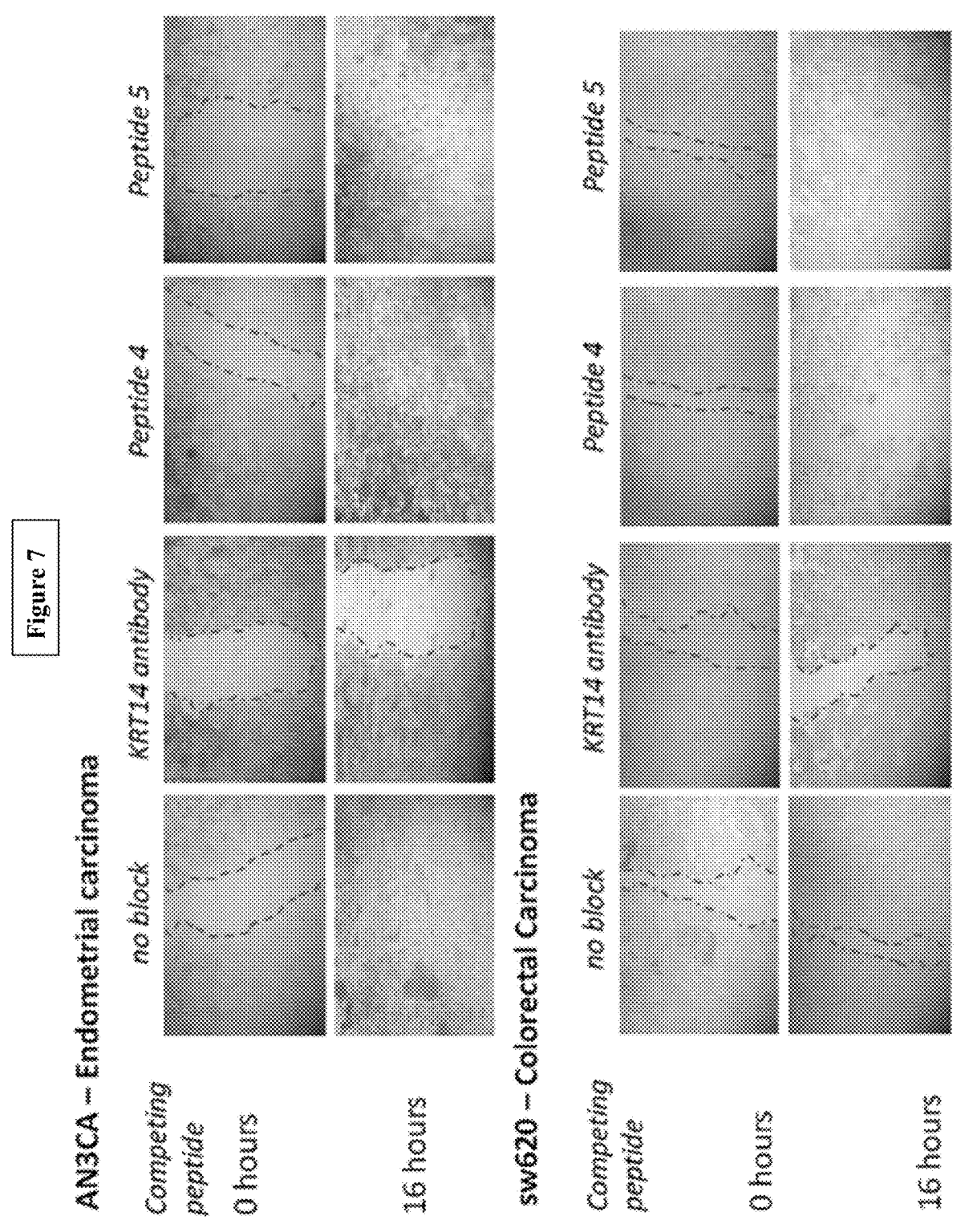

FIG. 7 is a photographic representation showing migration of non-ovarian cancer cell types is impaired by anti-KRT14 antibody in vitro. Anti-KRT14 antibody prevent wound closure in cell monolayers comprised by endometrial or colorectal carcinoma cells. Short peptides (peptides 4 and 5) mimicking the KRT14 epitope of interest could effectively compete for antibody binding to re-establish migration in vitro.

Figure 8A:
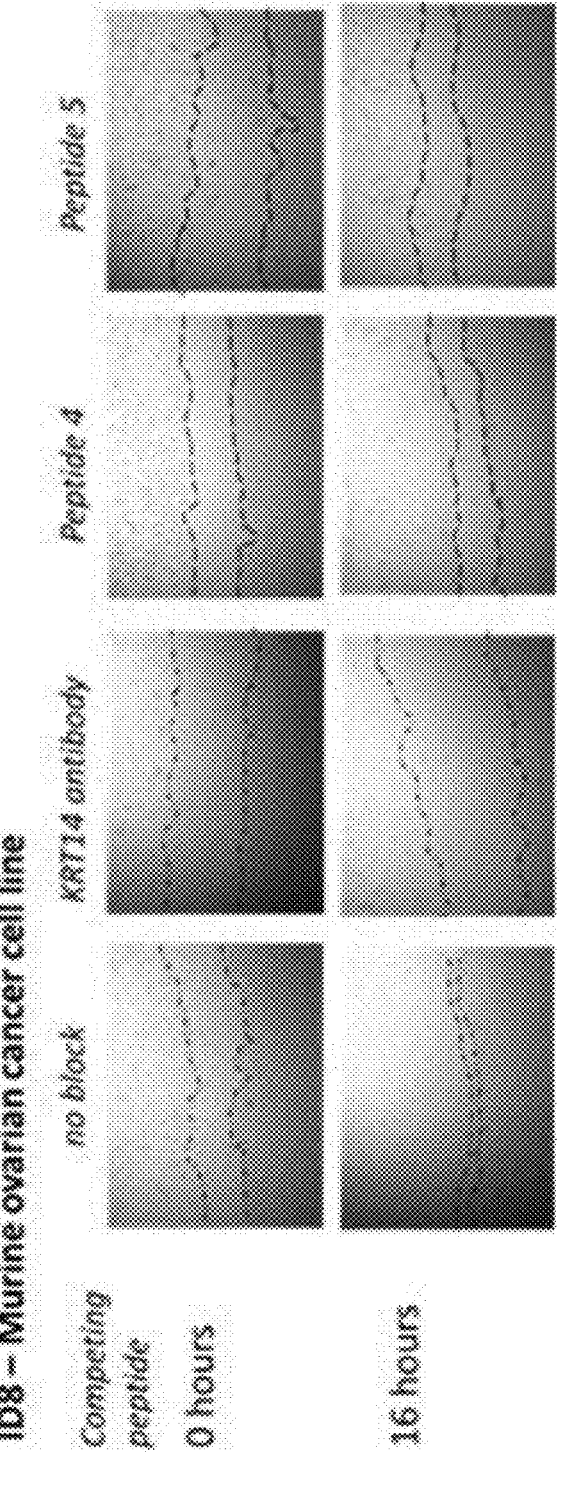
Figure 8:
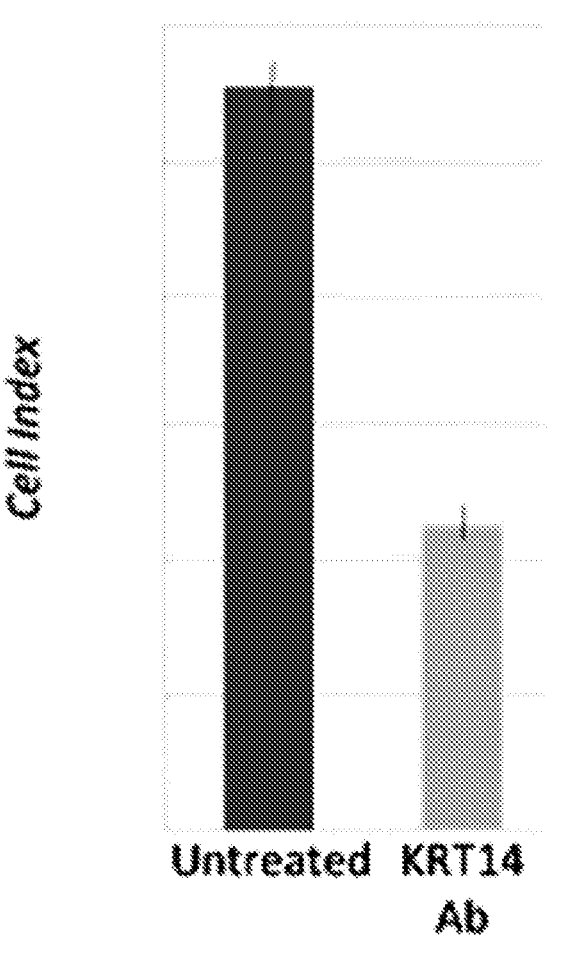

FIGS. 8A and 8B are photographical and graphical representations showing migration of murine ovarian cancer cells is impaired by anti-KRT14 antibody in vitro. (FIG. 8A) Anti-KRT14 antibody prevented wound closure in cell monolayers comprised of murine ID8 ovarian cancer cells. Short peptides (peptides 4 and 5) mimicking the KRT14 epitope of interest could effectively compete for antibody binding to re-establish migration in vitro. (FIG. 8B) RTCA analysis confirmed that anti-human KRT14 antibody blocked invasion of murine ovarian cancer cells in vitro.

Figure 9:
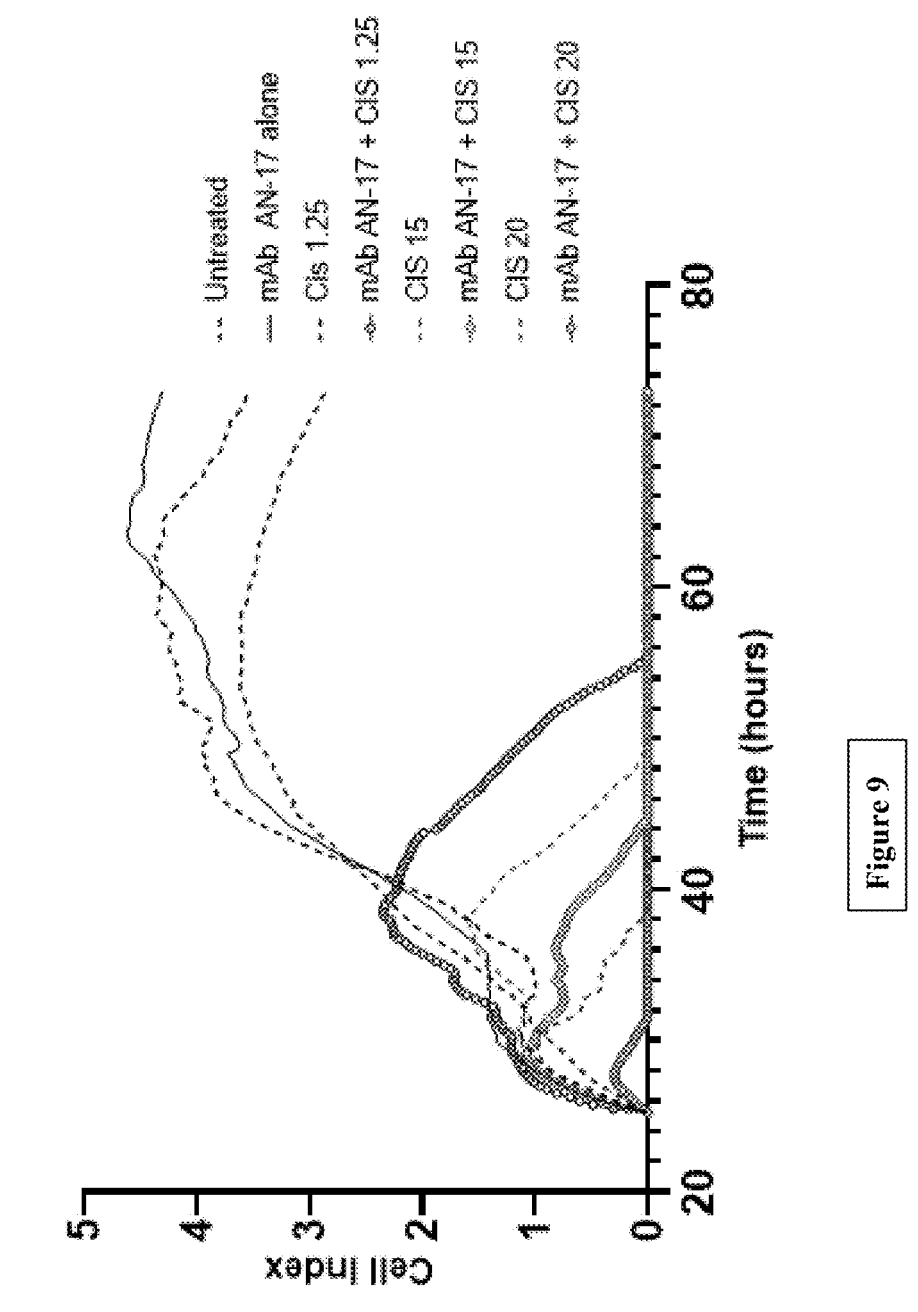

FIG. 9 shows that the monoclonal anti-KRT14 antibody AN-17 (mAb AN-17) increases sensitivity to platinum chemotherapy in vitro. OVCAR4 ovarian cancer cells were incubated with mAb AN-17, cisplatin or a combination of the two, and cell proliferation monitored over a 72 hr period. Cells treated with a combination of mAb AN-17 plus cisplatin showed significantly lower IC50 compared to cisplatin alone. Notably, mAb AN-17 significantly enhanced the toxicity of cisplatin used at sub-lethal doses (n=3/treatment, mean cell indices).

Figure 10:
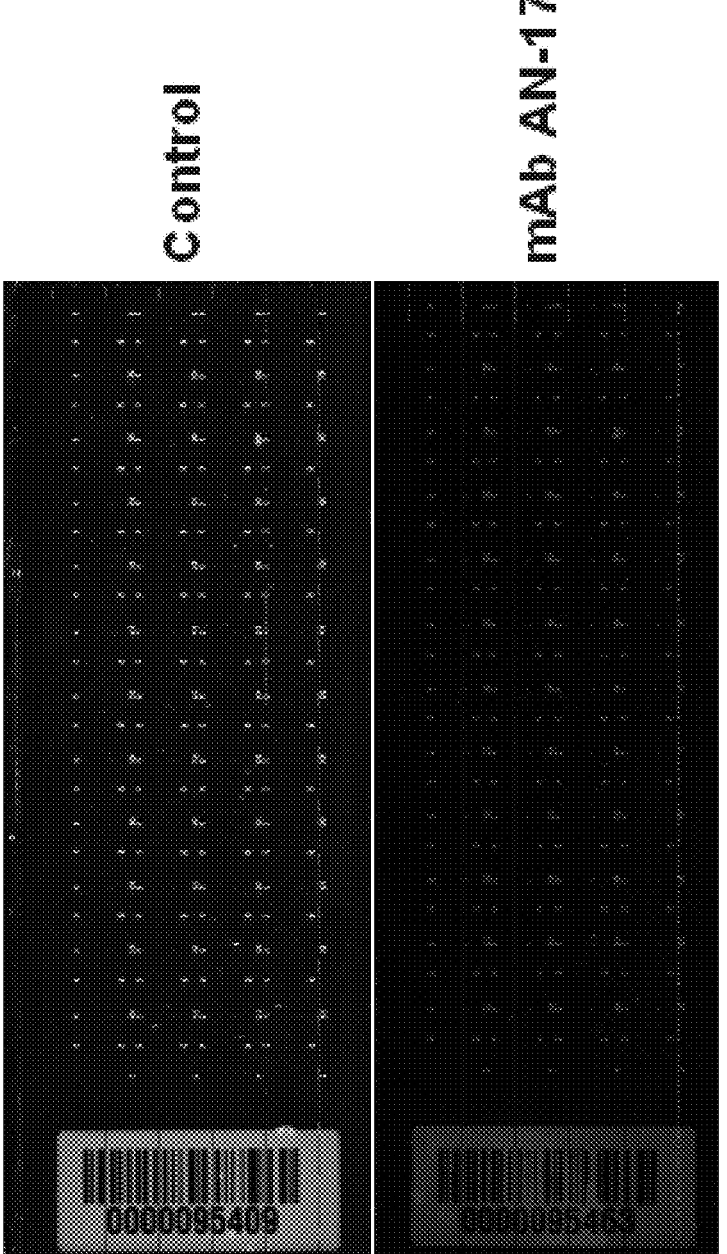

FIG. 10 shows that mAb AN-17 displays no cross-reactivity with multiple protein antigens in vitro. Protein arrays were used to identify any cross-reacting proteins that may potentially be recognized by mAb AN-17. No cross-reactivity was evident, suggesting high specificity of mAb AN-17 for KRT14.

Figure 11:
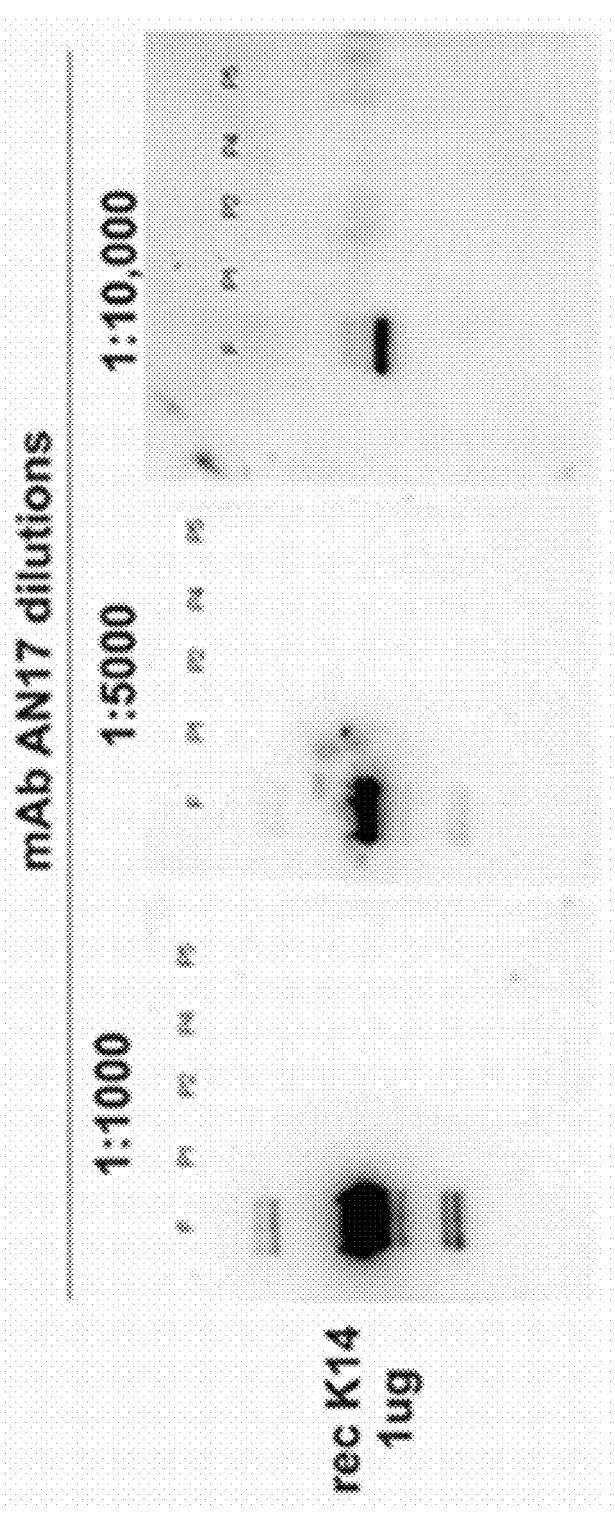

FIG. 11 shows western blotting for KRT14 detection using mAb AN-17. Antibody dilutions from 1:1000 to 1:10,000 successfully detected KRT14 protein by western blotting.

Figure 12:
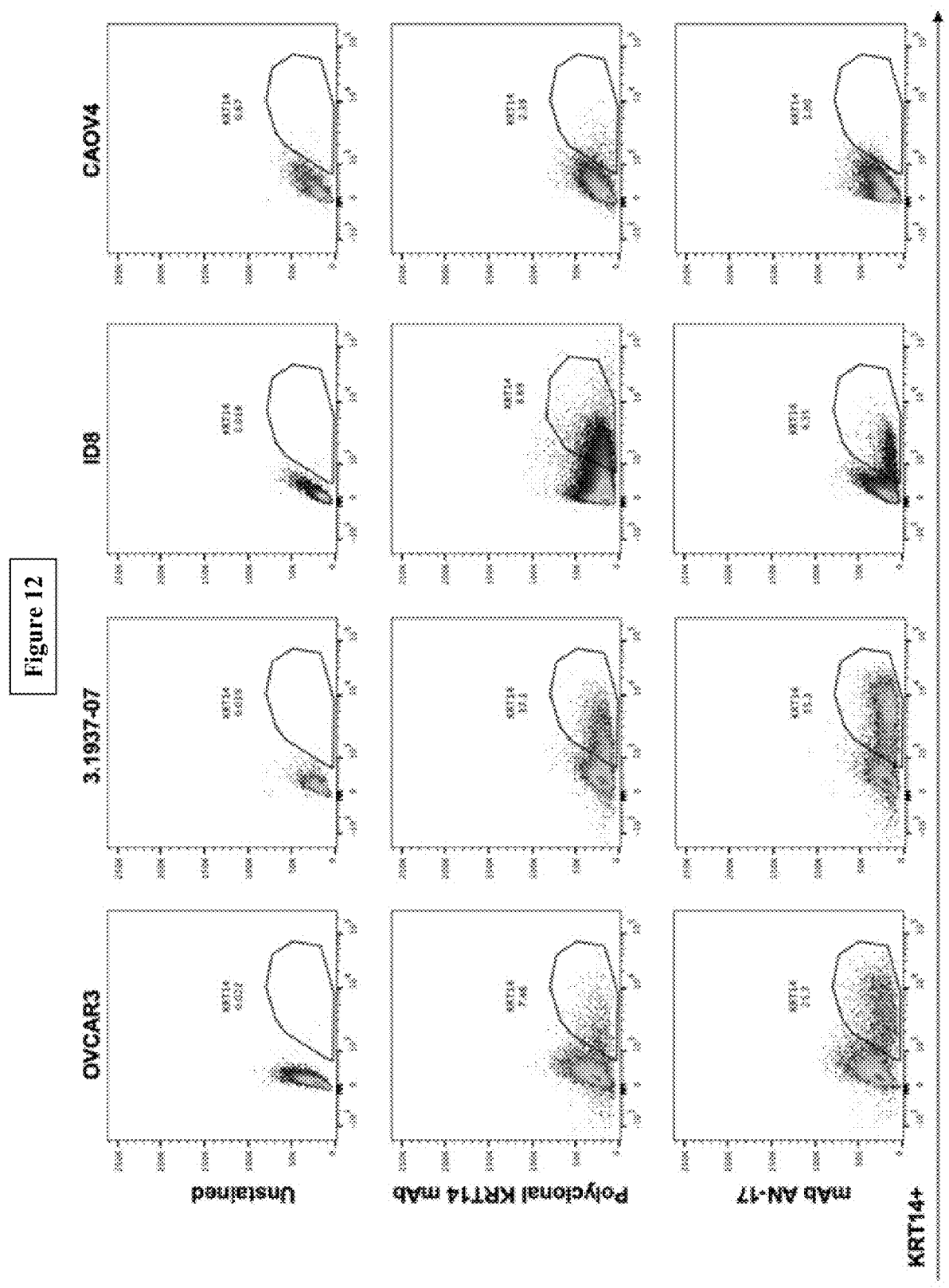

FIG. 12 shows that mAb AN-17 can identify KRT14+ cells in human and murine ovarian cancer cells. OVCAR3, CAOV4, ID8 and the patient-derived 3.1937-07 cell lines were analysed on a BD LSRFortessa X-20 (BD Biosciences) flow cytometer for KRT14+ cell populations, using mAb AN-17 or a commercially available polyclonal antibody to KRT14 (Sigma SAB4501657).

Figure 13:
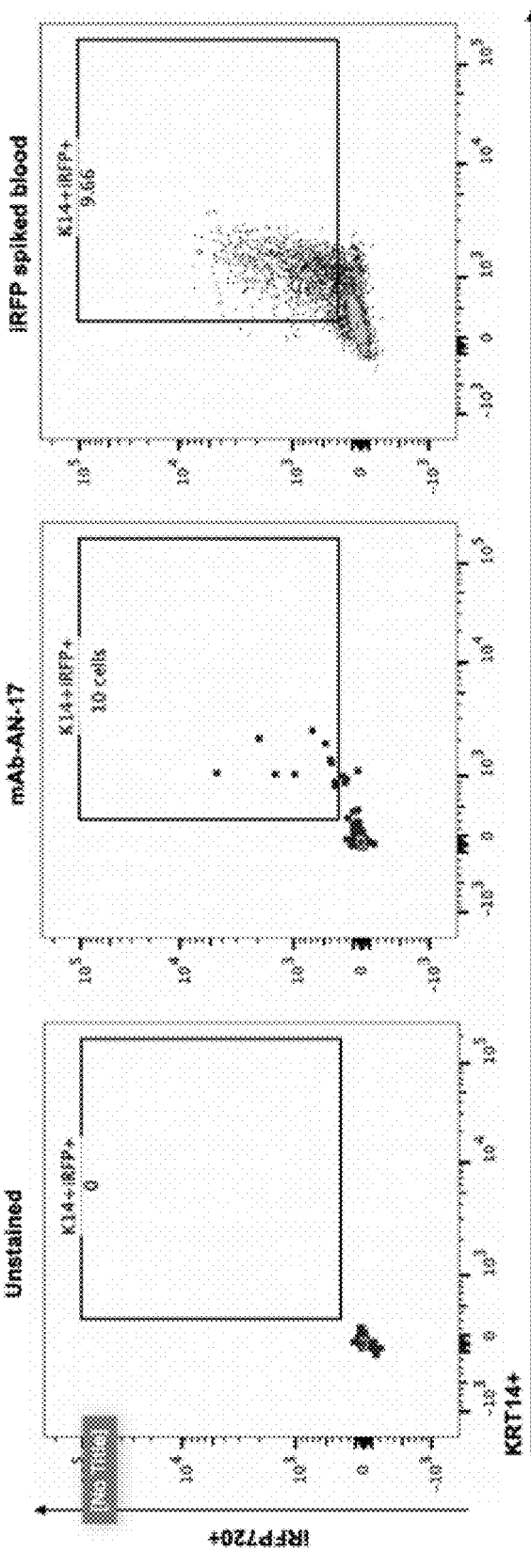

FIG. 13 shows circulating tumour cell detection with mAb AN17 in mice bearing epithelial ovarian tumours. Cardiac blood was taken from mice bearing 12-week old ID8 iRFP720+ epithelial ovarian tumours and stained using anti-CD45 and mAb AN-17. Circulating ID8 tumour cells were identified as KRT14+ CD45– cells and confirmed by iRFP720+ status. iRFP720+ ID8 cells spiked into blood was used as a positive control.

Figure 14:
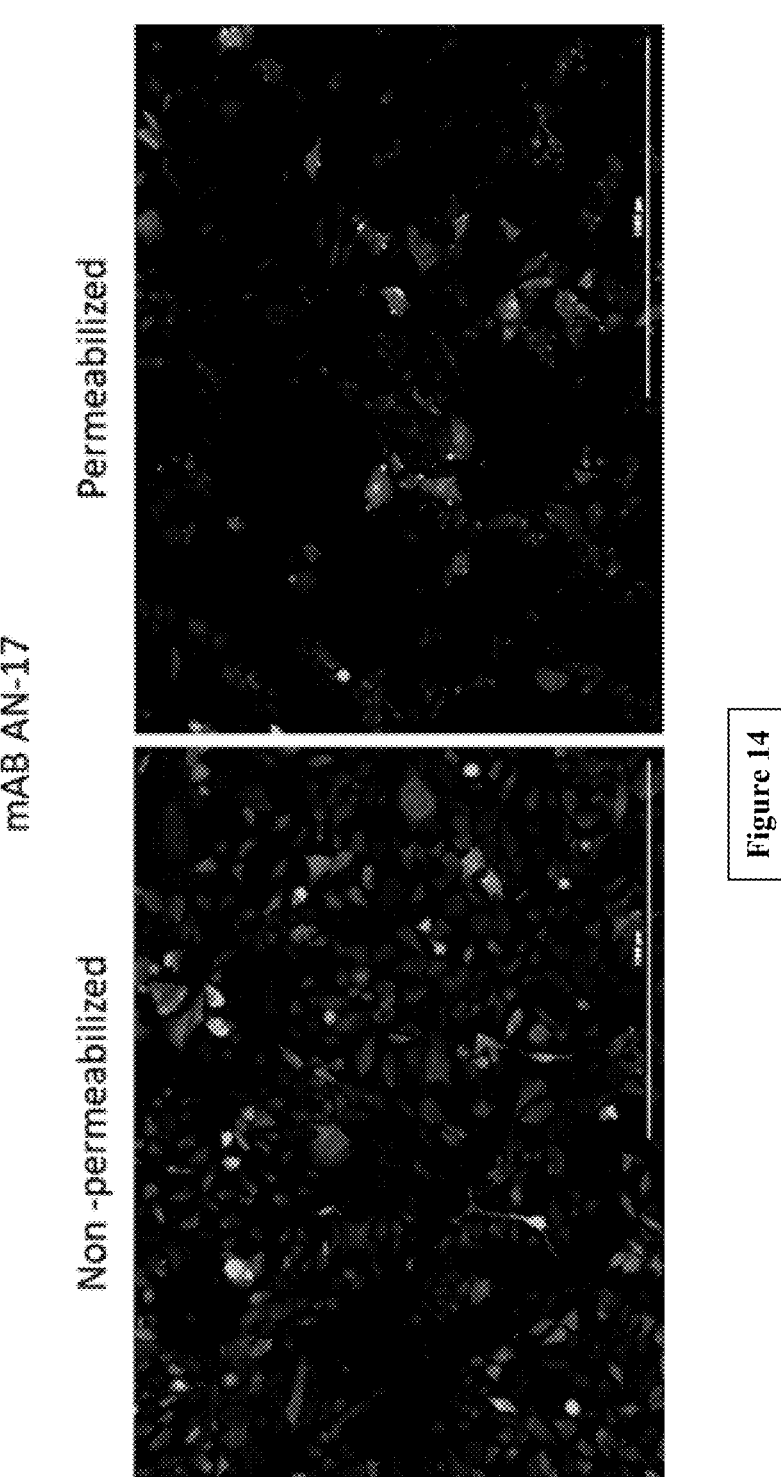

FIG. 14 shows detection of KRT14+ cells by immunofluorescence staining. Cancer cells were incubated with mAb AN-17 either intact (left) or following permeabilization (right), to label surface- or intracellular KRT14, respectively.

Figure 15:
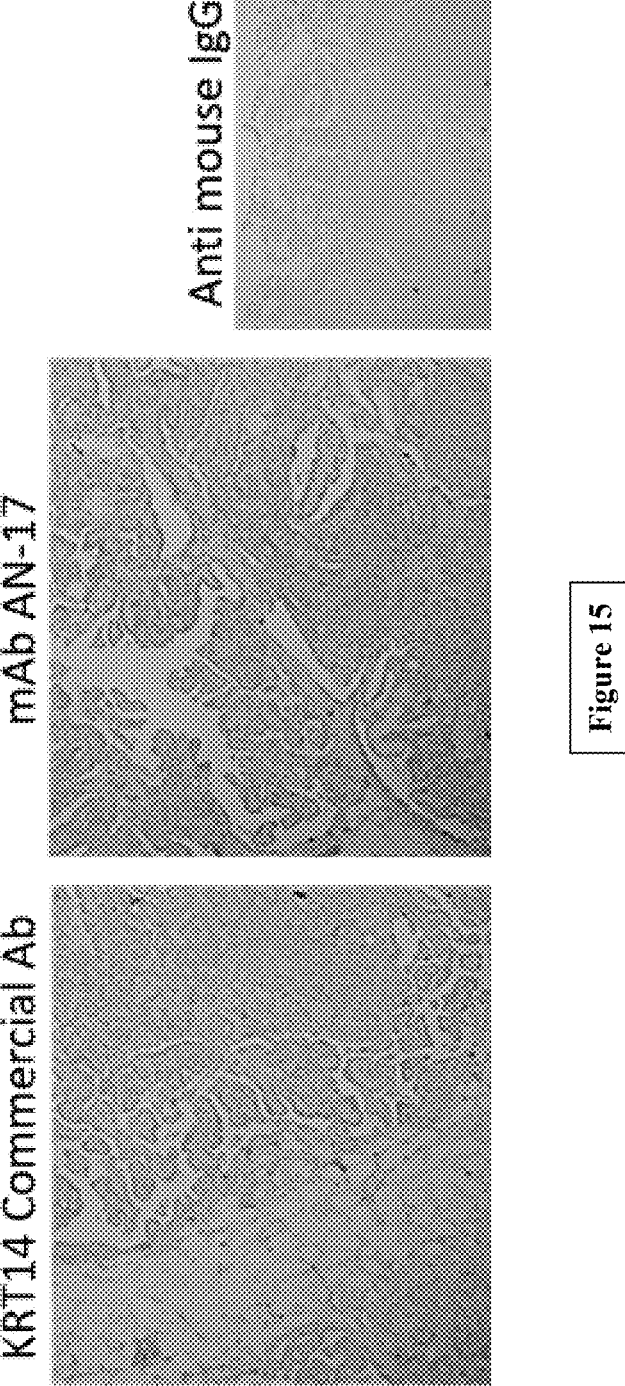

FIG. 15 shows immunohistochemical staining of tumour tissue using mAb AN-17. Staining was restricted to tumour epithelium, and was similar to a commercially available polyclonal anti-KRT14 antibody (Sigma SAB4501657).

FIGS. 16A-16D show non-specific tissue uptake of mAb AN-17 and clearance over a 7-day period. Mice without tumours were injected with mAb AN-17 at 0.5 mg/kg (i.p.), and the tissue distribution was assessed over time by monitoring fluorescence. Comparisons were made against a non-targeted IgG-kappa isotype control antibody. There was no non-specific retention of mAb AN-17 observed, and both antibodies (mAb AN-17 and control IgG-kappa) were almost undetectable after 7 days. Tissues examined included reproductive organs (ovaries, fallopian tubes, uterus) (FIG. 16A); intestine (FIG. 16A); liver (FIG. 16B); kidney (FIG. 16B); spleen (FIG. 16C); lung (FIG. 16C); heart (FIG. 16D); and brain (n=2 animals/group, mean+/–SD) (FIG. 16D). Measurements at each time point are offset against the axis to make overlapping datasets clear.

FIGS. 17A-17D show non-specific tissue uptake of mAb AN-17 and clearance over a 7 day period. Mice without tumours were injected with mAb AN-17 at 0.5, 1.0, 2.5, 5.0 or 10.0 mg/kg (i.p.), and the tissue distribution over time was assessed by monitoring fluorescence. Comparisons were made against a non-targeted IgG-kappa isotype control antibody. No non-specific retention of mAb AN-17 observed in any tissues assessed, with mAb AN-17 becoming largely undetectable after 7 days. Tissues examined included reproductive organs (ovaries, fallopian tubes, uterus) (FIG. 17A); intestine (FIG. 17C); liver (FIG. 17A); kidney (FIG. 17B); spleen (FIG. 17D); lung (FIG. 17B); heart (FIG. 17D); and brain (n=2 animals/group, mean+/−SD) (FIG. 17C).

Figure 18:
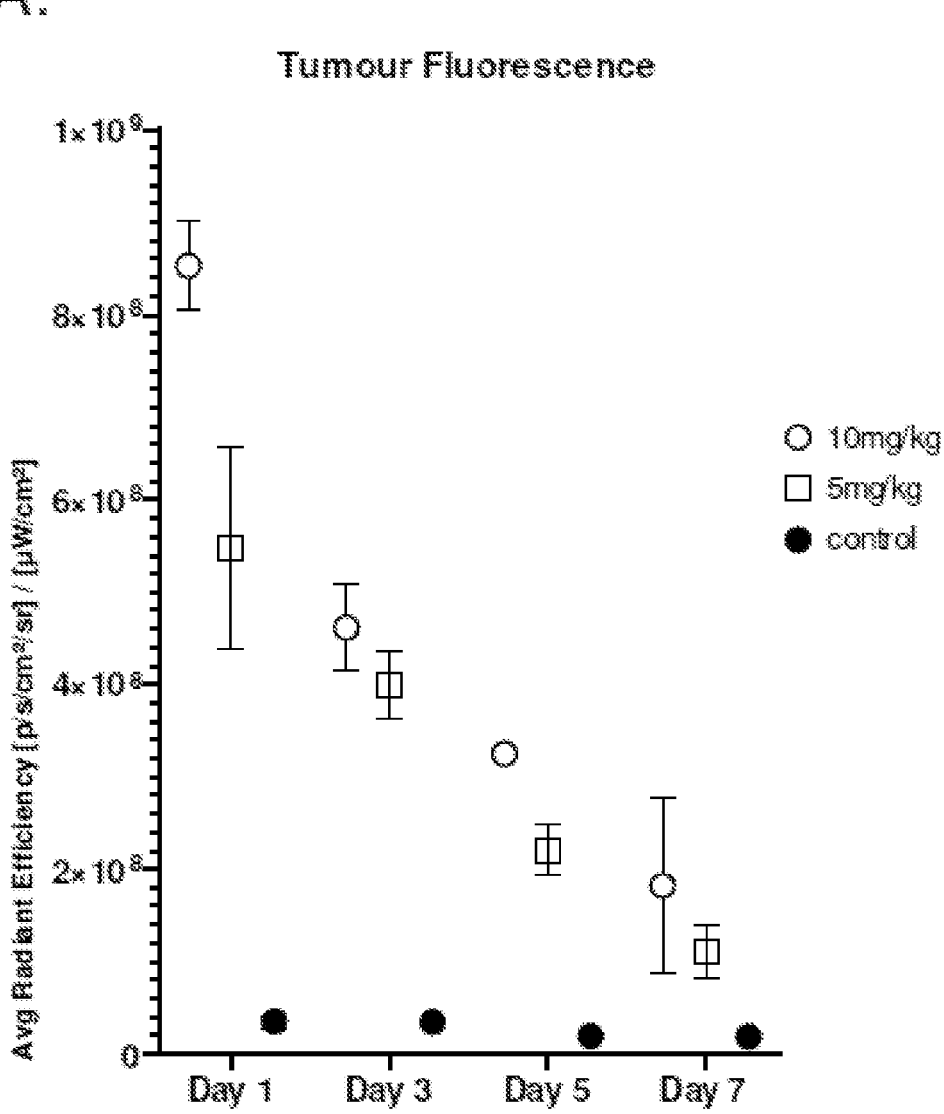
Figure 18:
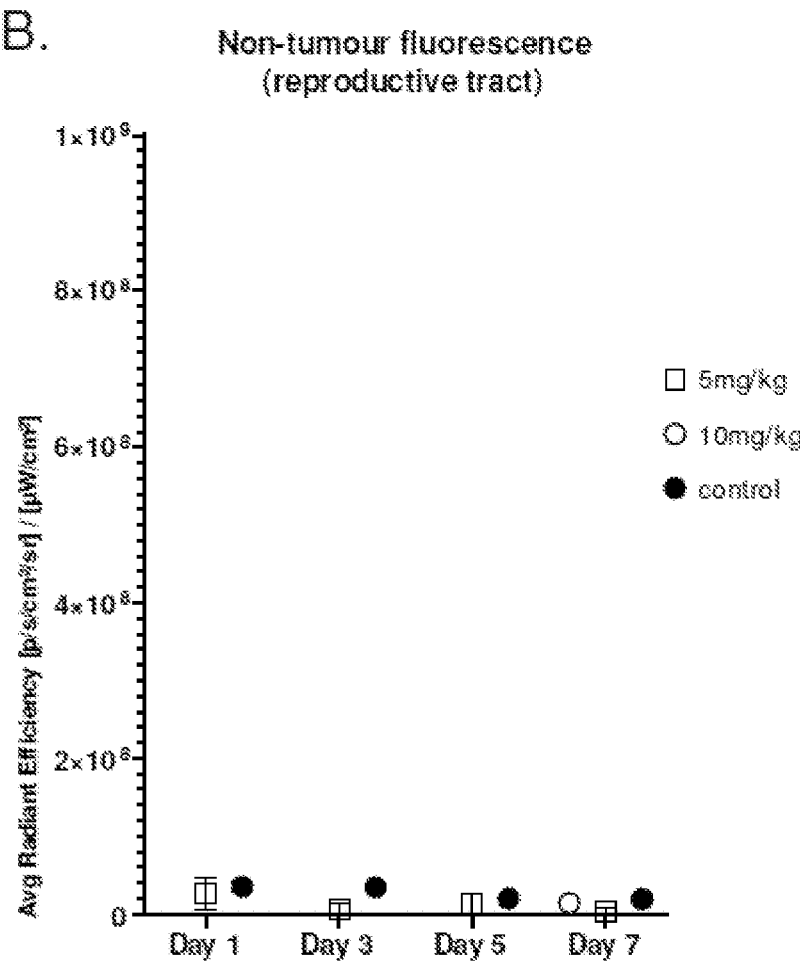
Figure 18:
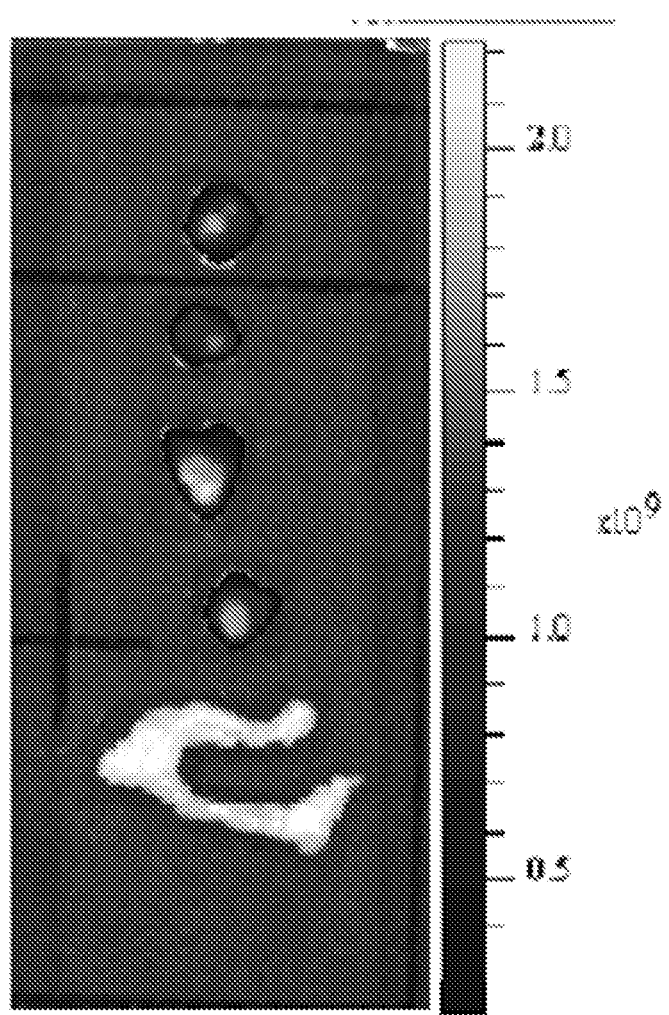

FIGS. 18A-18C shows that mAb AN-17 has high specificity for tumour tissue. Mice (n=2/group/time point) with established primary ovarian tumours were administered doses of either 5 mg/kg or 10 mg/kg mAb AN-17 by intraperitoneal injection. Control animals received isotype-matched control antibody at the same dose. At 1, 3, 5 and 7 days post-administration, mice were culled and antibody localization assessed by fluorescence (as above). Fluorescence was expressed as the average radiant fluorescent intensity per unit tissue area over time. (FIG. 18A) tumour-specific fluorescence signal. (FIG. 18B) non-tumour reproductive tissue fluorescence showing absence of specific signal. (FIG. 18C) image of mAb AN-17 fluorescence (red) in tumours isolated post-mortem, with non-tumour reproductive tissue for comparison (n=2/group/time point; mean+/−SD).

Figure 19:
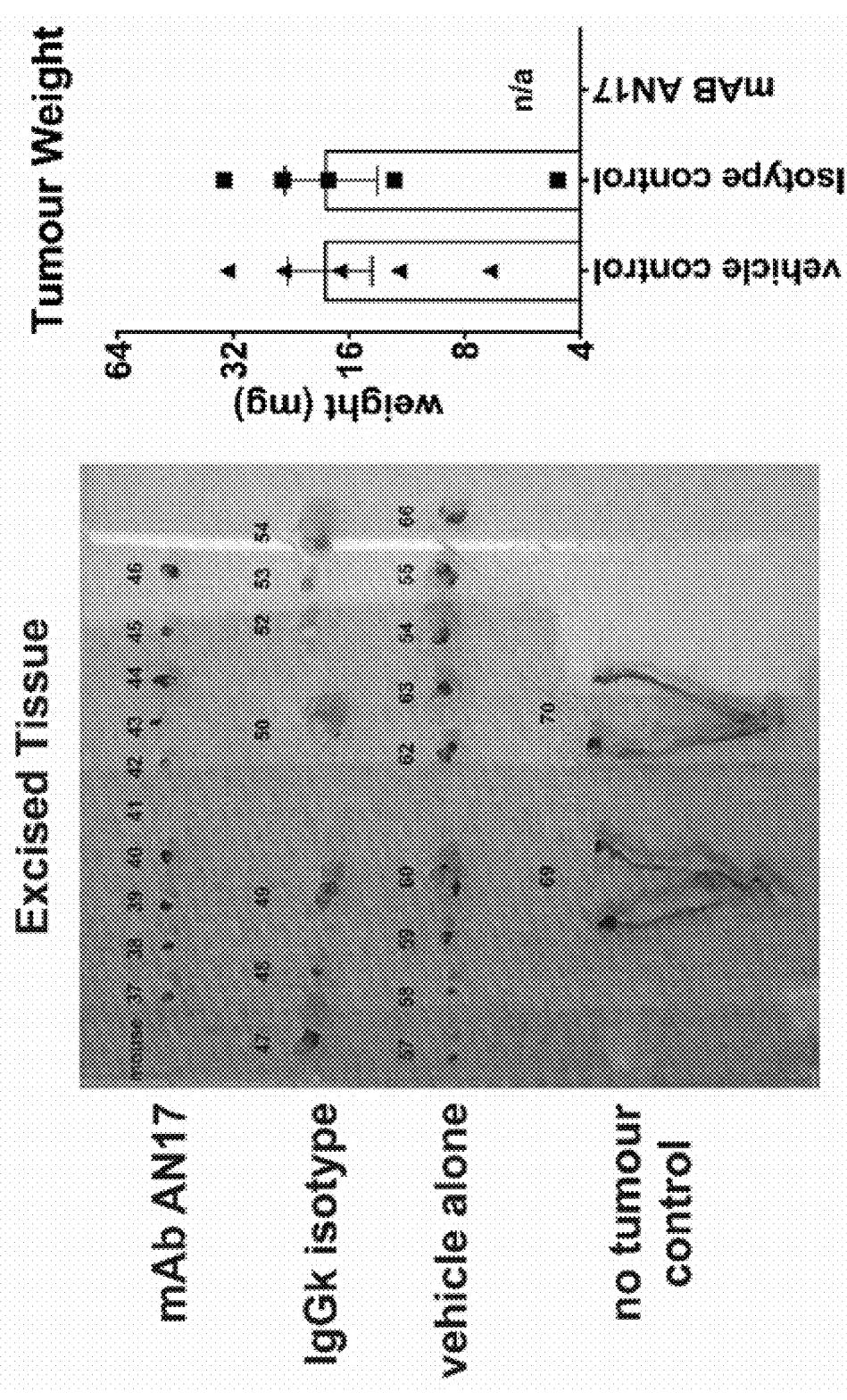
Figure 23A:
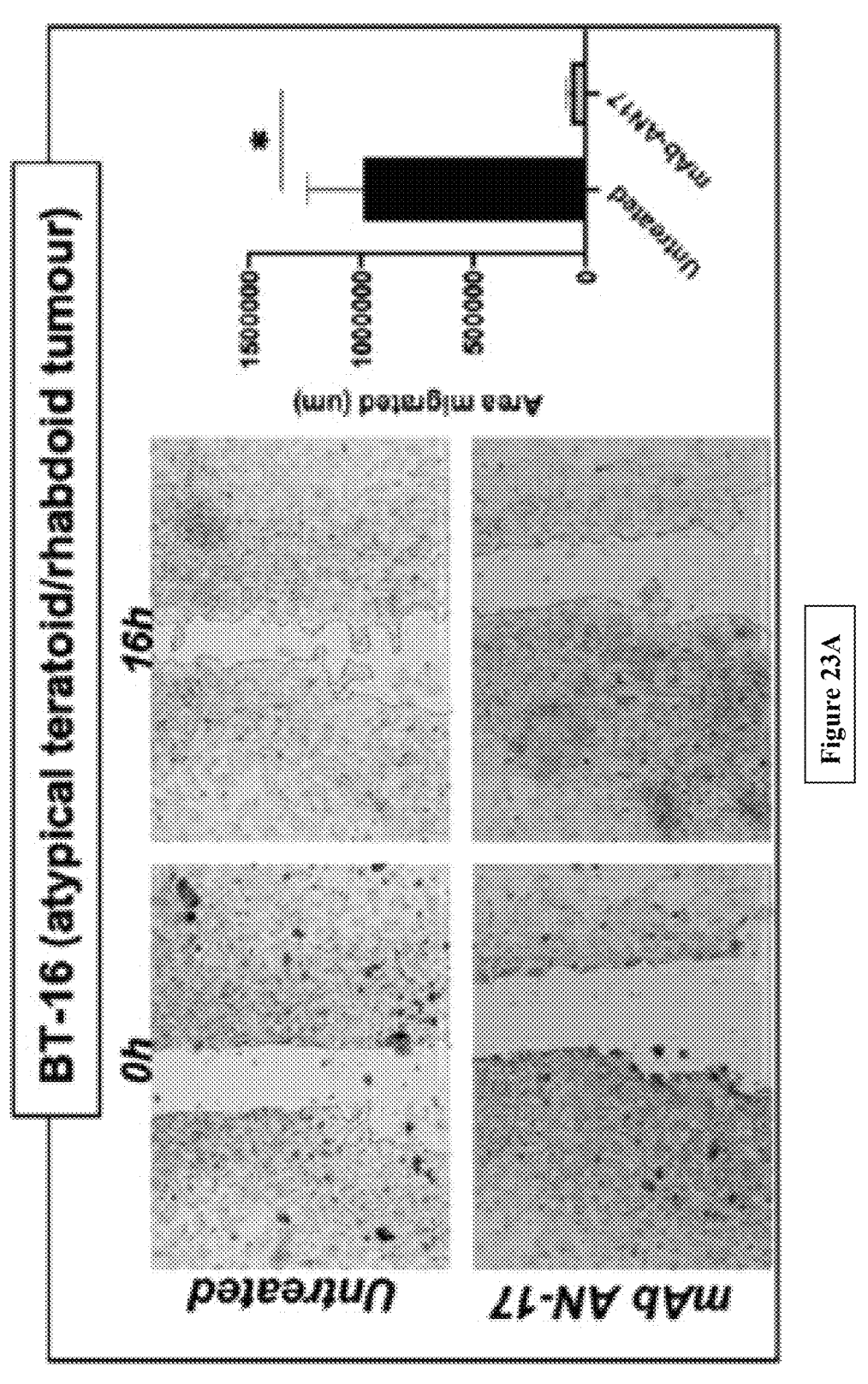
Figure 23B:
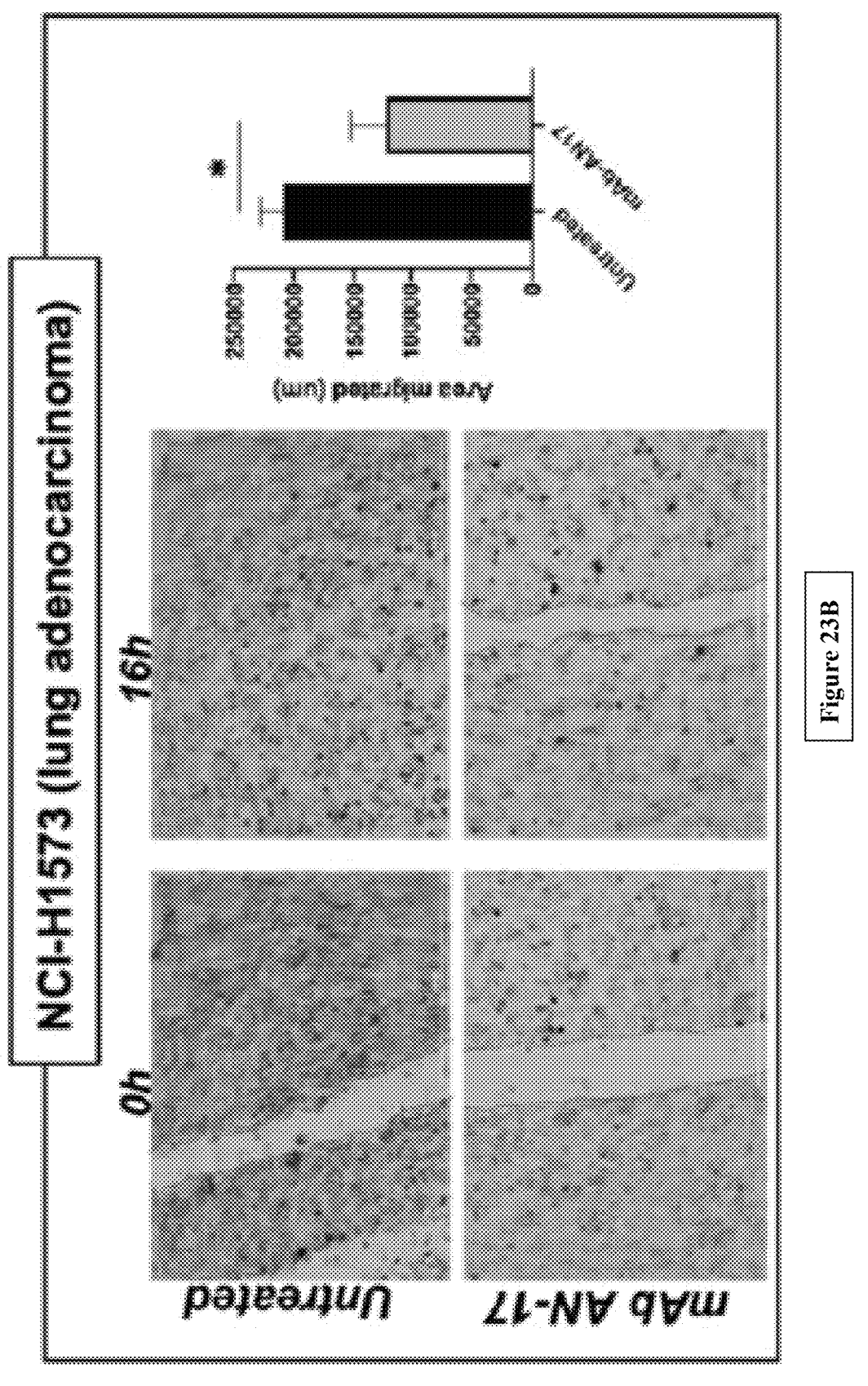
Figure 23C:
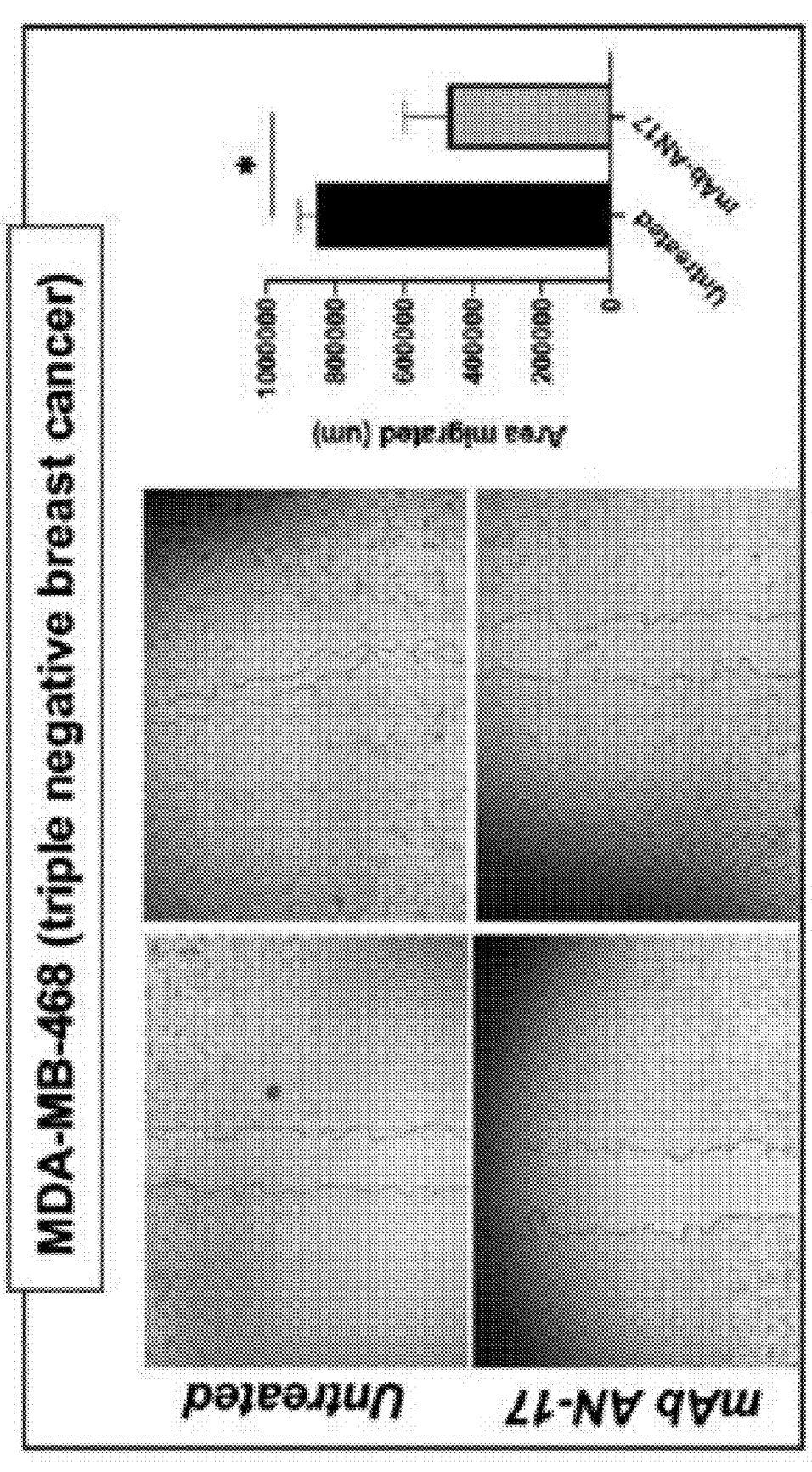
Figure 23D:
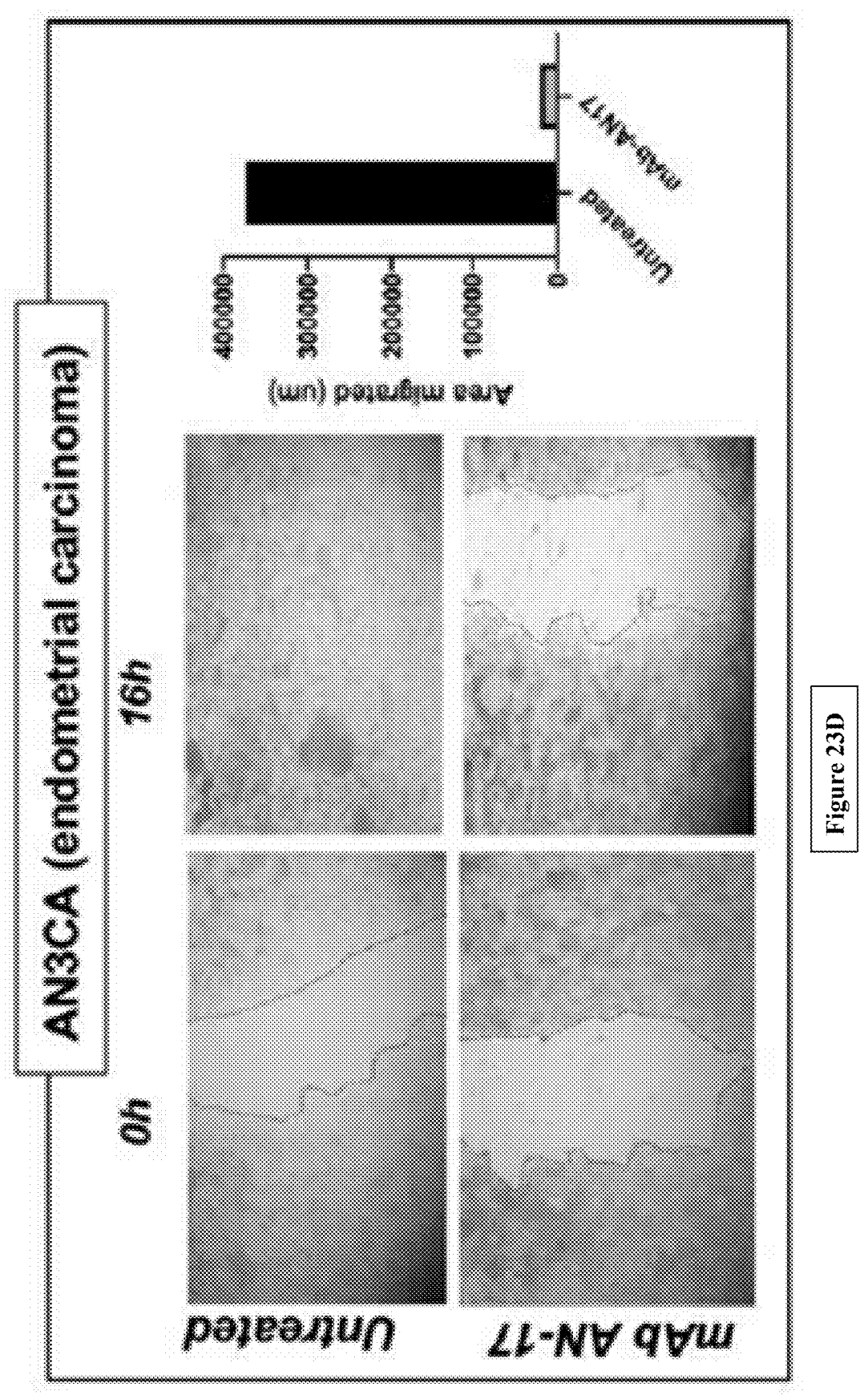
Figure 23E:
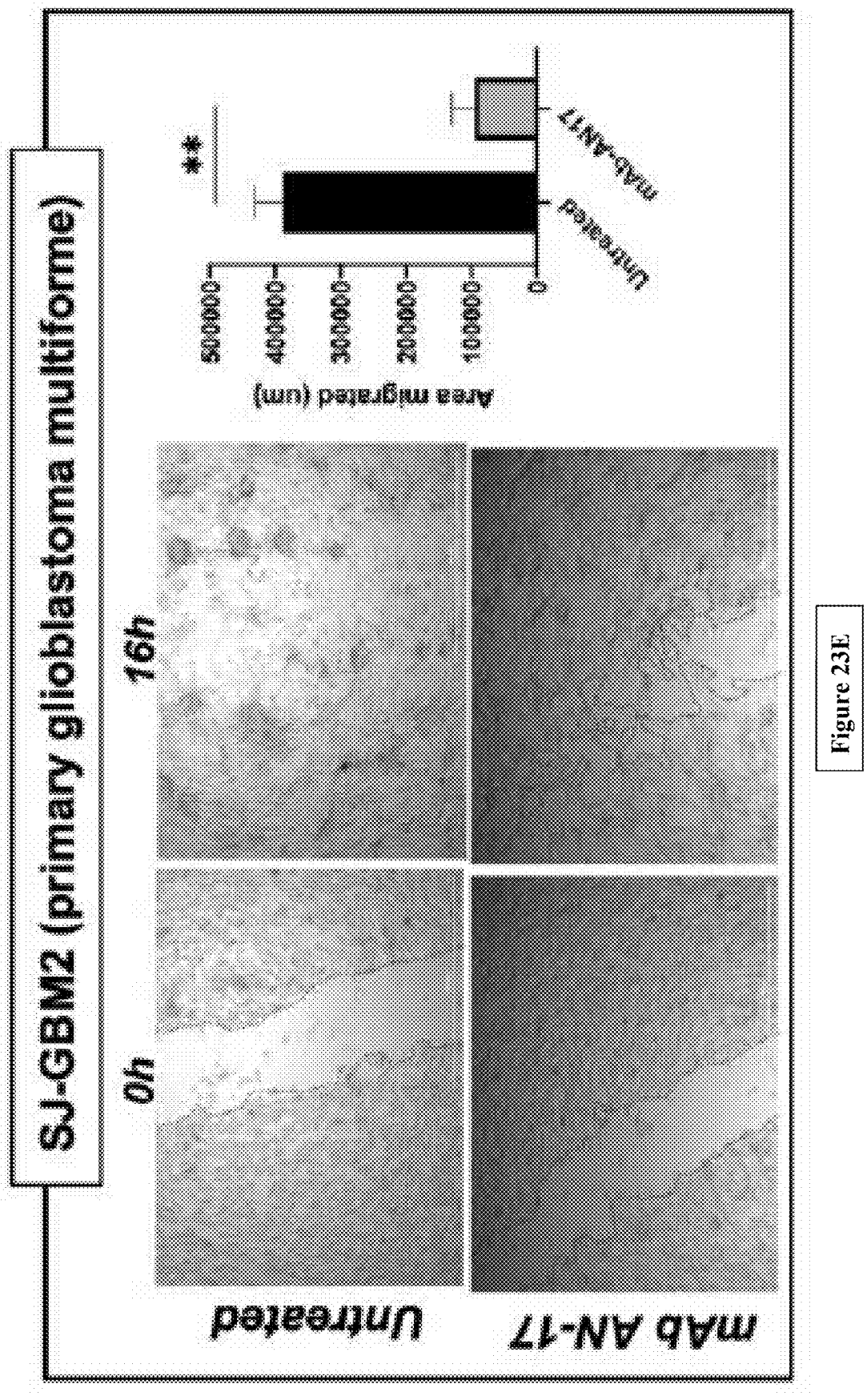
Figure 23F:
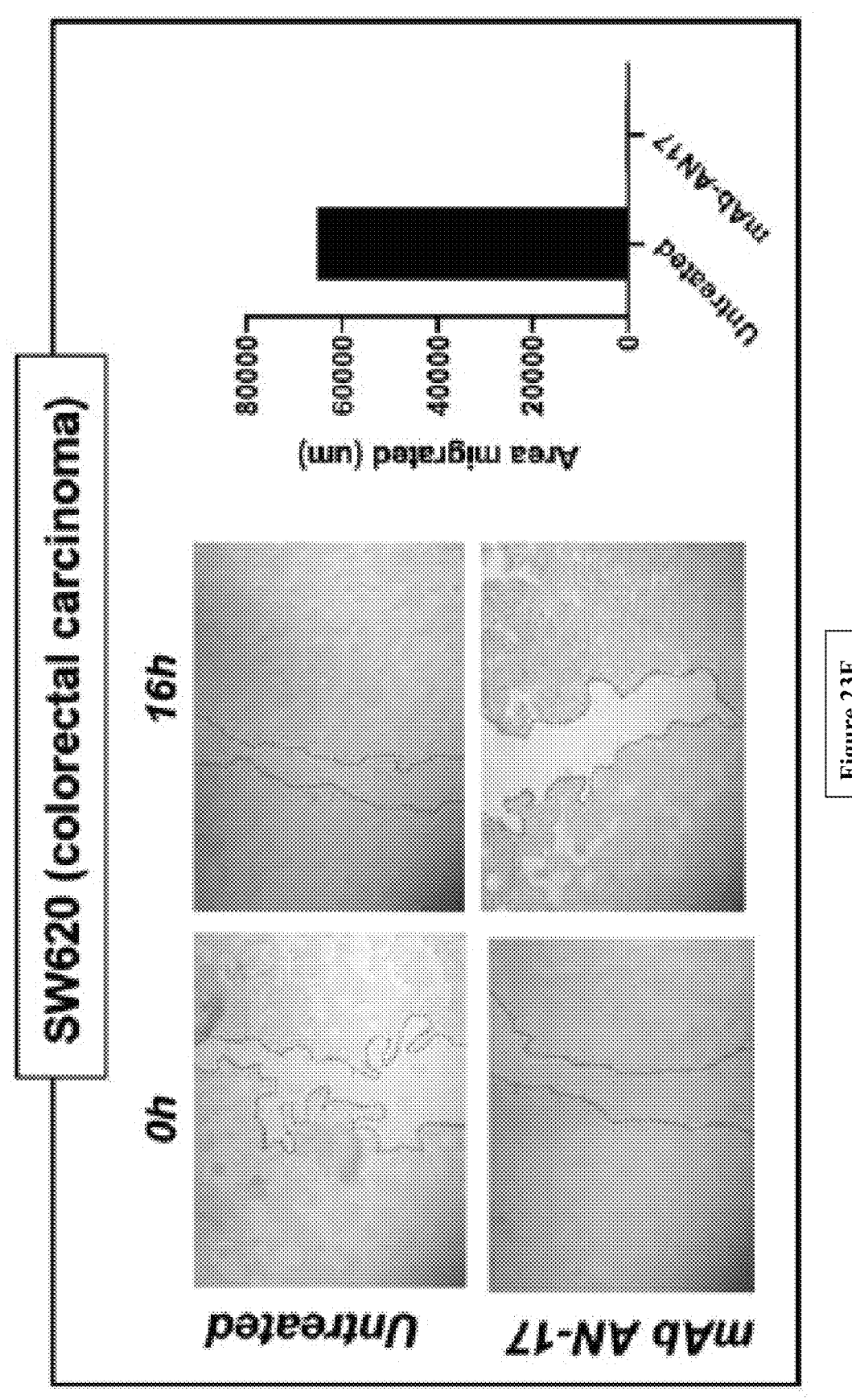

FIG. 19 shows that administration of mAb AN-17 causes direct regression of established tumour mass in mice. Mice (n=10/group) with established primary ovarian tumours were administered mAb AN-17 in bi-weekly 5 mg/kg doses (Mondays and Thursdays) by intraperitoneal injection. Control animals received either isotype-matched control antibody, or PBS vehicle alone. After 3 weeks of continued treatment all animals were culled and examined, and tumour mass measured post mortem. Sixty percent of mice that received either vehicle or isotype control antibody had primary ovarian tumours at cull. By contrast, no tumours could be identified in mice treated with mAb AN-17 (mean+/−SD).

FIG. 20 shows the nucleic acid and amino acid sequences of the heavy chain variable region (VH) and light chain variable region (VL) of the monoclonal antibody AN-17 (from clone AN-17A RG4.E5b.A7.B4) and the % similarity between the VH and VL amino acid sequences of the mAb AN-17 against unrearranged germline mouse antibody sequences (using IMGT/V-Quest program). N/A=non-applicable; nt=nucleotide.

FIG. 21 shows the nucleic acid and amino acid sequences of the VH and VL of mAb AN-17 (SEQ ID NOs: 2 to 5, respectively).

FIGS. 22A-22B show the VH (FIG. 22A) and VL (FIG. 22B) amino acid sequences (SEQ ID NOs: 3 and 5, respectively) of mAb AN-17 annotated by bold and underlined text to highlight the framework regions (FWR; VH FWR1 to 3 SEQ ID NOs: 12 to 15 respectively; VL FWR1 to 3 SEQ ID NOs: 16 to 18 respectively) and the complementarity determining regions (CDR; VH CDR1 to 3 SEQ ID NOs: 6 to 8 respectively; VL CDR1 to 3 SEQ ID NOs: 9 to 11 respectively).

FIGS. 23A-23F show migration of non-ovarian cancer cells (BT16 atypical teratoid rhabdoid (brain) carcinoma (FIG. 23A), NCI-H1573 lung adenocarcinoma (FIG. 23B), SJ-GBM2 primary glioblastoma multiforme (FIG. 23E), AN3CA endometrial carcinoma (FIG. 23D), SW620 colorectal carcinoma (FIG. 23E) and MDA-MB-468 breast carcinoma cell lines (FIG. 23C)) is impaired by mAb AN-17 in vitro.

DETAILED DESCRIPTION

Throughout this specification, unless the context requires otherwise, the word "comprise", or variations such as "comprises" or "comprising", will be understood to imply the inclusion of a stated element or integer or method step or group of elements or integers or method steps but not the exclusion of any other element or integer or method steps or group of elements or integers or method steps.

As used in the subject specification, the singular forms "a", "an" and "the" include plural aspects unless the context clearly dictates otherwise. Thus, for example, reference to "a cancer cell" includes a single cancer cell, as well as two or more cancer cells; reference to "an epitope" includes a single epitope, as well as two or more epitopes; reference to "the disclosure" includes single and multiple aspects taught by the disclosure; and so forth. Aspects taught and enabled herein are encompassed by the term "invention". Any variants and derivatives contemplated herein are encompassed by "forms" of the invention. All aspects of the invention are enabled across the width of the claims.

The present invention is directed to a therapeutic protocol to treat or prevent or otherwise ameliorate the progression of cancer in a mammalian subject. The subject may be male or female. The amelioration of progression includes preventing or reducing cancer cell invasion, migration and/or metastization to thereby treat, prevent or retard development of the cancer or reduce its ability to metastasize. The terms "cancer" and "tumor" are used herein interchangeably.

Hence, enabled herein is a method for the treatment or prophylaxis of cancer in a mammalian subject. The method comprising the administration to the mammalian subject an agent which:

(i) directly targets an extracellular portion of KRT14 on cancer cells or its functional homolog or variant; examples of agents include antibodies, including fragments and derivatives that directly target an extracellular portion of KRT14 and appropriately deimmunized antibodies or other targeting moieties or ligands; or (ii) induces an endogenous agent in vivo which targets an extracellular portion of KRT14 on cancer cells or its functional homolog or variant; examples of endogenous agents include but are not limited to antibodies, T-cells and macrophages.

In either case, the agent or endogenous agent induce cytotoxicity or cytostasis of cancer cells carrying the extracellular portion of KRT14 to thereby prevent or reduce cancer cell invasion, migration and/or metastisization. For example, in relation to (i), an antibody may bind inducing complement-mediated or macrophage- or cytokine-mediated cell lysis or senescence. Alternatively, an antibody or other targeting agent may be conjugated to a cytotoxic molecule or used to prime lymphocytes. Reference to an "antibody" includes a monoclonal antibody, a polyclonal antibody, anti-serum comprising KRT-14 binding antibody and to synthetic or recombinant forms, fragments and derivatives that bind the exogenous portion of KRT14 or part thereof. The medicament, in addition to being an antibody, may be any affinity reagent including but not limited to aptamers, monobodies, anti-calins, DARPins and nanobodies and the like.

In an embodiment, the extracellular portion of human KRT14 is defined by the amino acid sequence (in single letter code):

(SEQ ID NO: 1)
NH₂-GFGGGYGGGLGAGLGGGFGGGFAGGDGL.

Encompassed herein are functional homologs in human or non-human mammals and or variants. In an example, a functional homolog or variant of SEQ ID NO:1 includes a protein comprising an amino acid sequence with at least 80% similarity to SEQ ID NO:1 after optimal alignment. By "at least 80% similarity" includes at least 80, 81, 82, 82, 83, 84, 85, 86, 87, 88, 89, 90, 91, 92, 93, 94, 95, 96, 97, 98, 99 and 100% similarity or identity to SEQ ID NO:1. Such a sequence would be of an extracellular portion of the KRT14 homolog or variant.

Examples of homologs having at least about 80% similarity to SEQ ID NO:1 are shown in Table 3.

TABLE 3

| Uniprot Entry | Gene names (primary) | Protein names | Organism | Identity |
|---|---|---|---|---|
| P02533 | KRT14 | Keratin, type I cytoskeletal 14 (Cytokeratin-14) (CK-14) (Keratin-14) (K14) | *Homo sapiens* (Human) | 100.00% |
| G1RJ14 | KRT14 | Keratin 14 | *Nomascus leucogenys* (Northern white-checked gibbon) (*Hylobates leucogenys*) | 98.90% |
| H2QCZ7 | KRT14 | Uncharacterized protein | *Pan troglodytes* (Chimpanzee) | 98.50% |
| F7H312 | KRT14 | Keratin 14 | *Macaca mulatta* (*Rhesus macaque*) | 98.50% |
| A0A0D9S2F0 | KRT14 | Keratin 14 | *Chlorocebus sabaeus* (Green monkey) (*Cercopithecus sabaeus*) | 98.10% |
| H2NVQ7 | KRT14 | Keratin 14 | *Pongo abelli* (Sumatran orangutan) (*Pongo pygmaeus abelii*) | 98.10% |
| A0A096P5N3 | KRT14 | Keratin 14 | *Papio anubis* (Olive baboon) | 98.10% |
| G7NII8 | | Cytokeratin-14 | *Macaca mulatta* (*Rhesus macaque*) | 97.20% |
| L9K0I1 | | Keratin, type I cytoskeletal 14 | *Tupaia chinensis* (Chinese tree shrew) | 96.30% |
| F7ATL5 | KRT14 | Keratin 14 | *Equus caballus* (Horse) | 95.80% |
| G3QRG7 | KRT14 | Keratin 14 | *Gorilla gorilla gorilla* (Western lowland gorilla) | 95.40% |
| M3WGY4 | KRT14 | Keratin 14 | *Felis catus* (Cat) (*Felis silvestris catus*) | 93.70% |
| A0A287AEL2 | KRTI4 | Keratin 14 | *Sus scrofa* (Pig) | 92.50% |
| A0A1U7R4L9 | Krt14 | keratin, type I cytoskeletal 14 | *Mesocricetus auratus* (Golden hamster) | 92.30% |
| A0A1S3AIS0 | LOC103124740 | keratin, type I cytoskeletal 14 | *Erinaceus europaeus* (Western European hedgehog) | 92.20% |
| H0X4W1 | KRT14 | Keratin 14 | *Otolemur garnettii* (Small-eared galago) (Garnett's greater bushbaby) | 91.90% |
| A0A1S3GYN5 | Krt14 | keratin, type I cytoskeletal 14 | *Dipodomys ordii* (Ord's kangaroo rat) | 91.60% |
| F1Q0R0 | KRT14 | Keratin 14 | *Canis lupus familiaris* (Dog) (*Canis familiaris*) | 91.60% |
| G1T1Y7 | KRT14 | Keratin 14 | *Oryctolagus cuniculus* (Rabbit) | 91.50% |
| L8HP74 | | Keratin, type 1 cytoskeletal 14 | *Bos mutus* (wild yak) | 91.50% |
| G1LFZ4 | KRT14 | Keratin 14 | *Ailuropoda melanoleuca* (Giant panda) | 91.40% |
| S9XAP9 | | Keratin, type 1 cytoskeletal 14-like protein | *Camelus ferus* (Wild bactrian camel) (*Camelus bactrianus ferus*) | 91.40% |

TABLE 3-continued

| Uniprot Entry | Gene names (primary) | Protein names | Organism | Identity |
|---|---|---|---|---|
| A0A1U7UN37 | KRT14 | keratin, type I cytoskeletal 14 | *Tarsius syrichta* (Philippine tarsier) | 91.20% |
| F1MC11 | KRT14 | Keratin, type I cytoskeletal 14 | *Bos taurus* (Bovine) | 91.10% |
| M3YHM3 | KRT14 | Keratin 14 | *Mustela putorius furo* (European domestic ferret) (*Mustela furo*) | 91.00% |
| G3I8F9 | | Keratin, type I cytoskeletal 14 | *Cricetulus griseus* (Chinese hamster) (*Cricetulus barabensis griseus*) | 89.80% |
| Q61781 | Krt14 | Keratin, type I cytoskeletal 14 (Cytokeratin-14) (CK-14) (Keratin-14) (K14) | *Mus musculus* (Mouse) | 89.00% |
| G3T6A4 | KRT14 | Keratin 14 | *Loxodonta africana* (African elephant) | 88.20% |
| A0A286XN126 | KRT14 | Keratin 14 | *Cavia porcellus* (Guinea pig) | 87.80% |
| S7PB95 | cytoskeletal 14 | Keratin, type I | *Myotis brandtii* (Brandt's bat) | 87.30% |
| W5Q6L8 | KRT14 | Keratin 14 | *Ovis aries* (Sheep) | 86.70% |
| Q6IFV1 | Krt14 | Keratin, type I cytoskeletal 14 (Cytokeratin-14) (CK-14) (Keratin-14) (K14) (Type I keratin Ka14) | *Rattus norvegicus* (Rat) | 86.30% |
| G1PTI6 | KRT14 | Keratin 14 | *Myotis lucifugus* (Little brown bat) | 86.00% |
| G5B0M6 | | Keratin, type I cytoskeletal 14 | *Heterocephalus glaber* (Naked mole rat) | 84.80% |
| F7A610 | KRT14 | Keratin 14 | *Macaca mulatta* (Rhesus macaque) | 84.00% |
| A0A091DDD7 | | Keratin, type I cytoskeletal 14 | *Fukomys damarensis* (Damaraland mole rat) (*Cryptomys damarensis*) | 82.50% |
| A0A287BSX6 | KRT14 | Keratin 14 | *Sus scrofa* (Pig) | 82.20% |
| A0A1D5QHL9 | KRT14 | Keratin 14 | *Macaca mulatta* (Rhesus macaque) | 81.40% |
| A0A287AK58 | KRT14 | Keratin 14 | *Sus scrofa* (Pig) | 81.10% |
| A0A287AXN9 | KRT14 | Keratin 14 | *Sus scrofa* (Pig) | 81.00% |

The term "similarity" as used herein includes exact identity between compared sequences at the amino acid level. Where there is non-identity at the amino acid level, "similarity" includes amino acids that are nevertheless related to each other at the structural, functional, biochemical and/or conformational levels. In an embodiment, amino acid and sequence comparisons are made at the level of identity rather than similarity.

Terms used to describe sequence relationships between two or more polypeptides include "reference sequence", "comparison window", "sequence similarity", "sequence identity", "percentage of sequence similarity", "percentage of sequence identity", "substantially similar" and "substantial identity". A "reference sequence" is from 5 to 20 amino acids in length. A "comparison window" refers to a conceptual segment of typically 5-20 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e. resulting in the highest percentage homology over the comparison window) generated by any of the various methods selected. Reference also may be made to the BLAST family of programs as for example disclosed by Altschul et al. (1997) *Nucl. Acids. Res.* 25:3389. A detailed discussion of sequence analysis can be found in Unit 19.3 of Ausubel et al. (1994-1998) *In: Current Protocols in Molecular Biology*, John Wiley & Sons Inc.

The terms "sequence similarity" and "sequence identity" as used herein refers to the extent that sequences are identical or functionally or structurally similar on an amino acid-by-amino acid basis over a window of comparison. Thus, a "percentage of sequence identity", for example, is calculated by comparing two optimally aligned sequences over the window of comparison, determining the number of positions at which the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e. the window size), and multiplying the result by 100 to yield the percentage of sequence identity.

The terms "variant" and "derivative" refer, therefore, to an amino acid sequence displaying substantial sequence identify or similarity with a reference amino acid sequence (i.e. SEQ ID NO:1 or subsequence thereof). The terms "variant" and "derivatives" also includes naturally-occurring allelic variants.

A "derivative" also includes a mutant, fragment, part, portion or hybrid molecule with reference to SEQ ID NO:1 or its functional homolog. A derivative generally but not exclusively carries a single or multiple amino acid substitution, addition and/or deletion.

A "homolog" includes an analogous polypeptide having at least about 80% similar amino acid sequence from another animal species or from a different locus within the same species.

A variant also includes an "analog" which is generally a chemical analog. Chemical analogs of SEQ ID NO:1 contemplated herein include, but are not limited to, modification to side chains, incorporation of unnatural amino acids and/or their derivatives during peptide, polypeptide or protein synthesis and the use of crosslinkers and other methods which impose conformational constraints on the proteinaceous molecule or their analogs.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

Such analogs may be useful in synthetic vaccines or to generate antibodies for use as targeting agents. Analogs may have attributes such as increased serum half-life. The antibodies may also be in anti-sera which comprise KRT14-binding antibodies.

Taught herein is a method for the treatment or prophylaxis of cancer in a mammalian subject, the method comprising administering to the subject, an amount of an agent which targets an extracellular portion of KRT14 or its functional homolog or variant resident on cancer cells or an agent which induces in vivo production of an antagonist of the extracellular portion of KRT14 or its functional homolog or variant on cancer cells, the amount effective to prevent or reduce cancer cell invasion, migration and/or metastisization.

Enabled herein is method for the treatment or prophylaxis of cancer in a mammalian subject, the method comprising administering to the subject, an amount of an agent which targets an extracellular portion defined by the amino acid sequence set forth in SEQ ID NO:1 or an amino acid sequence having at least about 80% similarity to SEQ ID NO:1 after optimal alignment or its functional homolog or variant thereof resident on cancer cells or an agent which induces in vivo production of an antagonist of the extracellular portion of KRT14 or its functional homolog or variant on cancer cells, the amount effective to prevent or reduce cancer cell invasion, migration and/or metastisization.

Further taught herein is method for the treatment or prophylaxis of cancer in a mammalian subject, the method comprising administering to the subject, an amount of an agent which targets an extracellular portion defined by the amino acid sequence set forth in SEQ ID NO:1 or a functional homolog or variant thereof resident on cancer cells or an agent which induces in vivo production of an antagonist of the extracellular portion of KRT14 on cancer cells or its functional homolog or variant on cancer cells by the amount effective to prevent or reduce cancer cell invasion, migration and/or metastisization.

Still further enabled is a method for the treatment of ovarian cancer in a human subject, the method comprising administering to the subject, an amount of an antibody which targets an extracellular portion of KRT14 defined by SEQ ID NO:1 resident on ovarian cancer cells, the amount effective to prevent or reduce ovarian cancer cell invasions, migration and/or metastisization. The medicament, in addition to being an antibody, may be any affinity reagent including but not limited to aptamers, monobodies, anticalins, DARPins and nanobodies and the like.

The term "administering to the subject" includes contacting the cancer cell by any means to bring into contact the agent and the extracellular portion of KRT14 on the cancer cell. The mammalian subject may be male or female and of any age.

Identified herein is a short epitope of the KRT14 protein exposed at the cell surface, and is available for interaction with exogenously added agents or specifically induced endogenous molecules. Targeting this region using an antibody or other targeting agent that recognizes the exposed sequence can completely prevent cancer cell invasion in vitro, mimicking the effects of KRT14 gene ablation. These data indicate that KRT14 represents a previously unrecognized and highly specific target on tumor cells for directed antagonist therapy.

Also observed is failure to form a solid tumor in mice. Implanted cancer cells lacking functional KRT14 gene become undetectable after several weeks. This indicates that these cancer cells are removed from the animal, likely through, for example, immune-mediated clearance. Thus, it is proposed herein that the use of an anti-KRT14 therapy can promote tumor stabilization (through impaired implantation/invasion), and tumor regression. Targeted anti-KRT14 therapy has high potential for cancer treatment, for the following reasons:

(i) anti-KRT14 therapy is expected to be non-toxic, since KRT14 is not widely expressed and an antagonist is selected to be non-toxic to cells;

ii) anti-KRT14 therapy is applicable to all stages of disease, to target both primary and metastatic deposits;

iii) KRT14-expressing cells are specifically enriched over time and in response to chemotherapy; thus, anti-KRT14 therapy would be highly applicable to patients who have developed recurrent, chemoresistant disease and have no further conventional treatment options available;

iv) anti-KRT14 therapy can potentially promote regression of tumors, in addition to stabilizing existing disease.

There are also several additional applications for ani-KRT14 therapies including:

i) conjugation to a cytotoxic "payload" for directed therapy against the invasive cancer stem cell population;

ii) use in CAR-T therapies, designed to direct anti-tumor cytotoxic T-cells to destroy the tumor-initiating cell population;

iii) therapeutic or preventative vaccination;

iv) generation of "de-humanized" antibody production in veterinary applications;

v) theranostic applications, for example, to predict therapeutic response/chemoresistence/tumor recurrence or progression.

KRT14-dependent tumor progression has also been identified as a key mechanism involved in several other solid tumor types, and likely represents a conserved mechanism underlying tumor spread. Thus, anti-KRT14 therapy has applications well beyond ovarian cancers and may prove applicable to the treatment of a wide range of solid tumor. As used herein a "cancer" refers to a group of diseases and disorders that are characterized by uncontrolled cellular growth (e.g., formation of tumor) without any differentiation of those cells into specialized and different cells. Cancers contemplated for treatment herein include, without being limited to, and in addition to a gynecological condition such as ovarian cancer, ABL1 protooncogene, AIDS related cancers, acoustic neuroma, acute lymphocytic leukaemia, acute myeloid leukaemia, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (Skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukaemia, childhood soft tissue sarcoma, chondrosarcoma, choriocarcinoma, chronic lymphocytic leukaemia, chronic myeloid leukaemia, colorectal cancers, cutaneous T-cell lymphoma, dermatofibrosarcoma-protuberans, desmoplastic-small-round-cell-tumor, ductal carcinoma, endocrine cancers, endometrial cancer, ependymoma, esophageal cancer, Ewing's sarcoma, extra-hepatic bile duct cancer, eye cancer, melanoma, retinoblastoma, fallopian tube cancer, Fanconi anaemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynecological cancers, haematological malignancies, hairy cell leukaemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's-cell-histiocytosis, laryngeal cancer, leiomyosarcoma, leukaemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid-tumor-of-kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, Nijmegen breakage syndrome, non-melanoma skin cancer, non-small-cell-lung-cancer-(NSCLC), ocular cancers, oesophageal cancer, oral cavity cancer, oropharynx cancer, osteosarcoma, pancreas cancer, paranasal cancer, parathyroid cancer, parotid gland cancer, penile cancer, peripheralneuroectodermal-tumors, pituitary cancer, polycythemia vera, prostate cancer, rare-cancers-and-associated-disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's-macroglobulinemia and Wilms' tumor. Endometrial and colorectal cancers may also be treated. These cancers may affect male or female subjects and either may be treated in accordance with the present invention.

In an embodiment, the cancer is a gynecological cancer. In an embodiment, the gynecological cancer is ovarian cancer or a stage or form of ovarian cancer. Alternatively, the cancer is, inter alia, a cancer of the liver, bladder, lung, colon, gastrointestinal tract, bowel, pancreas and/or throat amongst other cancer in a male or female subject. The present invention extends to combination therapy where the agent targeting KRT14 or the agent inducing an in vivo KRT14 antagonist is given with another anti-cancer agent and/or radiation therapy and/or surgical intervention. In an embodiment, the methods disclosed herein further comprise administering to the subject an additional anti-cancer agent and/or exposing the patient to immunotherapy, radiation therapy and/or surgical intervention. Illustrative examples of additional anti-cancer agents include a chemotherapeutic agent such as one or more of dactinomycin, daunorubicin, doxorubicin (adriamycin), idarubicin and mitoxantrone, or platinum based agents or an antimetabolite. Antimetabolites are substances that interfere with the body's chemical processes, such as creating proteins, DNA, and other chemicals needed for cell growth and reproduction; in cancer treatment, antimetabolite drugs disrupt DNA production, which in turn prevents cell division. Examples include azaserine, D-cycloserine, nycophenolic acid, trimethoprim, 5-fluorouracil, capecitabine, methotrexate, gemcitabine, cytarabine (ara-C) and fludarabine. Other immune reagents may be administered such as primed T-cells and cytokines. Combination therapy may be provided simultaneously or sequentially in either order and within seconds, minutes, hours, days or weeks of each other. In an embodiment, the additional anti-cancer agent is selected from the group consisting of dactinomycin, daunorubicin, doxorubicin (adriamycin), idarubicin and mitoxantrone, a platinum based agent, an antimetabolite, primed T-cells and cytokines. In an embodiment, the an antimetabolite is selected from the group consisting of azaserine, D-cycloserine, nycophenolic acid, trimethoprim, 5-fluorouracil, capecitabine, methotrexate, gemcitabine, cytarabine (ara-C) and fludarabine.

In an embodiment, the mammalian subject is a human. For a gynecological cancer, the subject is a human female. However, for all other cancers, the subject may be a human male or female.

Accordingly, taught herein is a method for the treatment or prophylaxis of cancer in a human subject, the method comprising administering to the subject, an amount of an agent which targets an extracellular portion of KRT14 or its functional homolog or variant resident on cancer cells or an agent which induces in vitro production of an antagonist of the extracellular portion of KRT14 or its functional homolog or variant on cancer cells, the amount effective to prevent or reduce cancer cell invasion, migration and/or metastisization.

Enabled herein is method for the treatment or prophylaxis of cancer in a human subject, the method comprising administering to the subject, an amount of an agent which targets an extracellular portion defined by the amino acid sequence set forth in SEQ ID NO:1 or a functional homolog or variant thereof resident on cancer cells or an agent which induces production of an antagonist of the extracellular portion of KRT14 on cancer cells or its functional homolog or variant by said subject, the amount effective to prevent or reduce cancer cell invasion, migration and/or metastisization.

Further taught herein is method for the treatment or prophylaxis of cancer in a human subject, the method comprising administering to the subject, an amount of an agent which targets an extracellular portion defined by the amino acid sequence set forth in SEQ ID NO:1 or an amino acid sequence having at least about 80% similarity to SEQ ID NO:1 after optimal alignment or its functional homolog or variant thereof resident on cancer cells or an agent which induces in vivo production of an antagonist of the extracellular portion of KRT14 on cancer cells or its functional homolog or variant, the amount effective to prevent or reduce cancer cell invasion, migration and/or metastisization.

In an embodiment, the cancer is ovarian cancer and the subject is a human female subject.

Accordingly, taught herein is a method for the treatment or prophylaxis of ovarian cancer in a human female subject, the method comprising administering to the subject, an amount of an agent which targets an extracellular portion of KRT14 or its functional homolog or variant resident on cancer cells or an agent which induces in vitro production of an antagonist of the extracellular portion of KRT14 or its functional homolog or variant on cancer cells, the amount effective to prevent or reduce cancer cell invasion, migration and/or metastisization.

Enabled herein is method for the treatment or prophylaxis of ovarian cancer in a human female subject, the method comprising administering to the subject, an amount of an agent which targets an extracellular portion defined by the amino acid sequence set forth in SEQ ID NO:1 or a functional homolog or variant thereof resident on cancer cells or an agent which induces production of an antagonist of the extracellular portion of KRT14 on cancer cells or its functional homolog or variant by said subject, the amount effective to prevent or reduce cancer cell invasion, migration and/or metastisization.

Further taught herein is method for the treatment or prophylaxis of ovarian cancer in a human female subject, the method comprising administering to the subject, an amount of an agent which targets an extracellular portion defined by the amino acid sequence set forth in SEQ ID NO:1 or an amino acid sequence having at least about 80% similarity to SEQ ID NO:1 after optimal alignment or its functional homolog or variant thereof resident on cancer cells or an agent which induces in vivo production of an antagonist of the extracellular portion of KRT14 on cancer cells or its functional homolog or variant, the amount effective to prevent or reduce cancer cell invasion, migration and/or metastisization.

The present invention also has veterinary application such as the treatment of cancer in companion animals (e.g., dogs and cats) or other non-human animals such as farm animals (e.g., equine animals, pigs, sheep, cattle, goats, llamas and alpacas), laboratory test animals (e.g., mice, rabbits, guinea pigs, hamsters) and wild captive animals (e.g., the Tasmanian-devil). Other animals contemplated for treatment include Gibbon monkeys, Chimpanzees, Rhesus macaques, Green monkeys, Orangutans, baboons, shrews, gorillas, hedgehogs, bushbabies, kangaroo rats, wild yaks, Philippine tarsiers, ferrets, elephants and bats. In relation to equine animals, these include horses, Przewalski horses, zebras and asses. In relation to horses, these include a Thoroughbred horse, Warmblood horse, Quarter horse and a Standard horse as well as an equestrian horse and a performance horse.

Accordingly, taught herein is a method for the treatment or prophylaxis of cancer in a non-human mammalian subject, the method comprising administering to the subject, an amount of an agent which targets an extracellular portion of KRT14 or its functional homolog or variant resident on cancer cells or an agent which induces in vivo production of an antagonist of the extracellular portion of KRT14 on cancer cells or its functional homolog or variant, the amount effective to prevent or reduce cancer cell invasion, migration and/or metastisization.

Further taught herein is method for the treatment or prophylaxis of cancer in a non-human mammalian subject, the method comprising administering to the subject, an amount of an agent which targets an extracellular portion defined by the amino acid sequence set forth in SEQ ID NO:1 or an amino acid sequence having at least about 80% similarity to SEQ ID NO:1 after optimal alignment or its functional homolog or variant thereof resident on cancer cells or an agent which induces in vivo production of an antagonist of the extracellular portion of KRT14 on cancer cells or its functional homolog or variant by said subject, the amount effective to prevent or reduce cancer cell invasion, migration and/or metastisization.

Enabled herein is method for the treatment or prophylaxis of cancer in a non-human mammalian subject, the method comprising administering to the subject, an amount of an agent which targets an extracellular portion defined by the amino acid sequence set forth in SEQ ID NO:1 or a functional homolog or variant thereof resident on cancer cells or an agent which induces in vivo production of an antagonist of the extracellular portion of KRT14 on cancer cells or its functional homolog or variant on cancer cells, the amount effective to prevent or reduce cancer cell invasion, migration and/or metastisization.

The non-human mammalian subject may be male or female. In an embodiment, the agent is an antibody. The antibody may be a human-derived antibody or a deimmunized antibody or a mammalianized antibody suitable for a particular mammalian subject. For example, a mouse antibody may be humanized for use in humans. Hence, the antibody may be generated in a species of mammal for use in that mammal or may be mammalianized or deimmunized as appropriate. For the avoidance of doubt, the "antibody" may be a polyclonal or monoclonal antibody or anti-sera comprising KRT14-binding antibodies or KRT14-binding variants or derivatives or fragments of these antibodies or synthetic or recombinant forms, including F' (ab) binding fragments. The medicament, in addition to being an antibody, may be any affinity reagent including but not limited to aptamers, monobodies, anti-calins, DARPins and nanobodies and the like.

Hence, the present invention further provides therefore the application of biochemical techniques to render an antibody derived from one animal substantially non-immunogenic in another animal of the same or different species. The biochemical process is referred to herein as "deimmunization". Reference herein to "deimmunization" includes processes such as complementary determinant region (CDR) grafting, "reshaping" with respect to a framework region of an immunointeractive molecule and variable (v) region mutation, all aimed at reducing the immunogenicity of an immunointeractive molecule (e.g., antibody) in a particular host (e.g., a human subject). In an embodiment, the preferred immunointeractive molecule is an antibody such as a polyclonal or monoclonal antibody specific for a cancer cell carrying an extracellular portion of KRT14. In an embodiment, the immunointeractive molecule is a monoclonal antibody, derived from one animal and which exhibits reduced immunogenicity in another animal from the same or different species such as but not limited to humans.

Reference to "substantially non-immunogenic" includes reduced immunogenicity compared to a parent antibody, i.e., an antibody before exposure to deimmunization processes. The term "immunogenicity" includes an ability to provoke, induce or otherwise facilitate a humoral and/or T-cell mediated response in a host animal. Convenient immunogenic criteria include the ability for amino acid sequences derived from a variable (v) region of an antibody to interact with MHC class II molecules thereby stimulating or facilitating a T-cell mediating response including a T-cell-assisted humoral response.

By "antibody" is meant a protein of the immunoglobulin family that is capable of combining, interacting or otherwise associating with an antigen. An antibody is, therefore, an antigen-binding molecule. An "antibody" is an example of an immunointeractive molecule and includes a polyclonal or monoclonal antibody or anti-sera. In an embodiment, the immunointeractive molecules of the present invention are monoclonal antibodies.

The term "antigen" is used herein in its broadest sense to refer to a substance that is capable of reacting in and/or inducing an immune response. Reference to an "antigen" includes an antigenic determinant or epitope or a cancer cell as defined by SEQ ID NO:1 or its functional homolog or variant.

By "antigen-binding molecule" is meant any molecule that has binding affinity for a target antigen (i.e., SEQ ID NO:1). It will be understood that this term extends to immunoglobulins (e.g., polyclonal or monoclonal antibodies), immunoglobulin fragments and non-immunoglobulin derived protein frameworks that exhibit antigen-binding activity. The terms "antibody" and "antigen-binding molecules" include deimmunized forms of these molecules.

By "antigenic determinant" or "epitope" is meant that part of KRT14 which has an extracellular domain to which an immune response can be directed.

Although antibodies of the present invention are typically deimmunized forms of murine monoclonal antibodies for use in humans, the subject invention extends to antibodies from any source and deimmunized for use in any host. Examples of animal sources and hosts include humans, primates, livestock animals (e.g., sheep, cows, horses, pigs, donkeys), laboratory test animals (e.g., mice, rabbits, guinea pigs, hamsters) and companion animals (e.g., dogs, cats).

Immunization and subsequent production of monoclonal antibodies can be carried out using standard protocols as for example described by Kohler and Milstein (Kohler et al. (1975) *Nature* 256:495-499 and Kohler et al. (1976) *Eur. J. Immunol.* 6(7):511-519; Coligan et al. *Current Protocols in Immunology,* 1991-1997 or Toyama et al. (1987) *Monoclonal Antibody, Experiment Manual,* published by Kodansha Scientific). Essentially, an animal is immunized with an antigen (i.e., a protein or protein analog comprising SEQ ID NO:1 or its functional homolog or variant) by standard methods to produce antibody-producing cells, particularly antibody-producing somatic cells (e.g., B lymphocytes). These cells can then be removed from the immunized animal for immortalization. The antigen may need to first be associated with a carrier.

By "carrier" is meant any substance of typically high molecular weight to which a non- or poorly immunogenic substance (e.g., a hapten) is naturally or artificially linked to enhance its immunogenicity.

Immortalization of antibody-producing cells may be carried out using methods, which are well-known in the art. For example, the immortalization may be achieved by the transformation method using Epstein-Barr virus (EBV) [Kozbor et al. (1986) *Methods in Enzymology* 121:140]. In a preferred embodiment, antibody-producing cells are immortalized using the cell fusion method (described in [Coligan et al. (1991-1997) supra]), which is widely employed for the production of monoclonal antibodies. In this method, somatic antibody-producing cells with the potential to produce antibodies, particularly B cells, are fused with a myeloma cell line. These somatic cells may be derived from the lymph nodes, spleens and peripheral blood of primed animals, such as rodent animals including as mice and rats. In the exemplary embodiment of this invention mice, spleen cells are used. It would be possible, however, to use rat, rabbit, sheep or goat cells, or cells from other animal species instead.

Specialized myeloma cell lines have been developed from lymphocytic tumors for use in hybridoma-producing fusion procedures (Kohler et al. (1976) supra; Kozbor et al. (1986) supra; and Volk et al. (1982) *J. Virol.* 42(1):220-227).

Many myeloma cell lines may be used for the production of fused cell hybrids, including, e.g., P3X63-Ag8, P3X63-AG8.653, P3/NS1-Ag4-1 (NS-1), Sp2/0-Ag14 and S194/5.XXO.Bu.1. The P3X63-Ag8 and NS-1 cell lines have been described by Kohler and Milstein (Kohler et al. (1976) supra). Shulman et al. (1978) *Nature* 276:269-270, developed the Sp2/0-Ag14 myeloma line. The S194/5.XXO.Bu.1 line was reported by Trowbridge (1982) *J. Exp. Med.* 148(1):220-227.

Methods for generating hybrids of antibody-producing spleen or lymph node cells and myeloma cells usually involve mixing somatic cells with myeloma cells in a 10:1 proportion (although the proportion may vary from about 20:1 to about 1:1), respectively, in the presence of an agent or agents (chemical, viral or electrical) that promotes the fusion of cell membranes. Fusion methods have been described (Kohler et al. (1975) supra, Kohler et al. (1976) supra, Gefter et al. (1977) *Somatic Cell Genet.* 3:231-236 and Volk et al. (1982) supra). The fusion-promoting agents used by those investigators were Sendai virus and polyethylene glycol (PEG).

Because fusion procedures produce viable hybrids at very low frequency (e.g., when spleens are used as a source of somatic cells, only one hybrid is obtained for roughly every $1 \times 10^5$ spleen cells), it is preferable to have a means of selecting the fused cell hybrids from the remaining unfused cells, particularly the unfused myeloma cells. A means of detecting the desired antibody-producing hybridomas among other resulting fused cell hybrids is also necessary. Generally, the selection of fused cell hybrids is accomplished by culturing the cells in media that support the growth of hybridomas but prevent the growth of the unfused myeloma cells, which normally would go on dividing indefinitely. The-somatic cells used in the fusion do not maintain long-term viability in in vitro culture and hence do not pose a problem. In the example of the present invention, myeloma cells lacking hypoxanthine phosphoribosyl transferase (HPRT-negative) were used. Selection against these cells is made in hypoxanthine/aminopterin/thymidine (HAT) medium, a medium in which the fused cell hybrids survive due to the HPRT-positive genotype of the spleen cells. The use of myeloma cells with different genetic deficiencies (drug sensitivities, etc.) that can be selected against in media supporting the growth of genotypically competent hybrids is also possible.

Several weeks are required to selectively culture the fused cell hybrids. Early in this time period, it is necessary to identify those hybrids which produce the desired antibody, so that they may subsequently be cloned and propagated. Generally, around 10% of the hybrids obtained produce the desired antibody, although a range of from about 1 to about 30% is not uncommon. The detection of antibody-producing hybrids can be achieved by any one of several standard assay methods, including enzyme-linked immunoassay and radioimmunoassay techniques as, for example, described in Kennet et al. (Chou et al. U.S. Pat. No. 6,056,957).

Once the desired fused cell hybrids have been selected and cloned into individual antibody-producing cell lines, each cell line may be propagated in either of two standard ways. A suspension of the hybridoma cells can be injected into a histocompatible animal. The injected animal will then develop tumors that secrete the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels. The culture medium containing high concentrations of a single specific monoclonal antibody can be harvested by decantation, filtration or centrifugation, and subsequently purified.

The cell lines are tested for their specificity to detect the antigen of interest by any suitable immunodetection means. For example, cell lines can be aliquoted into a number of wells and incubated and the supernatant from each well is analyzed by enzyme-linked immunosorbent assay (ELISA), indirect fluorescent antibody technique, or the like. The cell line(s) producing a monoclonal antibody capable of recognizing the target antigen but which does not recognize non-target epitopes are identified and then directly cultured in vitro or injected into a histocompatible animal to form tumors and to produce, collect and purify the required antibodies.

Thus, the present invention provides in a first step monoclonal antibodies which specifically interact with a protein comprising an extracellular portion which includes SEQ ID NO:1 or a variant thereof or an epitope thereof.

The monoclonal antibody is then generally subjected to deimmunization means. Such a process may take any of a number of forms including the preparation of chimeric antibodies which have the same or similar specificity as the monoclonal antibodies prepared according to the present invention. Chimeric antibodies are antibodies whose light and heavy chain genes have been constructed, typically by genetic engineering, from immunoglobulin variable and constant region genes belonging to different species. Thus, in accordance with the present invention, once a hybridoma producing the desired monoclonal antibody is obtained, techniques are used to produce interspecific monoclonal antibodies wherein the binding region of one species is combined with a non-binding region of the antibody of another species (Liu et al. (1987) *Proc. Natl. Acad. Sci. USA* 84:3439-3443). For example, the CDRs from a non-human (e.g., murine) monoclonal antibody can be grafted onto a human antibody, thereby "humanizing" the murine antibody (European Patent Publication No. 0 239 400, Jones et al. (1986) *Nature* 321:522-525, Verhoeyen et al. (1988) *Science* 239:1534-1536 and Richmann et al. (1988) *Nature* 332:323-327). In this case, the deimmunizing process is specific for humans. More particularly, the CDRs can be grafted onto a human antibody variable region with or without human constant regions. The non-human antibody providing the CDRs is typically referred to as the "donor" and the human antibody providing the framework is typically referred to as the "acceptor". Constant regions need not be present, but if they are, they must be substantially identical to human immunoglobulin constant regions, i.e., at least about 85-90%, preferably about 95% or more identical. Hence, all parts of a humanized antibody, except possibly the CDRs, are substantially identical to corresponding parts of natural human immunoglobulin sequences. Thus, a "humanized antibody" is an antibody comprising a humanized light chain and a humanized heavy chain immunoglobulin. A donor antibody is said to be "humanized", by the process of "humanization", because the resultant humanized antibody is expected to bind to the same antigen as the donor antibody that provides the CDRs. Reference herein to "humanized" includes reference to an antibody deimmunized to a particular host, in this case, a human host.

It will be understood that the deimmunized antibodies may have additional conservative amino acid substitutions which have substantially no effect on antigen binding or other immunoglobulin functions.

Exemplary methods which may be employed to produce deimmunized antibodies according to the present invention are described, for example, in (Richmann et al. (1988) supra, Chou et al. (U.S. Pat. No. 6,056,957), Queen et al. (U.S. Pat. No. 6,180,377), Morgan et al. (U.S. Pat. No. 6,180,377) and Chothia et al. (1987) *J. Mol. Biol.* 196:901).

Another form of antibody includes an "immunoglobulin new antigen receptor" (IgNAR) which is an antibody isotype found only in cartilaginous in marine animals (sharks and rays), which has evolved over hundreds of millions of years to be stably expressed in the potent urea environment of the blood stream (Greenberg et al. (1995) *Nature* 374:168-173; Nuttall et al. (2001) *Mol Immunol* 38:313-326). The IgNAR response is antigen-driven in the shark, and both immune and naïve molecular libraries of IgNAR variable domains have been constructed and successfully screened for antigen-specific binding reagents (Greenberg et al. (1995) supra; Nuttall et al. (2001) supra). IgNAR's are bivalent, but target antigen through a single immunoglobulin variable domain (~14 kDa) displaying two complementarity determining region (CDR) loops attached to varying numbers of constant domains (Nuttall et al. (2003) *Eur J Biochem* 270:3543-3554; Roux et al. (1998) *Proc Natl Acad Sci USA* 95:11804-11809). In contrast, traditional immunoglobulin (Ig) antibodies have a variable heavy $(V_H)$+variable light $(V_L)$ domain format (~26 kDa) and bind antigen through up to six CDRs (Chothia et al. (1989) *Nature* 342:877-883; Padlan (1994) *Mol Immunol* 31:169-217). The small size, and thermodynamic and chemical stability of IgNAR variable domains $(V_{NAR}S)$, offer distinct advantages over conventional antibodies. Furthermore, the small $V_{NAR}$ size enables this unusual antibody domain access to cryptic antigenic epitopes through unusually long and variable CDR3 loops (Greenberg et al. 1995 supra; Ewert et al. (2002) *Biochemistry* 41:3628-2636; Nuttall et al. (2004) *Proteins* 55:187-197; Stanfield et al. (2004) *Science* 305:1770-1773; Streltsov et al. (2004) *Proc Natl Acad Sci USA* 101:12444-12449; Streltsov et al (2005) *Protein Sci* 14:2901-2909). IgNAR domains have been identified that recognize a variety of target antigens including: the apical membrane protein 1 (AMA-1) of *P. falciparum* (Nuttall et al, 2004 supra); the Kgp protease from *Porphyromonas gingivalis* (Nuttall et al. (2002) *FEBS Lett* 516:80-86); cholera toxin (Goldman et al, *Anal Chem* 78:8245-8255, 2006); the Tom70 mitochondrial membrane spanning protein (Nuttall et al. (2003) supra), and lysozyme (Streltsov et al. (2004) supra).

The IgNARs or more conventional antibodies may be used as therapeutic agents themselves or used to carry cytotoxic molecules to cancer cells. They can also be used in diagnosis.

Accurate and sensitive binding reagents are the cornerstone of the protein-based therapeutic and diagnostics industry. Given the high rates of cancer worldwide, there is an urgent need for such reagents targeting cancer antigens for use in therapeutic and diagnostic protocols. The identification of an extracellular portion of KRT14 and the role of KRT14 enables development of these therapeutic and diagnostic applications.

In another embodiment, the agent is a vaccine comprising a peptide portion comprising the extracellular portion of KRT14 sufficient to generate an immune response to cancer cells carrying the extracellular portion of KRT14.

The vaccine may be a peptide vaccine or a composite or conjugate agent comprising the extracellular portion of KRT14 or an analog of KRT14 and/or SEQ ID NO:1. In an embodiment, the vaccine comprises a peptide portion comprising the amino acid sequence set forth in SEQ ID NO:1 or a functional homolog thereof or variant thereof, including a peptide sequence having at least 80% similarity to SEQ ID NO:1 after optimal alignment and one or more pharmaceutically acceptable carriers, diluents or excipients. The present invention also enables a pharmaceutical composition comprising an antibody to the extracellular portion of KRT14.

The term "pharmaceutically acceptable" refers to physiologically and pharmaceutically acceptable forms of carriers, diluents or excipients.

The present invention also includes pharmaceutical compositions and formulations which include the antisense or sense compounds to down-regulate expression of KRT14. The pharmaceutical compositions of the present invention may be administered in a number of ways depending upon whether local or systemic treatment is desired and upon the area to be treated. Administration may be topical (including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product. In an embodiment, the pharmaceutical composition further comprises an additional anti-cancer agent, illustrative examples of which will be known to persons skilled in the art and described elsewhere herein. In an embodiment, the additional anti-cancer agent is selected from the group consisting of dactinomycin, daunorubicin, doxorubicin (adriamycin), idarubicin and mitoxantrone, a platinum based agent, an antimetabolite, primed T-cells and cytokines. In an embodiment, the an antimetabolite is selected from the group consisting of azaserine, D-cycloserine, nycophenolic acid, trimethoprim, 5-fluorouracil, capecitabine, methotrexate, gemcitabine, cytarabine (ara-C) and fludarabine.

A rapid, efficient and sensitive assay is also provided for the identification of cancer including a gynecological cancer such as ovarian cancer. The assay enables early detection of cancer and in particular, ovarian cancer. Notwithstanding, the present invention is not limited to just the early detection of ovarian cancer since the assay may be used at any stage of a, for example, gynecological cancer or its treatment or any complication arising therefrom.

Reference to a "cancer" with respect to a "gynecological condition" includes ovarian cancer as well as a sub-type of ovarian cancer such as mucinous or endometrial ovarian cancer or a stage of ovarian cancer such as stage I, II, III or IV. Terms such as "ovarian cancer", "epithelial ovarian cancer" and an "ovarian malignancy" may be used interchangeably herein. The present invention is useful when applied to the diagnosis of symptomatic women, but may equally be applied to the diagnosis of asymptomatic women and/or women at high risk of developing a gynecological condition. The present invention encompasses, however, a broad range of cancers in male and female subjects.

The present invention extends to a "ligand" or "binding agent" and other like terms, refers to any compound, composition or molecule capable of specifically or substantially specifically (that is with limited cross-reactivity) binding to an extracellular epitope on KRT14. The "binding agent" generally has a single specificity. Notwithstanding, binding agents having multiple specificities for two or more epitopes are also contemplated herein. The binding agents (or ligands) are typically antibodies, such as monoclonal antibodies, or derivatives or analogs thereof, but also include, without limitation: Fv fragments; single chain Fv (scFv) fragments; Fab' fragments; F(ab')2 fragments; humanized antibodies and antibody fragments; camelized antibodies and antibody fragments; and multivalent versions of the foregoing. Multivalent binding reagents also may be used, as appropriate, including without limitation: monospecific or bispecific antibodies; such as disulfide stabilized Fv fragments, scFv tandems [(scFv)₂ fragments], diabodies, tribodies or tetrabodies, which typically are covalently linked or otherwise stabilized (i.e. leucine zipper or helix stabilized) scFv fragments. "Binding agents" also include aptamers, as are described in the art.

Other non-limiting examples of suitable antigen-binding fragments of antibodies include: (i) Fd fragments; (ii) dAb fragments; and (iii) minimal recognition units consisting of the amino acid residues that mimic the hypervariable region of an antibody (e.g., an isolated CDR such as a CDR3 peptide), or a constrained FR3-CDR3-FR4 peptide. The present disclosure also extends to other engineered molecules, such as domain-specific antibodies, single domain antibodies, domain-deleted antibodies, chimeric antibodies, CDR-grafted antibodies, one-armed antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains.

In an embodiment, the antigen-binding antibody fragment comprises at least one immunoglobulin variable domain. The variable domain may comprise an amino acid sequence of any suitable length or composition and will generally comprise at least one CDR which is adjacent to or in frame with one or more framework sequences. Where the antigen-binding fragment comprises a $V_H$ domain and a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In some embodiments, the antigen-binding antibody fragment may comprise at least one variable domain covalently linked to at least one constant domain. Non-limiting configurations of variable and constant domains that may be found within an antigen-binding fragment include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. In some embodiments, the antigen-binding fragment, as herein described, may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)). A multispecific antigen-binding molecule will typically comprise at least two different variable domains, wherein each variable domain is capable of specifically binding to a separate antigen or to a different epitope on the same antigen. Any multispecific antigen-binding molecule format, including bispecific antigen-binding molecule formats, may be adapted for use in the context of an antigen-binding fragment of an antibody of the present disclosure using routine techniques available in the art.

The term "variable region" or "variable domain" refers to the domain of an immunoglobulin heavy or light chain that is involved in binding to the target antigen. The variable domains of the heavy chain and light chain ($V_H$ and $V_L$, respectively) of a native immunoglobulin molecule will generally have similar structures, with each domain comprising four conserved framework regions and three hypervariable regions (HVRs). See, e.g., Kindt et al., *Kuby Immunology*, 6th ed., W.H. Freeman and Co., page 91 (2007). A single $V_H$ or $V_L$ domain may be sufficient to confer antigen-binding specificity.

For therapeutic applications, it may be desirable to modify the binding agent for compatibility with the target species; that is, the species to which the binding agent is to be administered. In an embodiment, the binding agent is a humanized binding agent.

In some embodiments, the FRs of the binding agents, including the antibodies or antigen-binding fragments thereof, as described herein, may be identical to the FR of germline sequences of the target species (i.e., the species to which the binding agents will be administered). In some embodiments, the FR may be naturally or artificially modified. Whilst it is generally desirable that each of the FR sequences are identical to FR sequences derived from one or more immunoglobulin molecules of the target species, including to minimize an immune response being raised against the binding molecule upon administration to a subject of the target species, in some embodiments, the binding agent may comprise one or more amino acid residues across one or more of its FR sequences that would be foreign at a corresponding position in one or more FR from the target species. Preferably, where the binding agent comprises one or more amino acid residues across one or more of its FR sequences that would be foreign at a corresponding position in the target species, that "foreign" amino acid residue will not (i) adversely impact the binding specificity of the binding agents to its target antigen (KRT14), and/or (ii) cause an immune response to be raised against the binding agent when administered to a subject of the target species.

In an embodiment disclosed herein, the agent (including antibodies that bind to the extracellular portion of KRT14 and KRT14-binding fragments thereof, as described herein) comprises an immunoglobulin heavy chain variable domain (VH) and an immunoglobulin light chain variable domain (VL), wherein the VH comprises a complementarity determining region 1 (VH CDR1) comprising the amino acid sequence of SEQ ID NO:6, a VH CDR2 comprising the amino acid sequence of SEQ ID NO:7 and a VH CDR3 comprising the amino acid sequence of SEQ ID NO:8; and wherein the VL comprises a complementarity determining region 1 (VL CDR1) comprising the amino acid sequence of SEQ ID NO:9, a VL CDR2 comprising the amino acid sequence of SEQ ID NO:10, and a VL CDR3 comprising the amino acid sequence of SEQ ID NO:11.

In an embodiment, the VH comprises:

(a) a VH framework region 1 (FR1) comprising an amino acid sequence having at least 80% sequence identity to SEQ ID NO:12;

(b) a VH FR2 comprising an amino acid sequence having at least 80% sequence identity to SEQ ID NO:13;

(c) a VH FR3 comprising an amino acid sequence having at least 80% sequence identity to SEQ ID NO:14; and (d) a VH FR4 comprising an amino acid sequence having at least 80% sequence identity to SEQ ID NO:15;

and the VL comprises:

(e) a VL FR1 comprising an amino acid sequence having at least 80% sequence identity to SEQ ID NO:16;

(f) a VL FR2 comprising an amino acid sequence having at least 80% sequence identity to SEQ ID NO:17;

(g) a VL FR3 comprising an amino acid sequence having at least 80% sequence identity to SEQ ID NO:18; and (h) a VL FR4 comprising an amino acid sequence having at least 80% sequence identity to SEQ ID NO:19.

In an embodiment, the VH comprises an amino acid sequence having at least 80% sequence identity to SEQ ID NO:3, and the VL comprises an amino acid sequence having at least 80% sequence identity to SEQ ID NO:5.

The present disclosure also extends to an agent that binds specifically to an extracellular portion of KRT14 on cancer cells, or to a KRT14-binding fragment thereof, wherein the agent comprises an immunoglobulin heavy chain variable domain (VH) and an immunoglobulin light chain variable domain (VL), wherein the VH comprises a complementarity determining region 1 (VH CDR1) comprising the amino acid sequence of SEQ ID NO:6, a VH CDR2 comprising the amino acid sequence of SEQ ID NO:7 and a VH CDR3 comprising the amino acid sequence of SEQ ID NO:8; and wherein the VL comprises a complementarity determining region 1 (VL CDR1) comprising the amino acid sequence of SEQ ID NO:9, a VL CDR2 comprising the amino acid sequence of SEQ ID NO:10, and a VL CDR3 comprising the amino acid sequence of SEQ ID NO:11.

In an embodiment, the VH comprises:

(a) a VH framework region 1 (FR1) comprising an amino acid sequence having at least 80% sequence identity to SEQ ID NO:12;

(b) a VH FR2 comprising an amino acid sequence having at least 80% sequence identity to SEQ ID NO:13;

(c) a VH FR3 comprising an amino acid sequence having at least 80% sequence identity to SEQ ID NO:14; and (d) a VH FR4 comprising an amino acid sequence having at least 80% sequence identity to SEQ ID NO:15;

and the VL comprises:

(e) a VL FR1 comprising an amino acid sequence having at least 80% sequence identity to SEQ ID NO:16;

(f) a VL FR2 comprising an amino acid sequence having at least 80% sequence identity to SEQ ID NO:17;

(g) a VL FR3 comprising an amino acid sequence having at least 80% sequence identity to SEQ ID NO:18; and (h) a VL FR4 comprising an amino acid sequence having at least 80% sequence identity to SEQ ID NO:19.

In an embodiment, the VH comprises an amino acid sequence having at least 80% sequence identity to SEQ ID NO:3, and the VL comprises an amino acid sequence having at least 80% sequence identity to SEQ ID NO:5.

The ligands and binding agents may be used in assays to detect the presence of cells carrying KRT14. ECLIA, ELISA and Luminex LabMAP immunoassays are examples of suitable assays to detect levels of the biomarkers. In one example, a first binding reagent/antibody is attached to a surface and a second binding reagent/antibody comprising a detectable group binds to the first antibody. Examples of detectable-groups include, for example and without limitation: fluorochromes, enzymes, epitopes for binding a second binding reagent (for example, when the second binding reagent/antibody is a mouse antibody, which is detected by a fluorescently-labeled anti-mouse antibody), for example an antigen or a member of a binding pair, such as biotin. The surface may be a planar surface, such as in the case of a typical grid-type array (for example, but without limitation, 96-well plates and planar microarrays) or a non-planar surface, as with coated bead array technologies, where each "species" of bead is labeled with, for example, a fluoro-chrome (such as the Luminex technology described in U.S. Pat. Nos. 6,599,331, 6,592,822 and 6,268,222), or quantum dot technology (for example, as described in U.S. Pat. No. 6,306,610). Such assays may also be regarded as laboratory information management systems (LIMS).

As used herein, "immunoassay" refers to immune assays, typically, but not exclusively sandwich assays, capable of detecting and quantifying a desired biomarker, namely the extracellular portion of KRT14.

Methods for diagnosing a gynecological condition or other cancer by determining the presence of the extracellular portion of KRT14 and using the level of extracellular portion as second knowledge base data in an algorithm generated with first knowledge base of known amounts of KRT14 in patients with a known disease. Also provided are methods of detecting preclinical ovarian cancer or other cancer comprising determining the presence and/or velocity of KRT14 in a subject's sample. By "velocity" it is meant the change in the concentration of KRT14 in a patient's sample over time.

As indicated above, a gynecological condition includes cancer or a compilation thereof. The term "cancer" as used herein includes all cancers including but not limited to a "gynecological cancer". In one embodiment, a gynecological cancer, including, but not limited to, tubal metaplasia, ovarian serous borderline neoplasms, serous adenocarcinomas, low-grade mucinous neoplasms and endometrial tumors. In a specific embodiment, the gynecological cancer is an ovarian neoplasm, undergoing aberrant Mullerian epithelial differentiation. Other gynecological conditions contemplated herein include inflammatory disorders such as endometriosis. As indicated above, the present invention extends to a broad range of cancers by male and female subjects.

The term "sample" as used herein means any sample containing cancer cells that one wishes to detect including, but not limited to, biological fluids (including blood, plasma, serum, ascites), tissue extracts, freshly harvested cells, and lysates of cells which have been incubated in cell cultures. In a particular embodiment, the sample is gynecological tissue, blood, serum, plasma or ascites.

As indicated above, the "subject" can be any mammal, generally human, suspected of having or having a gynecological condition or other cancer. The subject may be referred to as a patient and is a mammal suspected of having or having a cancer or at risk of developing same. The term "condition" also includes complications arising therefrom.

The term "control sample" includes any sample that can be used to establish a first knowledge base of data from subjects with a known disease status.

The method of the subject invention may be used in the diagnosis and staging of a cancer such as a gynecological cancer including ovarian cancer. The present invention may also be used to monitor the progression of a condition and to monitor whether a particular treatment is effective or not. In particular, the method can be used to confirm the absence or amelioration of the symptoms of the condition such as following surgery, chemotherapy, immunotherapy, and/or radiation therapy. The methods can further be used to monitor chemotherapy and aberrant tissue reappearance.

As indicated above, antibodies may be used in any of a number of immunoassays which rely on the binding interaction between an antigenic determinant of the biomarker and the antibodies. Examples of such assays are radioimmunoassay, enzyme immunoassays (e.g., ECLIA, ELISA), immunofluorescence, immunoprecipitation, latex agglutination, hemagglutination and histochemical tests. The antibodies may be used to detect and quantify the level of the biomarker in a sample in order to determine its role in cancer and to diagnose the cancer.

In particular, the antibodies of the present invention may also be used in immunohistochemical analyses, for example, at the cellular and subcellular level, to detect a biomarker, to localize it to particular cells and tissues, and to specific subcellular locations, and to quantitate the level of expression. The medicament, in addition to being an antibody, may be any affinity reagent including but not limited to aptamers, monobodies, anti-calins, DARPins and nanobodies and the like.

Cytochemical techniques known in the art for localizing antigens using light and electron microscopy may be used to detect cells carrying the extracellular domain of KRT14. Generally, an antibody of the present invention may be labeled with a detectable substance and a biomarker protein may be localized in tissues and cells based upon the presence of the detectable substance. Examples of detectable substances include, but are not limited to, the following: radioisotopes (e.g., $^3$H, $^{14}$C $^{35}$S, $^{125}$, $^{131}$I) fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin e.g. streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains; epitope tags). In an embodiment, labels are attached via spacer arms of various lengths to reduce potential steric hindrance. Antibodies may also be coupled to electron dense substances, such as ferritin or colloidal gold, which are readily visualized by electron microscopy.

The antibody or sample may be immobilized on a carrier or solid support which is capable of immobilizing cells, antibodies, etc. For example, the carrier or support may be nitrocellulose, or glass, polyacrylamides, gabbros and magnetite. The support material may have any possible configuration including spherical (e.g., bead), cylindrical (e.g., inside surface of a test tube or well, or the external surface of a rod), or flat (e.g., sheet, test strip) Indirect methods may also be employed in which the primary antigen-antibody reaction is amplified by the introduction of a second antibody, having specificity for the antibody reactive against biomarker protein. By way of example, if the antibody having specificity against the extracellular domain of KRT14 is a rabbit IgG antibody, the second antibody may be goat anti-rabbit gamma-globulin labeled with a detectable substance as described herein.

Where a radioactive label is used as a detectable substance, the KRT14 biomarker may be localized by radioautography. The results of radioautography may be quantitated by determining the density of particles in the radioautographs by various optical methods, or by counting the grains.

Labeled antibodies against KRT14 may be used in locating tumor tissue in patients undergoing surgery i.e., in imaging. Typically for in vivo applications, antibodies are labeled with radioactive labels (e.g., iodine-123, iodine-125, iodine-131, gallium-67, technetium-99, and indium-111). Labeled antibody preparations may be administered to a patient intravenously in an appropriate carrier at a time several hours to four days before the tissue is imaged. During this period unbound fractions are cleared from the patient and the only remaining antibodies are those associated with tumor tissue. The presence of the isotope is detected using a suitable gamma camera. The labeled tissue can be correlated with known markers on the patient's body to pinpoint the location of the tumor for the surgeon.

Accordingly, in another embodiment the present invention provides a method for detecting cancer in a patient comprising:

(a) providing a sample from the patient;
(b) contacting the sample with an agent that binds to an extracellular epitope of KRT14 to determine the levels thereof and subjecting the levels to an algorithm to provide an index of probability of the patient having a cancer; and
(c) diagnosing the risk of the patient having cancer based on the index of probability.

In another embodiment, the present invention provides a method for detecting circulating KRT14-positive cancer cells in a patient, the method comprising:

(a) providing a blood sample from the patient;
(b) contacting the blood sample with an agent that binds to an extracellular epitope of KRT14 to determine the presence of KRT14-positive cancer cells in the sample.

The methods described herein may be performed by utilizing pre-packaged diagnostic kits comprising the necessary reagents to perform any of the methods of the invention. For example, the kits may include at least one specific antibody to an extracellular portion of KRT14, which may be conveniently used, e.g., in clinical settings, to screen and diagnose patients and to screen and identify those individuals exhibiting a predisposition to developing cancer. The kit also includes detailed instructions for carrying out the methods of the present invention.

The present invention further provides an algorithm-based screening assay to screen samples from patients. Generally, input data are collected based on levels of KRT14 and subjected to an algorithm to assess the statistical significance of any elevation or reduction in levels which information is then output data. Computer software and hardware for assessing input data are encompassed by the present invention.

The assay of the present invention permits integration into existing or newly developed pathology architecture or platform systems. For example, the present invention contemplates a method of allowing a user to determine the status of a subject with respect to a cancer, or to a subtype or stage thereof, the method comprising:

(a) receiving data in the form of presence of the extracellular portion of KRT14 via a communications network;

(b) processing the subject data via an algorithm which provides a disease index value;

(c) determining the status of the subject in accordance with the results of the disease index value in comparison with predetermined values; and (d) transferring an indication of the status of the subject to the user via the communications network.

In another embodiment disclosed herein, there is provided a method of monitoring a cancer in a patient, the method comprising:

(a) providing a blood sample from a patient at a first time point;

(b) contacting the sample of (a) with an agent that binds to an extracellular epitope of KRT14 to determine the level of KRT14-positive cancer cells in the sample;

(c) providing a blood sample from a patient at a second time point, wherein the first time point is different to the second time point;

(d) contacting the sample of (c) with an agent that binds to an extracellular epitope of KRT14 to determine the level of KRT14-positive cancer cells in the sample; and (e) determining whether there has been a change in the level of KRT14-positive cancer cells in the patient between the first and second time points;

wherein a change in the level of KRT14-positive cancer cells in the patient between the first and second time points is indicative of a change to the status of the cancer in the patient.

Such methods may suitably be used to monitor changes in the status or stage of cancer (e.g., in response to therapy) or to detect recurrence (e.g., after tumour resection).

In an embodiment, the cancer is a gynaecological cancer. In an embodiment, the gynaecological cancer is ovarian cancer or a stage or form of ovarian cancer. In another embodiment, the cancer is selected from brain, bladder, liver, breast, lung, pancreatic, bowel, colon, gastrointestinal tract, stomach, throat, endometrial and colorectal cancer.

Reference to an "algorithm" or "algorithmic functions" as outlined above includes the performance of a multivariate analysis function. A range of different architectures and platforms may be implemented in addition to those described above. It will be appreciated that any form of architecture suitable for implementing the present invention may be used.

EXAMPLES

Aspects disclosed herein are further described by the following non-limiting Examples. The following materials and methods may be employed.

Cell Culture. Cell lines OVCAR-4 (NIH-OVCAR4) and CaOV-3 #HTB-75 were purchased from ATCC and NIH. OVCAR-4 cells were maintained in Roswell Park Memorial Institute medium-1640 (RPMI) (Life Technologies, 21870092); CaOV-3 cells were maintained in Dulbecco's Modified Eagle Medium (DMEM) (Thermo Scientific, #11965118); SKOV3 cells (ATCC@#HTB-77™) were maintained in Dulbecco's Modified Eagle Medium (DMEM)/Ham's F-12 (DMEM/F12) (Thermo Scientific, #11965118); COV362.4, Sigma Aldrich (Sigma #07071904) were maintained in high glucose Dulbecco's Modified Eagle Medium (DMEM-HG); BT-16, Atypical teratoid/rhabdoid tumour (CVCL_M156) and NCI-H1573 Lung adenocarcinoma (NCI-H1573) were both maintained in Rosswel Park Memorial Institute (RPMI), MDA-MB-468; Triple negative breast cancer cells (CVCL_0419) were maintained in DMEM, ANE CA (ATCC HTB-11) in Eagle Minimum essential medium EMEM and SW 620 cells (ATCC CCL-227) were maintained in Leibovitz's L-15 medium. All media was supplemented with 10% fetal calf serum (FCS) (Thermo Fisher, #16000044) and 1% Penicillin-Streptomycin (Thermo Scientific, #15240062). The ID8 mouse epithelial OC cell line (Dr. Kathy Roby, Kansas University Medical Center, Kansas City, KA, USA) was grown in Gibco DMEM (ThermoFisher Scientific) containing 4% fetal bovine serum (FBS) with 1% insulin-transferrin-selenite (ITS) and 1% penicillin/streptomycin (PS). The human mesothelial cell line LP9 (Coriell Institute Cell Repository #AG07086) was maintained in HamsF12/199 medium with 10% v/v FCS, 1% v/v Penicillin-Streptomycin, 10 ng/ml EGF and 0.4 ug/ml hydrocortisone. All lines were maintained at 37° C. with 5% v/v $CO_2$ and cell viability counts were conducted prior to the commencement of all assays using the Countess (Registered Trade Mark) II FL Automated Cell Counter. Non adherent tumor cells are obtained from the malignant ascites following patient consent using an established purification methods (Latifi et al. (2012) *PLoS ONE* 7(10)) and maintained under low adhesive conditions prior to analyses by culture on low adhesion plates in MCDB:F12 medium and 10% v/v FCS.

CRISPR KRT14 targeted disruption and KRT14 overexpression. CRISPR-mediated gene silencing was performed as per the Zhang lab protocol (Cong et al. (2013) *Science* 339(6121):819-23), using 3 guide strands per gene. Cells were transfected with guide strands (1-3), a non-targeting control or the KRT14 overexpression construct KRT14$^{OE}$ (Origene #RC214907) using Lipofectamine (Registered Trade Mark) 2000 Transfection Reagent (Invitrogen, #11668019) in DMEM as per the manufactures protocol. Following transfection and a 12 hour recovery period cells were sub-cultured into selective medium and maintained under selective pressure by the addition of 1 μg/ml Puromycin (Sigma-Aldrich, #P8833) or Geneticin (Trade Mark) Selective Antibiotic (G418 Sulfate) (Life Technologies Australia #10131-035). Cells were subject to limited dilution where selection medium was replaced every two days for approximately two weeks. Individual colonies were expanded and knockdown of the target gene measured by Western Blot analyses and verified by Sanger sequencing.

Human Tissue Arrays and Immunohistochemistry. Immunohistochemistry was performed on tissue micrarray (TMA) sections purchased from USBIOMAX (#ov2085, #ov20811) or generated in house (tumour and fallopian tube) as previously described [Bilandzic et al. (2014) *Cancer Lett* 354(1): 107-114; Rainczuk et al. (2013) *J Proteome Res*; Salamonsen et al. (2013) *Fertil Steril* 99(4):1086-92](Supplementary Data 6 and 7). For antigen retrieval, sections were incubated for 10 minutes in 50 mM glycine (pH 3.5) at 90° C. Sections were incubated overnight at 4° C. with Rb-KRT14 antibody (1:100, Sigma, SAB4501657) and mAb AN-17 (1:500) in 0.1% w/v BSA/PBS. Subsequent steps were performed at room temperature, with PBS washes between incubations. Sections were incubated with: Goat anti-rabbit IgG peroxidase conjugate (1:1000, Dako, Glostrup, Denmark; catalog item PO448), Biotinylated Rabbit Anti-Goat IgG Antibody (1:1000, Vector Laboratories Cat. No: BA-5000) or Biotinylated Rabbit Anti-Mouse IgG Antibody (1:1000, Vector Laboratories. Cat. No: BA-9200) for 1 hour, followed by a Vectastain Elite ABC kit according to the manufacturer's instructions (Vector Laboratories, Burlingame, California). Antibody binding was detected as a brown precipitate after development with 3,3'-diaminobenzidine tetrahydrochloride, and Harris hematoxylin was used as counterstain. The sections were mounted under glass coverslips in Depex (BDH Laboratory Supplies, Poole, United Kingdom). Positive immunostaining was assessed relative to parallel sections exposed to an isotype (IgG) control. Immunostaining in tumor and stromal tissue was assessed using Aperio ImageScope (v 12.3.3) as described (Rainczuk et al. (2013) supra).

Western Blot analyses. SDS-PAGE and western blotting were performed as previously described in Bilandzic et al. (2013) *Mol Endocrinol,* 2013. 27(3):466-79). Blots were probed using antibodies against KRT14 (1:1000, SAB4501657), mAb AN-17 and β-actin (1:20,000; Sigma-Aldrich, Castle Hill, Australia). Secondary antibodies HRP-conjugated goat anti-mouse, anti-rabbit and donkey anti-goat (1:50,000; Merck Millipore, Kilsyth, Australia) were used Bilandzic et al. (2013) *Mol Endocrinol,* 2013. 27(3): 466-79). Protein bands were detected using Clarity Western ECL blotting substrate (Biorad #1705061) and visualized using a ChemiDoc (Trade Mark) MP System (Bio-Rad, #1708280).

xCELLigence Real Time Cell Analyses (RTCA). Real time cell analyses (RTCA) were conducted using an xCELLigence RTCA SP 96-well instrument (ACEA Biosciences). Cell lines were synchronized in Go phase by overnight incubation in serum-free media prior to commencement. For proliferation assays, cells were seeded at $0.5 \times 10^3$ cells/0.14 ml/per well (as outlined in the experimental text), and impedance readings taken every 5 minutes for 8 hours (in order to monitor cell adhesion), and subsequently every 15 minutes for 24 hours (to monitor cell proliferation). For invasion assays the upper chamber of a CIM-16 well plate was coated with Matrigel matrix (1:10 in SFM; BD Biosciences, San Jose, CA). Cells were seeded into the upper chamber (as above), with media+/−10% v/v FBS added to the lower chamber. All assays were performed in duplicate or triplicate, with at least three independent experiments.

Peritoneal microenvironment model. To establish a model of the peritoneal microenvironment, two-chamber RTCA CIM plate wells were prepared by coating the upper chamber with Matrigel (1:10 in SFM; BD Biosciences) and then $7 \times 10^4$ LP9 cells/well were added and monitored until a confluent monolayer was formed (Domcke et al. (2013) *Nat Commun* 4:2126). Spheroids (obtained from fresh patient ascites; 10 spheres/well) were seeded in SFM in the upper chamber, and media±10% v/v FBS added to the lower chamber. Real time readings were used to determine the optimal time(s) to use as collection points for MALDI imaging analysis, with all samples prepared in duplicate or triplicate wells per experiment. As an additional control, we also carried out concurrent endpoint invasion assays in parallel using modified Boyden chambers. In this case, mesothelial LP9 cells were labeled using Cell Trace (Trade Mark) CFSE prior to inoculation with ovarian cancer spheroids. Mesothelial invasion was assessed according to the retraction of CSFE-labeled mesothelial cells underneath spheroids, using a Cytation (Trade Mark) 3 Multimode Imager (BioTek Instruments, Winooski USA).

Preparation of samples for MALDI-IMS. Spheroid-mesothelial interfaces were cocultured on Thermanox (Trade Mark) sectionable coverslips, and agar-capped at time points determined corresponding to pre-, during- and post-invasion (as measured by RTCA assay). Samples were sectioned at 5 m and the invasive interface was located by H&E staining on periodic sections. Once identified two unstained sections through the interface were placed on an indium-tin oxide (ITO) slide for MALDI processing (Bruker Daltonik, GmbH).

MALDI IMS. Tryptic peptides at the ovarian cancer-spheroid-mesothelial interface were identified using the ImageID workflow (Bruker). Trypsin was applied to serial tissue sections by nebulization using an ImagePrep spray device (Bruker). Samples were digested in a humidified chamber for 90 minutes then peptides were extracted and purified using a C18 pipette tip. LC-MALDI analysis was performed using an ultrafleXtreme MALDI-TOF/TOF (Bruker) and a Dionex Ultimate 3000 RSLC system (Thermo) as described (Rainczuk et al. (2014) *Int J Cancer* 134(3):530-41). MALDI imaging acquisition of a subsequent digested serial section was then performed using flexImaging 4.1 (Bruker) as previously described (Rainczuk et al. (2014) supra). LC-MALDI data and MALDI imaging data was compared and filtered using ImageID software (Bruker), and mass peaks matched between imaging data and LC-MALDI analysis. Mass tolerance for peak matching was automatically calculated by the ImageID software.

Methylcellulose overlay and sphere formation. Ovarian cancer cells were dissociated by trypsinization and resuspended in complete cell culture medium (minimum viability of 98% as determined by the countess cell counter). 2,500 cells per sphere were overlaid in 0.25% w/v methylcellulose (Sigma Aldrich, Castle Hill, Australia) in serum free medium, and seeded into a single well of a 96-well CELL-STAR (Registered) U-bottom Suspension Culture Plate (Greiner Bio One, Interpath Services PTY, Vic, Australia). Spheroid aggregation and formation for each line was observed and imaged at regular intervals using a light microscope. Formed spheres were harvested using a wide bore tip and centrifugation.

Mesothelial displacement assay. The human mesothelial cell line LP9 was seeded as above and incubated at 37° C. until a confluent monolayer was formed. Ovarian cancer spheres (as above) were collected, and 16-spheres were seeded into wells containing the confluent mesothelial monolayer. Mesothelial displacement and outgrowth were imaged at regular intervals using phase-contrast microscopy.

In vitro wound repair assay. Ovarian cancer cells (or other cancer cell lines—BT16, NCI-H1573, AN3CA, SW620 and MDA-MB-468) were grown in complete medium to confluency in a 12-well plate, then serum-starved overnight to synchronize at $G_0$. The following day cell culture medium was removed, and cell monolayers were wounded by scraping with a pipette tip attached to suction. Non-adherent cells were removed by gentle washes with PBS, and complete growth medium with or without mAb AN-17 (1 µg/ml) or commercial KRT14 polyclonal antibody (1 µg/ml) was replaced. The wound area was imaged under a phase microscope (Leica) at regular intervals ranging from 0-72 h. Wound closure was measured in image series using Analy-SIS LS Research Software (Olympus) to determine the area of the wound on each day. Experiments were repeated in triplicate with at least six wound areas observed per growth condition.

Matrigel and Collagen I Outgrowth assay: Staining and Imaging. Protocol was adapted from Nguyen-Ngoc et al. (2012) *Proc Natl Acad Sci USA.* 109(39):E2595-604. Briefly ovarian cancer spheroids were collected to yield a suspension of 6 spheres per matrix. Spheres were embedded in either 3D Matrigel (354230; BD Biosciences) or rat-tail collagen I (354236; BD Biosciences). Cultures were set up in 8 well on coverglass slides (94.6190.802, Starstedt) as per (Nguyen-Ngoc et al. (2012) supra. For antibody staining spheres cultured in either matrigel or collagen I were fixed with 4% w/v paraformaldehyde for 30 minutes, rinsed twice in PBS for 10 minutes, permeabilized with 0.5% v/v Triton X-100 in PBS for 20 minutes, and rinsed twice in PBS for 10 minutes and blocked in 10% v/v FBS in PBS for 2 hours at room temperature then incubated with primary antibody (1:1000, Anti-N Cadherin antibody [5D5] ab98952 AbCam and 1:500, KRT14) overnight at 4° C. The following day samples were washed three times with PBS and incubated with secondary antibodies: 1:2000, goat Anti-Rabbit IgG Alexa 467, ab150083 and 1:2000 goat Anti Mouse IgG Alexa 488, ab150117) for 3 hours at room temperature then rinsed three times in PBS for 10 min. Samples were imaged using a Cytation (Trade Mark) 3 Mulitmode Imager (BioTek Instruments, Winooski USA) with Gen5 Image+software or Nikon C1 Confocal microscope (Monash Micro Imaging Facility, Monash).

Real time PCR. Total RNA was extracted from primary high grade serous ovarian tumours (n=3) and the whole normal ovary (n=3) using the Tissue Lyser LT system with 5 mm Stainless steel beads and the RNeasy Mini Kit (Qiagen). Total RNA was extracted from ovarian cancer cell lines OVCAR4 and CaOV3, grown as monolayers or spheroids (KRT14$^{KO}$ and wild-type lines); ascites derived ovarian cancer (n=3) or benign fibroma (n=2) spheroids; and the target peritoneal cell layer LP-9 using the RNeasy Mini Kit (Qiagen) as per manufactures protocol. Sense and antisense oligonucleotide primers to KRT14, HNRN, FNDC3B, 18S, CDCA8 were designed against published human sequences and verified as previously described (Bilandzic et al. (2009) *Mol Endocrinol*, 23(4):539-48). cDNA was synthesized using Superscript III reverse transcriptase (Life Technologies, Grand Island, NY). Real-time PCR samples were prepared to a final volume of 10 µl using the Applied Biosystems ABI SYBR mix (Scoresby, Victoria, Australia). Quantitative real time PCR was completed as previously described (Bilandzic et al. (2009) supra) using the Applied Biosystems ABI 7900 HT Fast real-time machine with all reactions performed in triplicate. Yields were converted to femtograms based on the standard curve for each PCR product, and the resultant mRNA levels were normalized to the 18S mRNA level per sample.

Statistical Analyses. Statistical analyses were conducted using GraphPad Prism (Version 6; GraphPad Software Inc., San Diego, CA). For data derived from cell assays, means were compared using one-way or two-way ANOVA with Bonferroni's, Dunnett's, or Tukey's post hoc tests, as indicated. To determine whether mRNA expression significantly differed between samples, a Mann-Whitney-U test or unpaired t-test was performed. Means were considered significantly different if p<0.05. All experiments were independently repeated at least three times.

Kaplan-Meier Curves. The Kaplan-Meier online plotter tool was used to generate survival curves using mRNA data from serous ovarian cancer patients from 15 public ovarian cancer datasets where best cutoff values were auto-selected by the plotter tool, and log rank, p value and hazard ratio (and 95% confidence intervals) were calculated (Lanczky et al. (2016) *Breast Cancer Res Treat*. 3 (160):439-446).

Example 1

Adhesion and Proliferation do not Predict the Invasive Capacity of Cells

Metastatic ovarian cancer cells interact with the mesothelial monolayer lining the peritoneal cavity and organs, invading and attaching to the underlying matrix to establish secondary nodules (Kenny et al. (20017) *Int J Cancer* 121(7):1463-72; Burleson et al. (2006) *J Transl Med* 4:6; Sodek et al. (2012) *Cancer Metastasis Rev* 31(1-2):397-414). Using primary ascites-derived tumor cells, mesothelial displacement was assessed with the emergence of invasive filopodia from spheroids in vitro over an extended timeframe. On assay commencement, spheroids from benign or malignant samples were of similar size and displayed no apparent morphological differences. Extensive filopodia outgrowth and clearance of the underlying mesothelial layer occurred within 24 hours for all malignant samples; by contrast, benign spheroids did not display any visible evidence of outgrowth or invasion. The lack of invasion was not due to failed adhesion or reduced cell proliferation; indeed, benign cells displayed comparatively elevated adherence to uncoated and fibronectin coated culture plates and achieved a higher proliferative index than malignant cell samples in RTCA assays. These data demonstrate that only malignant cells exhibited invasive capacity; and that invasive potential cannot be predicted from the adhesive or proliferative capacity of cells in vitro.

Example 2

Proteomic Profiling Identifies Proteins Unique to the Invasion Interface

No prior studies have examined proteins directly at the interface between actively invading cancer cells and the mesothelium. To assess invasion-related protein abundance and localization, spheroid/mesothelial co-cultures were harvested following attachment to the mesothelium, but prior to the onset of invasion (as determined by RTCA assay). Parallel endpoint Boyden chamber assays were used to confirm that mesothelial attachment but not invasion had occurred in samples used for MALDI IMS analyses.

Figure 1:
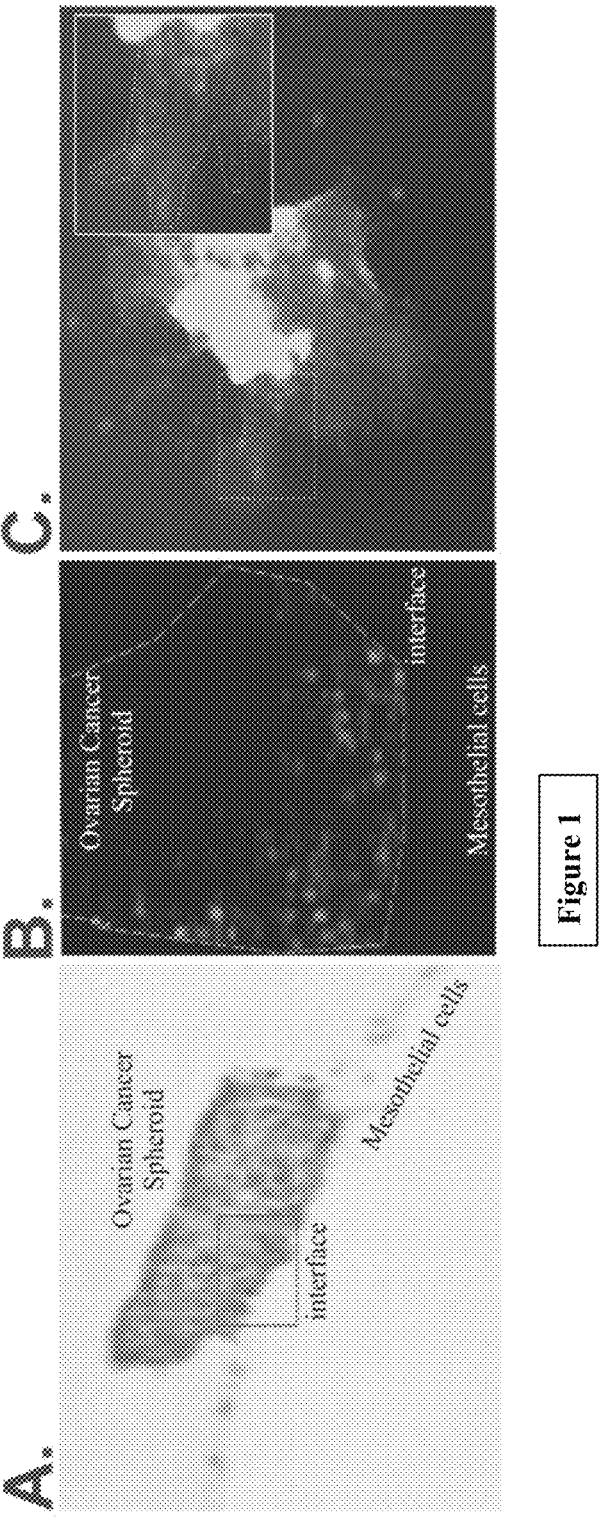
FIGS. 1A through 1C are photographical representations showing the identification of KRT14 at the leading edge of invasive ovarian cancer deposits.

Cell-spheroid interface cultures were embedded in agarose, sectioned and located by IHC (FIG. 1A); serial sections were then analyzed by IMS to identify proteins localized at the invasion interface. Analyses also included ascites-derived spheroids from a patient with benign fibroma (not shown), to control for heterotypic variance between samples. MALDI IMS and subsequent LC-MALDI-MS/MS identified 26 proteins, uniquely present in co-cultures containing malignant but not benign spheroids, at the spheroid/mesothelial interface. Amongst these were several proteins previously associated with ovarian cancer (e.g. HSP90, AMH and OSM) [Vesci et al. (2014) *Int J Oncol* 45(4): 1421-9; Liu et al. (2013) *Clin Cancer Res* 19(18):5053-67; Kim et al. (2014) *Obstet Gynecol Sci* 0.57(5):343-57; Richards (2013) *ISRN Inflammation* 2013: 23], validating the approach and suggesting they may play important roles during the early stages of invasion. Analyses were further restricted to: (i) include only those proteins identified in every malignant high-grade serous ovarian cancer (HGSC) sample; and (ii) exclude proteins that were also identified in the mesothelial cell monolayer. Four proteins (KRT14, HRNR, CDCA8 and FNDC3B) were identified as unique to all patient HGSC cells at the cancer-mesothelial interface following this high stringency approach. Immunostaining on TMAs and RT-PCR on fresh frozen tissue was also used to confirm candidate expression and localization in independent tumor tissue compared to histologically normal ovarian tissue.

Example 3

KRT14 on the Invasive Interface is Required for Ovarian Cancer Cell Invasion

The abundance of HRNR, KRT14, CDCA8 and FNDC3B was examined in multiple HGSC cell lines (OVCAR3, OVCAR4 and CaOV3) (Domcke et al. (2013) supra) by Western blot. In agreement with the proteomic profiling, HRNR, KRT14 and CDCA8 were detected in cancer cell lysates but not in the mesothelial cell controls. FNDC3B was detected in LP9 mesothelial cells, and was excluded from further analyses. KRT14, CDCA8 and HRNR were then knocked out (CaOV3 and OVCAR4 cell lines) using CRISPR, with their specific loss confirmed in clonal populations by sequencing PCR and Western blot. The effects of functional KRT14, CDCA8 or HRNR loss on cell proliferation and invasion were tested by RTCA. Compared to either untreated or non-targeting controls, cells lacking HRNR or CDCA8 showed significantly reduced proliferation (not shown); by contrast, the loss of KRT14 did not affect proliferation (FIGS. 2A-2B), suggesting it was not required for tumor cell viability or growth. Both CDCA8 and HRNR knock-out cells also retained invasion competency; CDCA8 knock-out cells displayed similar invasion kinetics to untreated or non-targeting cells, whilst HRNR knock-out cells exhibited a lag in the onset of invasion. However, cells lacking functional KRT14 displayed a complete loss of invasive capacity (FIG. 2A) with no invasion observed after 30h (or over extended periods up to 7 days). The KRT14-mediated loss of invasion competence was confirmed in 2D wound healing assays (FIG. 2B), where KRT14 knock-out (KRT14$^{KO}$) cells failed to repair a wounded monolayer after 48 hours. Further studies thus focused on KRT14 as a key gene controlling the invasive capacity of malignant ovarian cancer cells.

Example 4

Peritoneal Microenvironment Model

Using a peritoneal microenvironment model, KRT14 is detected expressed at the earliest stages of metastasis on the "leading edge" of invasive ovarian cancer cells. These cells are defined as "leader cells". In this model, ovarian cancer spheroids are overlaid onto a mesothelial monolayer, established on a matrigel matrix in a CIM-16 RTCA plate. Spheroid attachment and invasion through the mesothelial monolayer/matrix are monitored in real time using an xCEL-Ligence instrument, providing a dynamic snapshot of invasive cell behavior.

Spheroids from patients with either benign (ovarian fibroma) or malignant (HGSC) disease were isolated from ascites fluid and assessed for invasive capacity. Malignant HGSC cells rapidly invaded through the mesothelial monolayer, with all samples demonstrating active invasion within 4h post-addition. By contrast, spheroids obtained from a patient with benign fibroma failed to disrupt the mesothelial monolayer. Thus, the onset of cancer cell invasion occurred rapidly upon contacting a mesothelial monolayer in vitro, suggesting a timeframe for the analysis of the early events involved in invasion.

Example 5

Real-Time In Vitro Invasion Assay

Figure 2:
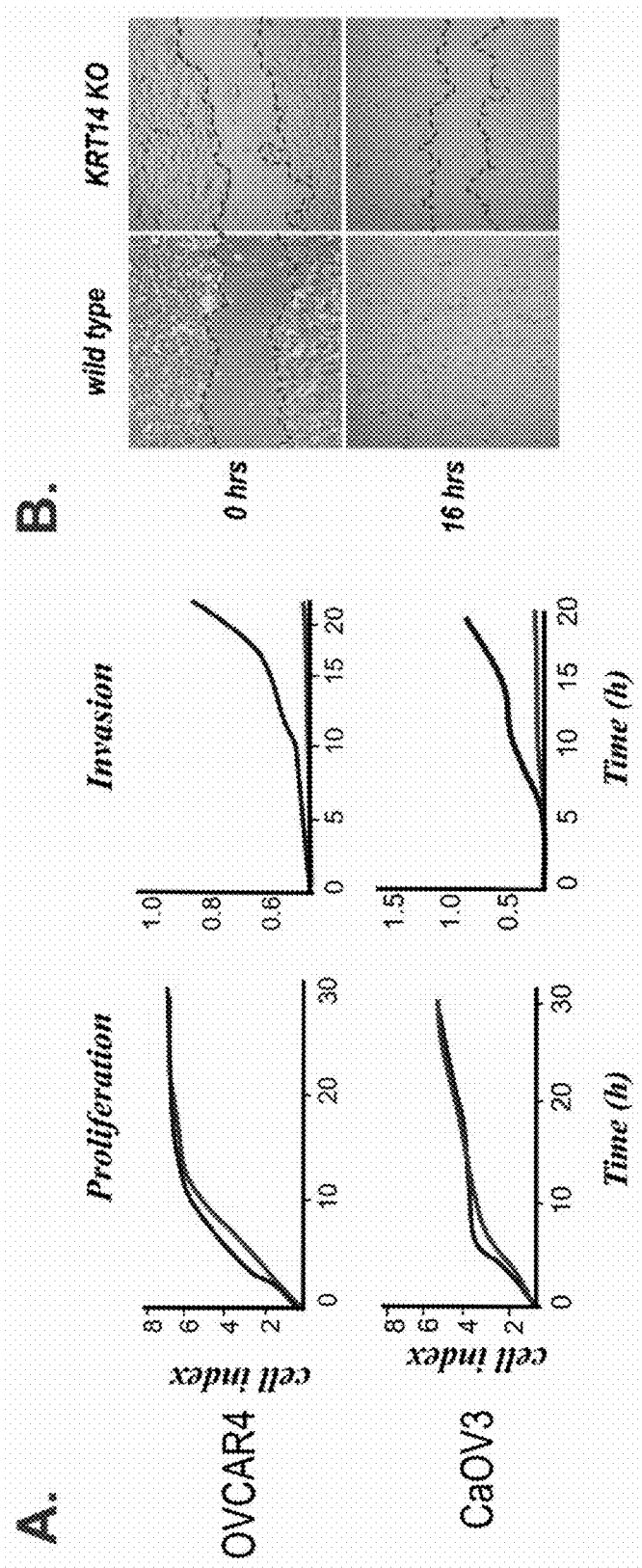
FIGS. 2A and 2B are graphical and photographical representations showing KRT14 expression required for migration and invasion of ovarian cancer cells in vitro. KRT14 gene expression was disrupted using CRISPR technology in ovarian cancer cell lines OVCAR4 and CaOV3. Representative experiments are shown.

Using a real-time in vitro invasion assay (Bilandzic and Stenvers (2014) *J Vis Exp* 87) to measure ovarian cancer cell invasion through a mesothelial monolayer, it was demonstrated that genetic ablation of KRT14(K14$^{KO}$) completely abrogated the invasive capacity of multiple ovarian cancer lines (CVAR4 and CaOV3 (FIGS. 2A-2B), as well as primary ovarian cancer cells (n=5) recovered from ascites fluid (data not shown). Loss of KRT14 expression had no effect on cell viability and proliferative capacity, consistent with other studies (Papafoliou et al. (2016) supra; Rock et al. (2009) *Proc Natl Acad Sci USA* 106(31):12771-12775). KRT14$^{KO}$ ovarian cancer cells were also unable to repair a damaged cell monolayer in wound healing assays, demonstrating a loss of migration competence (FIG. 2B). It was also observed that KRT14$^{KO}$ ovarian cancer cells, cultured as multicellular spheroids, displayed reduced binding to a mesothelial monolayer and failed to initiate mesothelial clearance (not shown), a key requirement for epithelial ovarian cancer (EOC) invasion (Iwanicki et al. (2011) *Cancer Discov* 1(2):144-157). In vivo studies using a syngeneic ovarian cancer mouse model (Roby et al. (2000) *Carcinogenesis* 21(4):585-591) demonstrated KRT14$^{KO}$ ovarian cancer cells implanted intrabursally into mice failed to establish tumors (FIGS. 3A-3C); and mice implanted with KRT14$^{KO}$ cells did not develop abdominal distension or any other symptoms.

Example 6

Migratory Cells Display Increased KRT14 Expression

KRT14 mRNA expression was measured in migratory cells from clinical specimens including: (i) primary tumor tissue; (ii) ascites-derived HGSC cells; and (iii) benign cells; (iv) histologically normal ovary; and (v) the target peritoneal cell layer LP9 alone (n=3 per group). All malignant cells expressed KRT14 at assay commencement, with no expression detected in benign fibroma, normal ovary or LP9 mesothelial cells. Consistent with cell lines, migratory cells were detected only in malignant samples (i.e. tumor tissue or ascites derived); cells isolated from benign ascites, normal controls or LP9 cells alone failed to invade. KRT14 expression was significantly enriched in invasive cells that had migrated into the lower chamber compared to pre-migratory samples in the primary tumor samples, with the ascites-derived ovarian cancer cell population displaying the highest levels of KRT14 mRNA. Together the data indicate that whilst KRT14 has no effect on cell viability or proliferation, it is specifically required to maintain invasive potential of the migratory cancer cell subset in vitro; and it is significantly enriched in actively migrating cells.

Example 7

KRT14 is Restricted to a Sub-Population of HGSC Cells that Influence Spheroid Assembly and Adhesion to the Mesothelium KRT14 abundance was determined and its localization in ovarian cancer cells (both immortalized and primary ascites-derived) by immunostaining. In monolayer culture KRT14 was restricted to a few isolated cells, whilst spheroids cultured under low adhesion conditions showed KRT14 immunostaining exclusively localized to the outer spheroid rim. The absence of internal KRT14 staining was not due to occlusion of antibodies from the spheroid, since an anti-N-cadherin antibody penetrated effectively to stain the entire spheroid. It was assessed whether KRT14 expression was required for spheroid formation in vitro by examining KRT14$^{KO}$ and KRT14 overexpression (KRT14$^{OE}$) lines. Wild-type OVCAR4 cells, and cells transfected with non-targeting CRISPR control, formed spheroids after 12 hours in low adhesion culture; by contrast, KRT14 knock-out cells remained largely dispersed after 12 hours. However, extended incubation (48 hours) resulted in the formation of spheroids that were of a comparable size and morphology to the control. Conversely KRT14$^{OE}$ lines rapidly formed dense and compact spheres and demonstrated visible outgrowth from the original sphere evident following a 12 hour culture period. Compared to untreated controls, KRT14$^{KO}$ spheroids had significantly reduced ability to adhere to a mesothelial monolayer in vitro.

Example 8

KRT14+ Cells Lead Invadopodia Formation and Mesothelial Clearance

When inoculated onto a mesothelial monolayer, wild-type HGSC spheroids exhibited outgrowth, mesothelial clearance and extensive deposition and migration within 24 hours. Cells over-expressing K14 rapidly dispersed and displaced the mesothelial layer; by contrast, KRT14$^{KO}$ cells failed to disrupt the mesothelial monolayer. To examine whether matrix type affected invasion, spheroids (both cell lines and ascites-derived HGSC cells) were embedded into either Matrigel or Collagen-I matrices and monitored for invadopodia outgrowth over time. KRT14+ Invadopodia emerged from wild-type spheroids after 12 hours in collagen I matrix, but required 48-72 hours (dependent on cell type) before becoming evident in Matrigel. Immunostaining showed that KRT14+ cells were specifically localized to the invadopodia, with non-invading spheroid core cells maintaining a KRT14-phenotype. This was confirmed in monolayer scratch assays, where KRT14+ cells were localized specifically at the areas of wound closure. Consistent with their lack of invasive capacity, KRT14$^{KO}$ cells failed to form visible invadopodia in either matrix. Together, the data suggest that KRT14 expression is a feature of actively invading cells, and that its loss significantly impedes the ability of spheroids to displace the mesothelium and disseminate during tumor outgrowth.

Example 9

KRT14 is Associated with Tumor Stage, and Negatively Predicts Progression Free Survival for Ovarian Cancer Patients To establish the clinical relevance of KRT14 expression, tissue microarrays (n=292) comprising multiple histological subtypes, grades and stages of ovarian cancers, as well as normal ovary and fallopian tube sections were stained for KRT14 abundance and localization. KRT14 expression was generally not detected in normal ovary (5%, 1/20) or fallopian tube (0%, 0/8) tissue, but was universally expressed by all ovarian cancer subtypes examined. Staining was localized to tumor epithelium, with little evidence of KRT14 in stromal tissue. In particular, KRT14 was detected in 100% of HGSC tissues, and was significantly elevated compared to normal ovary (p=0.0362, unpaired t-test with Tukeys post Hoc).

Potential associations between KRT14 expression and patient prognosis were then interrogated in 15 publically available ovarian cancer data sets [Lanczky et al. (2016) supra]. High KRT14 expression was associated with reduced progression-free survival (PFS) (HR 1.17; 95% CI 1.03-1.33 P<0.015), particularly for patients diagnosed with early-stage (Stages I-II) disease (HR 1.96; 95% CI 1.08-3.56 P<0.025). High KRT14 expression was also associated with reduced PFS following platinum and taxol based chemotherapy (HR 1.27; 95% CI 1.07-1.51 P<0.006), and was a negative predictor of PFS following optimal debulk (HR 1.24; 95% CI 1.03-1.5 P<0.026). Accordingly, patients with a shallow deletion in KRT14 were more sensitive to chemotherapy and exhibited improved response to primary therapy. Thus, KRT14 expression is an independent predictor of prognosis for patients with high grade serous ovarian cancers.

Example 10

Implantation into Mice

Figure 3:
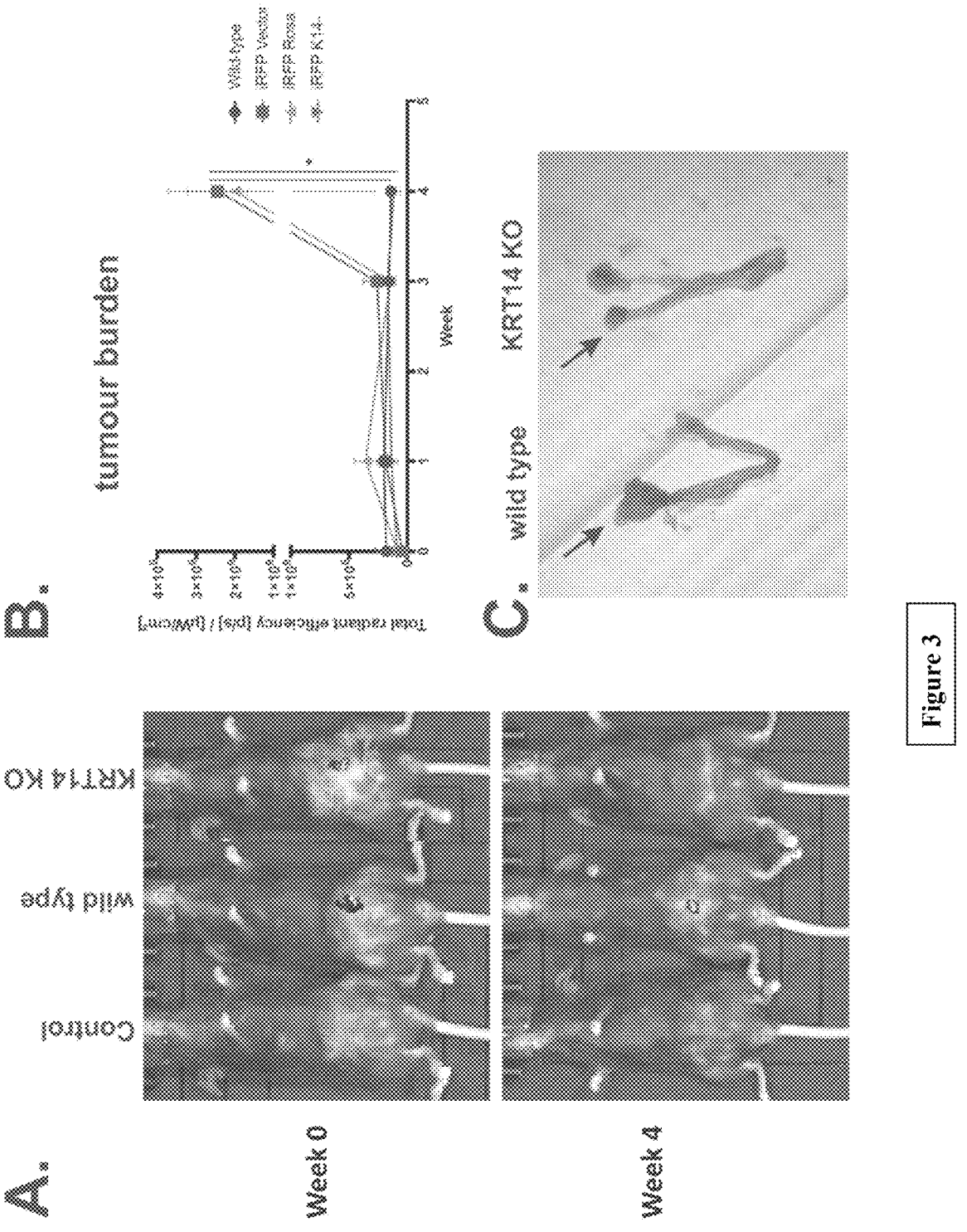
FIGS. 3A through 3C are photographic and graphical representations showing KRT14 expression required for successful tumor implantation in vivo. Murine ID8 ovarian cancer cells, either expressing ("wild-type"; WT) or lacking ("KRT14$^{KO}$") KRT14 expression, were implanted intraburally into wild-type C57BL/6 mice. Tumor growth was monitored in real time using in vivo fluorescence.

In mice implanted with KRT14$^{KO}$ cells no tumor deposits, or even fluorescent tumor cells, were detectible at autopsy suggesting that not only did tumors fail to implant, but were subsequently cleared following surgery (FIGS. 3A-3B). Using flow cytometry and immunocytochemical staining of intact cells, it was observed that the N terminus of KRT14 is exposed at the cell surface (FIGS. 4A-4B). Consistent with other studies (Papafotiou et al. (2016) supra; Rock et al. (2009) supra), KRT14+ cells represented only a subset of tumor cell population (FIG. 4A). Using polyclonal antibodies against either the N- or C-termini of KRT14, it was confirmed that antibodies against the N-terminus could prevent invasion in vitro, mimicking the effects of KRT14 gene knock-out (FIG. 4B). Anti-C-terminal antibodies had no effect on invasion, consistent with the well-established intracellular localization of the C-terminal region of KRT14 (FIG. 4B). Exogenously added full length, recombinant KRT14 protein could compete for antibody binding, and resorted invasion in vitro (FIG. 4B). Thus, loss of invasive capacity was directly due to binding of the antibody of KRT14. Moreover, this effect is mediated by antibody binding to the N-terminus of KRT14; and the N-terminus was exposed on the external side of cells, accessible to antibody binding.

Example 11

Antigenicity and Hydrophobicity Plots

Antigenicity and hydrophobicity plots were used to examine the first 200 amino acids of KRT14 in silico (FIG. 5A). Five potentially antigenic regions were predicted, and six peptides encompassing to these regions were synthesized for use in further competition assays. Blockade of the N-terminal antibody by peptides #4 and #5 restored invasion (FIG. 5B) and migration (FIG. 5C) of ovarian cancer cells in vitro. Peptides 1, 2, 3 and 6 failed to restore complete invasive and/or migratory capacity, despite recognition by polyclonal antibodies used. Based on antibody and peptide competition assays, the surface-exposed region of the KRT14 protein was defined within the amino sequence NH2-GFGGGYGG-GLGAGLGGGFGGGFAGGDGL (SEQ ID NO:1). This amino acid sequence has been used to immunize mice, for the production of monoclonal antibodies targeting the N-terminus of KRT14 in intact cells.

Example 12

Anti-Sera for KRT14

A functional test is used to assess in-house mouse anti-sera AN-17 O20023, generated by the inventors against a protein fragment containing the specified KRT14 epitope, for the ability for cancer cell invasion to be blockaded in vitro.

Real time invasion assays were conducted using an xCELLigence real time cell analysis (RTCA) DP 6-well instrument (ACEA Biosciences). Ovarian cancer cells (SKOV3) were synchronized in Go phase by incubation in serum-free media (SFM), and seeded (4×104 cells/well) in the upper chamber of a CIM-16 well plate coated with Matrigel matrix (1:10 in SFM; BD Biosciences, San Jose, CA). Media containing 10% v/v FBS was added to the lower chamber as a chemoattractant. Anti-sera from mouse AN-17 O20023 (diluted 1:100 in SFM), control serum or commercially available polyclonal antibody against KRT14 ((Sigma SAB4501657; 1 μg/ml in SFM) were added to the upper chamber, and invasion measurements taken every 15 minutes for 24 hours. Cell viability on completion of the assay was assessed by Alamar Blue stain. All assays were performed in duplicate. Anti-sera AN-17 O20023 were generated against a protein fragment containing the specified KRT14 epitope.

In untreated and serum-only control wells, invasion was observed within 5 hours of inoculation (FIG. 6A). Cells treated with commercially available polyclonal anti-KRT14 (Sigma SAB4501657; which can recognize the specified KRT14 epitope) showed inhibition of invasion. Anti-serum AN-17 O20023 effectively blocked invasion in vitro with similar efficacy to the purified anti-KRT14 polyclonal antibody (FIG. 6A), demonstrating its effective recognition of the target. There was no significant difference in viability at endpoint between untreated vs control or anti-serum-treated cells (FIG. 6B), suggesting the lack of invasion was not due to impaired proliferative capacity.

Anti-serum AN-17 O20023 effectively blocked ovarian cancer cell invasive capacity in vitro, with similar efficacy to a commercially purchased preparation. The effect was not due to impaired cell proliferation, but was specific to invasion as previously observed. This antibody is suitable for ongoing characterization as a lead compound.

Example 13

Effects on Non-Ovarian Cancer Cells

Anti-KRT14 antibodies were used to test whether they can prevent invasion by cancer cells derived from other (non-ovarian) solid tumor types.

In vitro wound repair assays were conducted using AN3CA endometrial carcinoma and SW620 colorectal carcinoma lines. Cells were grown in complete medium to confluency in a 12-well plate, then serum-starved overnight to synchronize at $G_0$. The following day cell culture medium was removed, and cell monolayers were wounded by scraping with a pipette tip attached to suction. Non-adherent cells were removed by gentle washes with PBS. Cells were incubated in complete growth medium+/−commercial KRT14 antibody (1 μg/ml) alone or in combination with 1 μg/ml competing peptides. The wound area was imaged under a phase microscope (Leica) at regular intervals ranging from 0-72 hours. Wound closure was measured in image series using AnalySIS LS Research Software (Olympus) to determine the area of the wound on each day. Experiments were repeated in triplicate with at least six wound areas observed per growth condition with the data from the 16 hour collection point demonstrated.

Both endometrial and colorectal carcinoma cell lines displayed impaired wound healing in the presence of anti-KRT14 antibody after 16 hours of culture (FIG. 7). In the presence of the competing KRT14 epitope, wound healing ability was restored to the level observed in untreated controls.

Anti-KRT14 antibody inhibits the migratory behavior of colorectal and endometrial cancer cell lines, similarly to inhibition observed ovarian carcinoma cells. Inhibition is specific for the defined KRT14 epitope, as evidenced by competition assay. The data suggest that antibody-mediated inhibition of KRT14 may act as a pan-cancer mechanism to inhibit invasion in multiple solid tumor types.

Example 14

Cross Species Effects of Antibodies

Anti-human KRT14 antibodies were assessed for their ability to prevent invasion in non-human ovarian cancer cells.

All experiments were carried out using the murine ID8 ovarian cancer cell line. Real-time invasion assays (as per Example 5) and in vitro wound repair assays (as per Example 6) were carried out as described.

Anti-KRT14 antibodies specific for the human KRT14 epitope effectively blocked the migration of mouse cancer cells in vitro (FIG. 8A). Peptide competition assays (as described in Example 6) restored migratory capacity in these cells (FIG. 8A), demonstrating specificity for the KRT14 epitope.

Real-time invasion assay confirmed that anti-KRT14 antibody blocked ID8 cell invasion in vitro (FIG. 8B), with similar efficacy to that observed in human cell lines.

The antigenic epitope of KRT14 demonstrates high homology (>80%) across multiple species. Accordingly, antibodies against the human epitope can effectively bind to non-human protein to inhibit cell migration and invasion in vitro. These data suggest that anti-KRT14 therapies will be applicable across species.

Example 15 mAb AN-17 Synergizes with Standard-of-Care Chemotherapy In Vitro

This study was undertaken to determine whether the targeting of cell-surface antigen KRT14 by monoclonal antibody AN-17 (mAb AN-17), which has been demonstrated to impair migration and invasion (as noted elsewhere herein) would sensitise ovarian cells to the standard first line chemotherapeutic agent, cisplatin.

Real time cell analysis (RTCA) was conducted as previously described (PMID: 31443478; Bilandzic et al., Cancers (Basel). 2019; 11(9), E1228) using an xCELLigence RTCA SP 96-well instrument (ACEA Biosciences). Cell lines were synchronized in $G_0$ by overnight incubation in serum-free media and were seeded at $0.5 \times 10^3$ cells/0.15 ml/per well. After 24 hours, a combination of either cisplatin alone (1.25 mg/ml), mAb AN-17 alone (1 ug/ml) or cisplatin plus mAb AN-17 was added. Impedance readings were taken every 15 minutes for the experimental duration. mAb AN-17 comprises the heavy chain variable region of SEQ ID NO:3 and the light chain variable region of SEQ ID NO:5, encoded by the nucleic acid sequences of SEQ ID NOs:2 and 4, respectively (see also FIGS. 21 and 22A-22B).

Cisplatin-treatment of cells at 15 μg/ml or 20 μg/ml resulted in complete cell death, whilst a dose of 1.25 μg/ml was sub-lethal and cells continued to proliferate (FIG. 9). As previously demonstrated, mAb AN-17 alone had no effect on cell viability or proliferation. However, co-incubation of cells with mAb AN-17 and cisplatin significantly reduced cell viability and proliferation compared to chemotherapy alone at every dose tested (FIG. 9). The most profound effect was observed when cisplatin was used at the sub-lethal dose of 1.25 μg/ml; co-incubation with mAb AN-17 resulted in complete cell death after ~50 hrs (FIG. 9), similar to the 12-fold higher cisplatin dose alone. Thus, mAb AN-17 acts to increase sensitivity of cells at least 10-fold to standard platinum chemotherapy in vitro.

Example 16 mAb AN-17 Displays No Detectible Cross-Reactivity Against a Panel of ~10,000 Antigens The following experiments were undertaken to establish whether mAb AN-17 displays any cross-reactivity against a panel of protein antigens.

Proteomic profiling of mAb AN-17 antibody reactivity was performed using Invitrogen™ ProtoArray™ Human Protein Microarrays v5.0 (ThermoFisher Scientific, Waltham MA), comprising 9,184 individual recombinant human proteins spotted in duplicate. All procedures were carried out as previously described (PMID: 29141850; Wilson et al. *Cancer Epidemiol Biomarkers Prev.* 2018; 27(2): 183-192). Arrays were probed using mAb AN-17 diluted 1:500 in wash buffer. Fluorescent detection antibody against IgG heavy and light chains was from Abcam (#ab150119 Goat Anti-Mouse IgG H&L Alexa Fluor® 647, preadsorbed) diluted to 2 mg/ml in wash buffer prior to use. A single array incubated with detection antibody alone was used as a control for non-specific antibody binding.

Array imaging was performed using a Fuji FLA5100 multi wavelength scanner as described (PMID: 29141850; Wilson et al. *Cancer Epidemiol Biomarkers Prev.* 2018; 27(2):183-192), using a 635 nm excitation laser and dual band pass Cy3/Cy5 filter. Images were acquired at 10 m resolution, with PMT set at 1000V. Array alignment, feature extraction and data normalization were performed as previously described (PMID: 29141850; Wilson et al. *Cancer Epidemiol Biomarkers Prev.* 2018; 27(2):183-192). Array co-ordinates were obtained from the manufacturer-provided downloadable .GAL files (ThermoFisher Scientific).

Individual array images showing antigen reactivity with either mAb AN-17 or secondary antibody alone are shown in FIG. 10. There were no significant differences between control and mAb AN-1-treated arrays, suggesting that mAb AN-17 did not react with any of the proteins present on the arrays tested.

These data demonstrate high specificity of mAb AN-17 for its target antigen (KRT14) in vitro. mAB AN-17 did not react with any of the antigens present on the array, including several related keratin proteins. mAb AN-17 therefore displays high affinity for its target antigen.

Example 17 mAb AN-17 Detects KRT14 by Western Blotting

A 1 μg aliquot of full-length recombinant KRT14 protein (Abcam #ab73637) was separated by SDS PAGE and transferred to PVDF membrane using standard procedures (PMID: 23952987). The membrane was probed with mAb AN-17 at dilutions of 1:1000, 1:5000 and 1:10,000. Secondary antibody was goat anti-mouse HRP conjugate (1:50, 000 dilution), with detection of KRT14 using chemiluminescence according to standard protocols (PMID: 23952987; Rainczuk et al., *J Proteome Res.* 2013; 12(9): 4074-88).

Full length KRT14 protein was successfully detected by western blotting using mAb AN-17 as the primary antibody (FIG. 11). Multiple dilutions gave strong signal.

Example 18 mAb AN-17 Identifies KRT14+ Leader Cells and Circulating Tumour Cells by Flow Cytometry Flow cytometry was carried out according to standard protocols (PMID: 30602661), with data acquired using a BD LSRFortessa X-20 (BD Biosciences) and analysed using FlowJo software v10.5.0 (BD Biosciences). Samples assessed for KRT14+ cell populations included OVCAR3, CAOV4, ID8 mouse ovarian cancer cells, ascites-derived ovarian cancer cells derived from a clinical specimen (designated #3.1937-07) and cardiac blood from a mice bearing 12-week old epithelial ovarian tumours. For cell lines, $1\times10^6$ cells per cell line were incubated with either mAb AN-17 (1:200 dilution) or a commercially available anti-KRT14 polyclonal antibody (Sigma SAB4501657; 1:50 dilution) as a positive control for 45 mins in non-immune serum at room temperature. The secondary antibodies, goat anti-mouse Alexa647 (mAb AN-17) or goat anti-rabbit IgG Alexa 488 (commercial Ab), were diluted 1:500 and incubated for 30 minutes. For blood samples, $2\times10^6$ cells were incubated with an Alexa Fluor®488-conjugated mAb AN-17 antibody for 45 minutes. Following PBS washes, cells were resuspended in PBS/2% FBS data was acquired using a BD LSRFortessa X-20 (BD Biosciences) flow cytometer.

Cells expressing KRT14 were detected by flow cytometry, with similar detection using mAb AN-17 compared to a commercially available polyclonal antibody, Sigma SAB4501657 (FIG. 12), in cell lines (human—OVCAR4, CAOV4; mouse—ID8) and clinically obtained ovarian cancer cells (3:19367-03).

Expression of extracellular KRT14 also marks the circulating tumour cell (CTC) population. Using a murine ovarian cancer model as previously described in PMID: 30602661 (Wilson et al. *Cancers (Basel).* 2018; 11(1), E32), CTCs obligately express the near infra-red fluorophore iRFP720. mAb AN-17 was used to probe whole blood from mice with ovarian cancer, and analysed by flow cytometry for KRT14+ iRFP+ cells. mAB AN-17 was able to correctly identify iRFP+ cells from whole blood, demonstrating its utility to identify and capture CTCs.

mAb AN-17 identified KRT14+ cells by flow cytometry, with comparable sensitivity to a commercially available anti-KRT14 polyclonal antibody (Sigma SAB4501657). Moreover, mAb AN-17 was able to detect and isolate KRT14+ CTCs by flow cytometry from mice bearing ID8 iRFP720+ epithelial ovarian tumours. Anti-KRT14 binding agents, such as mAb AN-17, thus have potential for use in diagnostic and/or prognostic testing, including the capture and analysis of CTCs. The data also indicated that anti-KRT14 binding agents, such as mAb AN-17, could be used to therapeutically target these cells in vivo.

Example 19 mAb AN-17 Detects KRT14+ Cells by Immunofluorescence Staining

The ovarian cancer cell lines SKOV-3, Ovcar4 and Cov362.3 were seeded onto 96 well black fluortrac imaging plates. Intact or fixed (1% paraformaldehyde; PFA) and permeabilized (0.1% Triton X) cells were stained using mAb AN-17. For fixed cells, samples were blocked in 10% fetal bovine serum (FBS) and then stained with 1 μg/ml mAb AN-17 for one hour at room temperature. Cells were subsequently washed with PBS and stained with the Alexa Fluor®-647 goat anti-mouse secondary at 1:2000 for one hour at room temperature. For intact cells, samples were stained with 1 μg/ml mAb AN-17 conjugated to Alexa-647 in PBS containing 1% FBS for two hours at 37° C., the medium was replaced with fresh PBS/1% FBS and cells were immediately imaged. Samples were imaged using the Cytation 3 multimode reader at 4× magnification.

Specific intracellular cytoplasmic localization for the mAb AN-17 was observed in permeabilized ovarian cancer cell line samples (FIG. 14). In intact live cells, a predominant cell surface localization for the mAb AN17 was observed.

These data show that mAb AN17 can be effectively used to stain for KRT14 in cells by immunofluorescence. Staining is effective in both live, intact cells, and in fixed and permeabilized cells.

Example 20 mAb AN-17 Detects KRT14+ Cells by Immunohistochemical Staining in Cancer Tissue Sections Immunohistochemistry on formalin-fixed, paraffin-embedded (FFPE) samples was performed using standard protocols (PMID: 31443478; Bilandzic et al., *Cancers (Basel)*. 2019; 11(9), E1228). The efficacy of mAb AN-17 was tested across a range of concentrations (2 µg/ml-0.25 µg/ml) and compared to a commercially available anti-KRT14 antibody (Sigma SAB4501657, 1:100 dilution) and a mouse IgG control following an overnight incubation. Following incubation with secondary antibodies, as described, antibody binding and localization were visualized as a brown precipitate using a Vectastain Elite ABC kit according to the manufacturer's instructions (Vector Laboratories, Burlingame, CA, USA).

Tissue stained using mAb A-17 showed an identical localization to the commercial anti-KRT14 polyclonal antibody (Sigma SAB4501657), with staining observed specifically in the tumour epithelium (FIG. 15). There was little evidence of staining observed in the stromal tissue, and no staining observed for the mouse Ig G control. Signal abundance was less diffuses when compared to the commercially available polyclonal antibody (Sigma SAB4501657).

These data show that mAb AN-17 can be effectively used to localize KRT14 in sectioned tumour tissues.

Example 21 mAb AN-17 has No Detectible Acute Toxicity In Vivo

Induction of ovarian tumours; Murine ID8 ovarian tumour cells were implanted intrabursally in C57BL/6 mice, and primary tumours allowed to develop over a period of ~4 weeks as previously described (PMID: 30602661; Wilson et al. *Cancers (Basel)*. 2018; 11(1), E32).

Assessment of mAb AN-17 toxicity; Mice (n=2/dose/time point) received a single dose of either mAb AN-17 or an isotype-matched control IgG kappa antibody (Ultra-LEAF™ Purified Mouse IgG1, κ Isotype Ctrl, Biolegend #401411) by intraperitoneal injection, and were then monitored over a period of up to 7 days for any clinical signs associated with toxicity. Doses of 0.5, 1.0. 2.5, 5.0 and 10 mg/kg were assessed. After 7 days mice were culled, and examined post mortem for any evidence of toxicity (macroscopic tissue appearance, presence of inflammation, or any obvious lesions).

All mice (tumour and non-tumour) were assessed for evidence of toxic effects (initial reaction following injection, signs of distress) over the experimental period, and for evidence of toxicity as post mortem (as above). No evidence of toxic effects was noted at any time point, or for any dose tested.

Example 22 mAb AN-17 Localizes Specifically to Tumour Tissue and is not Retained in Healthy Tissue In Vivo mAb AN-17 or an isotype-matched control IgG kappa antibody (Ultra-LEAF™ Purified Mouse IgG1, κ Isotype Ctrl, Biolegend #401411) were labelled with either ALEXA647 or ALEXA750 fluorescent dye (Thermo Fischer Scientific) at a 1:10 ratio, according to the manufacturer's instructions. Mice (n=2/group) received either ALEXA-labelled mAb AN-17 or isotype control IgGκ (as above) at 0.5, 1.0, 2.5, 5.0 or 10.0 mg/kg by intraperitoneal (100 µl) injection. Control mice received vehicle (PBS) alone. At time points from 4 hr to 7 days post-injection, mice were culled and selected tissues (liver, kidney, spleen, intestine, ovary+fallopian tube/ovarian tumour (as relevant), brain, heart, lung) were harvested. Tissue distribution and clearance were assessed by ALEXA647 or ALEXA750 fluorescence using an IVIS Lumina III Imaging System (Perkin Elmer). Bright-field (auto-exposure) and fluorescence imaging (ALEXA647 ex640, em670; or ALEXA750 ex740, em790 nm). Spectral unmixing and image analysis were performed as previously described (PMID: 30602661; Wilson et al., *Cancers (Basel)*. 2018 Dec. 31; 11(1), E32). Background average radiant efficiency from vehicle-treated animals were subtracted from fluorescence measurements in each case, and the resulting data plotted for comparison.

The localization of mAb AN-17 in healthy tissues (using mice without ovarian tumours) over a 7 day period was compared to a non-targeted isotype control antibody, following administration of a single dose of 0.5 mg/kg. In each case, antibodies were fluorescently labelled to facilitate detection post mortem. Antibody-associated fluorescence was observed in intestine, reproductive organs, liver, kidney, spleen, lung and heart; no fluorescence was detected in brain (FIGS. 16A-16D). However, there was no significant difference between mAb AN-17 and isotype control IgGκ antibody, demonstrating no specific accumulation of mAb AN-17 in any of the healthy tissues examined. Moreover, by day 7, each antibody had been largely cleared from all organs (as judged by loss of fluorescent signal) suggesting that mAb AN-17 was not retained long-term (FIGS. 16A-16D).

Since antibody clearance at the low dose appeared to be complete by day 7, mAb AN-17 clearance from healthy tissues was evaluated at multiple increasing doses (from 0.5 mg/kg to 10 mg/kg) in a similar manner. Even at the highest dose (10 mg/kg), mAb AN-17 was virtually undetectable in all organs after 7 days, and was typically present at a lower level than the control antibody (FIGS. 17A-17D). These data suggest that mAb AN-17 does not exhibit non-selective accumulation or retention in healthy tissues.

The distribution of mAb AN-17 was then evaluated in mice with primary ovarian tumours, using single doses of 5 mg/kg and 10 mg/kg. Evaluation was performed over a period of 7 days. At 24 hours post-administration, mAb AN-17 was strongly localized to tumour tissue (FIGS. 18A-18C). Unlike in healthy tissue, mAb AN-17 persisted in tumour tissue and remained detectible even after 7 days (FIGS. 18A-18C). A higher fluorescence yield was initially observed in mice that received the 10 mg/kg dose; however, by day 3 post-injection a similar level of mAb AN-17 was detected regardless of dose, suggesting that tumours may have been saturated at the 5 mg/kg dose. Moreover, initial levels of mAb AN-17 detection were 2 orders of magnitude higher in tumour tissue than were detected in the reproductive tract of mice that did not have tumours (compare FIGS. 18A-18C).

These data show that mAb AN-17 is specific for tumour tissue and persists at the tumour site for at least 1 week following administration.

The data presented herein demonstrate that mAb AN-17 has high specificity for its target (KRT14), minimal off-target effects and low retention in non-target tissues. In healthy, non-tumour bearing mice, mAb AN-17 did not display any specific retention in healthy organs and appeared to be rapidly cleared. By contrast, mAb AN-17 was specifically detected associated with ovarian tumours where it persisted for at least 1 week. There was no toxicity noted at any dose or any time point, suggesting that the high specificity of mAb AN-17 confers a favourable safety profile when injected. Moreover, a maximum tolerated dose was not reached. mAb AN-17 thus has good safety profile and high in vivo specificity for tumour tissue.

Example 23 mAb AN-17 Treatment Successfully Regresses Established Ovarian Tumours In Vivo

The purpose of these experiments was to establish whether mAb AN-17 can be used to influence tumour progression in a model of established, primary malignancy in a syngeneic mouse model.

Murine ID8 ovarian tumour cells were implanted intra-bursally in C57BL/6 mice, and primary tumours allowed to develop over a period of ~4 weeks as previously described (PMID: 30602661). Mice with primary tumours (n=10/group) received mAb AN-17 at 5 mg/kg by intraperitoneal injection bi-weekly, for a period of 3 weeks. Control animals received an equivalent dose of isotype-matched control IgG kappa antibody (Control Group 1); or and equivalent volume of vehicle (PBS) alone (Control Group 2). Following 3 weeks of bi-weekly treatment (Mondays and Thursdays), all mice were culled and assessed for tumour size and weight. Two additional, non-tumour bearing animals were used as non-surgical controls.

Bi-weekly administration of mAb AN-17 had no observable adverse effects on animals, as previously indicated by single dose experiments (above). Following 3 weeks of continued treatment, all mice were culled and the influence of mAb AN-17 administration on tumour size assessed. In mice treated with vehicle alone (Control Group 2), 6/10 animals (60%) had primary ovarian tumours (FIG. 19); similarly, 6/10 animals (60%) of mice treated with isotype control antibody (Control Group 1) also had primary tumours demonstrating that the non-targeted antibody had no influence on tumour progression.

When mice that received mAb AN-17 were analysed, no tumours could be identified either in or on the right ovary (the implantation site), nor anywhere else in the animals (FIG. 19). Moreover, ovaries extracted from these mice appeared healthy and had no observable morphological difference to untreated, non-surgical controls.

Treatment of mice with mAb AN-17 resulted in the complete regression of established, primary ovarian tumours to an undetectable level after 3 weeks. There were no adverse effects noted during the treatment period, suggesting that administration of mAb AN-17 is a safe and highly efficacious therapeutic approach to treat established solid tumours in vivo.

Example 24 mAb AN-17 Blocks Migration and Invasion in Multiple Cancer Cells

The experiments outlined above demonstrated antibody-specific inhibition of cell migration and invasion by mAb AN-17 in ovarian, colorectal and endometrial cancer cell lines. The following experiments were undertaken to investigate the effect of mAb AN-17 on the migration and invasion of other cancer cell types.

In vitro wound repair assays were conducted on the following cancer cell lines: BT16 atypical teratoid rhabdoid (brain) carcinoma, NCI-H1573 lung adenocarcinoma, SJ-GBM2 primary glioblastoma multiforme, AN3CA endometrial carcinoma, SW620 colorectal carcinoma and MDA-MB-468 breast carcinoma. Cells were grown in complete medium to confluency in a 12-well plate, and subsequently serum-starved overnight to synchronize at $G_0$. The following day, cell culture medium was removed and the cell monolayers were wounded by scraping with a pipette tip attached to suction. Non-adherent cells were removed by gentle washes with phosphate buffered saline (PBS) and complete growth medium was added to each well, in either the absence or presence of mAb AN-17 (at 1 μg/ml). The wound area was imaged every hour for 0-24 hours. Wound closure was measured in image series using AnalySIS LS Research Software (Olympus) to determine the area of the wound on each day. Experiments were repeated in triplicate with at least six wound areas observed per growth condition.

As shown in FIGS. 23A-23F, when challenged using an in vitro wound repair assay, untreated cells were able to migrate and close the wound after 16 hrs. By contrast, all cell lines treated with mAb AN-17 failed to close the wound under the same conditions. These data demonstrate that mAb AN-17 inhibits cell migration and invasion of cancer cells, commensurate with the previous data showing similar effects in colorectal, endometrial and multiple ovarian cancer cell lines.

These data show that antagonists of KRT14 inhibit the migratory behaviour of multiple cancer cell types, including at least ovarian, endometrial, brain, lung, breast cancer cells. The disparate nature of these cancer types suggests that antagonists of KRT14, such as mAb AN-17, target a highly conserved pathway in cancer cells and are therefore applicable to the diagnosis, prognosis and treatment of multiple tumour types.

Those skilled in the art will appreciate that the disclosure described herein is susceptible to variations and modifications other than those specifically described. It is to be understood that the disclosure contemplates all such variations and modifications. The disclosure also enables all of the steps, features, compositions and compounds referred to or indicated in this specification, individually or collectively, and any and all combinations of any two or more of the steps or features or compositions or compounds.

BIBLIOGRAPHY

Altschul et al. (1997) *Nucl. Acids. Res.* 25:3389
Ausubel et al. (1994-1998) In: *Current Protocols in Molecular Biology*, John Wiley & Sons Inc.
Bilandzic et al. (2009) *Mol Endocrinol,* 23(4):539-48
Bilandzic et al. (2013) *Mol Endocrinol,* 2013. 27(3):466-79
Bilandzic et al. (2014) *Cancer Lett* 354(1):107-114
Bilandzic and Stenvers (2014) *J Vis Exp* 87
Burleson et al. (2006) *J Transl Med* 4:6
Cheah et al. (2015) *Proc Natl Acad Sci USA* 112(15):4725-4730
Cheung et al. (2013) *Cell* 155(7):1639-1651
Cheung et al. (2016) *Proc Natl Acad Sci USA* 113(7):E854-863
Chothia et al. (1987) *J. Mol. Biol.* 196:901
Chothia et al. (1989) *Nature* 342:877-883
Chu et al. (2001) *Histopathology* 39(1):9-16

Coligan et al. *Current Protocols in Immunology,* 1991-1997

Cong et al. (2013) *Science* 339(6121):819-23

Domcke et al. (2013) *Nat Commun* 4:2126

Ewert et al. (2002) *Biochemistry* 41:3628-2636

Greenberg et al. (1995) *Nature* 374:168-173

Gefter et al. (1977) *Somatic Cell Genet.* 3:231-236

Ho et al. (2012) *Nat Rev Urol* 9(10):583-594

Iwanicki et al. (2011) *Cancer Discov* 1(2):144-157

Jones et al. (1986) *Nature* 321:522-525

Kenny et al. (20017) *Int J Cancer* 121(7):1463-72

Kim et al. (2014) *Obstet Gynecol Sci* 0.57(5):343-57

Kohler et al. (1975) *Nature* 256:495-499

Kohler et al. (1976) *Eur. J. Immunol.* 6(7):511-519

Kozbor et al. (1986) *Methods in Enzymology* 121:140

Lanczky et al. (2016) *Breast Cancer Res Treat.* 3 (160):439-446

Latifi et al. (2012) *PLoS ONE* 7(10)

Liu et al. (1987) *Proc. Natl. Acad. Sci. USA* 84:3439-3443

Liu et al. (2013) *Clin Cancer Res* 19(18):5053-67

Nguyen-Ngoc et al. (2012) *Proc Natl Acad Sci USA.* 109 (39):E2595-604

Nuttall et al. (2001) *Mol Immunol* 38:313-326

Nuttall et al. (2002) *FEBS Lett* 516:80-86

Nuttall et al. (2003) *Eur J Biochem* 270:3543-3554

Nuttall et al. (2004) *Proteins* 55:187-197

Padlan (1994) *Mol Immunol* 31:169-217

Papafotiou et al. (2016) *Nat Commun* 7:11914

Paraskevopoulou et al. (2016) *Cell Cycle* 15(23):3161-3162

Rainczuk et al. (2013) *J Proteome Res*

Rainczuk et al. (2014) *Int J Cancer* 134(3):530-41

Richmann et al. (1988) *Nature* 332:323-327

Richards (2013) *ISRN Inflammation* 2013: 23

Roby et al. (2000) *Carcinogenesis* 21(4):585-591

Rock et al. (2009) *Proc Natl Acad Sci USA* 106(31):12771-12775

Roux et al. (1998) *Proc Natl Acad Sci USA* 95:11804-11809

Salamonsen et al. (2013) *Fertil Steril* 99(4):1086-92

Shulman et al. (1978) *Nature* 276:269-270

Sodek et al. (2012) *Cancer Metastasis Rev* 31(1-2):397-414

Stanfield et al. (2004) *Science* 305:1770-1773

Streltsov et al. (2004) *Proc Natl Acad Sci USA* 101:12444-12449

Streltsov et al (2005) *Protein Sci* 14:2901-2909

Toyama et al. (1987) *Monoclonal Antibody, Experiment Manual*, published by Kodansha Scientific)

Trowbridge (1982) *J. Exp. Med.* 148(1):220-227

Vaughan et al. (2011) *Nat Rev Cancer* 11(10):719-925

Verhoeyen et al. (1988) *Science* 239:1534-1536

Vesci et al. (2014) *Int J Oncol* 45(4):1421-9

Volk et al. (1982) *J. Virol.* 42(1):220-227

Volkmer et al. (2012) *Proc Natl Acad Sci USA* 109(6):2078-2083

The invention claimed is:

1. A method for the treatment of a keratin-14 (KRT14)-positive cancer in a mammalian subject, said method comprising administering to said subject an amount of an antibody or antigen-binding fragment thereof that binds specifically to an extracellular portion of keratin-14 (KRT14) on cancer cells, wherein the antibody or antigen-binding fragment thereof comprises an immunoglobulin heavy chain variable domain (VH) and an immunoglobulin light chain variable domain (VL), wherein the VH comprises a complementarity determining region 1 (VH CDR1) comprising the amino acid sequence of SEQ ID NO:6, a VH CDR2 comprising the amino acid sequence of SEQ ID NO:7 and a VH CDR3 comprising the amino acid sequence of SEQ ID NO:8; and wherein the VL comprises a VL CDR1 comprising the amino acid sequence of SEQ ID NO:9, a VL CDR2 comprising the amino acid sequence of SEQ ID NO: 10, and a VL CDR3 comprising the amino acid sequence of SEQ ID NO:11, the amount effective to prevent or reduce cancer cell invasion, migration and/or metastasis, thereby treating the KRT14-positive cancer in the subject.

2. The method of claim 1 wherein the cancer is a gynecological cancer.

3. The method of claim 2 wherein the gynecological cancer is ovarian cancer or a stage or form of ovarian cancer.

4. The method of claim 1 wherein the antibody or antigen-binding fragment thereof is conjugated to a cytotoxic molecule.

5. The method of claim 1, wherein the VH comprises:
(a) a VH framework region 1 (FR1) comprising an amino acid sequence having at least 80% sequence identity to SEQ ID NO: 12;
(b) a VH FR2 comprising an amino acid sequence having at least 80% sequence identity to SEQ ID NO: 13;
(c) a VH FR3 comprising an amino acid sequence having at least 80% sequence identity to SEQ ID NO: 14; and
(d) a VH FR4 comprising an amino acid sequence having at least 80% sequence identity to SEQ ID NO: 15; and the VL comprises:
(e) a VL FR1 comprising an amino acid sequence having at least 80% sequence identity to SEQ ID NO: 16;
(f) a VL FR2 comprising an amino acid sequence having at least 80% sequence identity to SEQ ID NO: 17;
(g) a VL FR3 comprising an amino acid sequence having at least 80% sequence identity to SEQ ID NO:18; and (h) a VL FR4 comprising an amino acid sequence having at least 80% sequence identity to SEQ ID NO: 19.

6. The method of claim 5, wherein:
(a) the VH comprises the amino acid sequence of SEQ ID NO:3, and
(b) the VL comprises the amino acid sequence of SEQ ID NO:5.

7. The method of claim 1, further comprising administering to the subject, simultaneously or sequentially, an additional anti-cancer agent and/or exposing the subject to immunotherapy, radiation therapy, and/or surgical intervention.

8. The method of claim 7, wherein the additional anti-cancer agent is selected from the group consisting of dactinomycin, daunorubicin, doxorubicin (adriamycin), idarubicin and mitoxantrone, a platinum based agent, an antimetabolite, primed T-cells, and a cytokine.

9. The method of claim 8, wherein the antimetabolite is selected from the group consisting of azaserine, D-cycloserine, nycophenolic acid, trimethoprim, 5-fluorouracil, capecitabine, methotrexate, gemcitabine, cytarabine (ara-C) and fludarabine.

10. A pharmaceutical composition comprising an antibody or antigen-binding fragment thereof that binds specifically to an extracellular portion of keratin-14 (KRT14) on cancer cells, wherein the antibody or antigen-binding fragment thereof comprises an immunoglobulin heavy chain variable domain (VH) and an immunoglobulin light chain variable domain (VL), wherein the VH comprises a complementarity determining region 1 (VH CDR1) comprising the amino acid sequence of SEQ ID NO:6, a VH CDR2 comprising the amino acid sequence of SEQ ID NO:7 and a VH CDR3 comprising the amino acid sequence of SEQ ID NO:8; and wherein the VL comprises a VL CDR1 comprising the amino acid sequence of SEQ ID NO:9, a VL CDR2 comprising the amino acid sequence of SEQ ID NO: 10, and a VL CDR3 comprising the amino acid sequence of SEQ ID NO:11, and wherein said antibody or antigen-binding fragment thereof directly induces cytotoxicity or cytostasis of the cancer cells.

11. A diagnostic reagent comprising an antibody or antigen-binding fragment thereof that binds specifically to an extracellular portion of keratin-14 (KRT14) on cancer cells, wherein the antibody or antigen-binding fragment thereof comprises an immunoglobulin heavy chain variable domain (VH) and an immunoglobulin light chain variable domain (VL), wherein the VH comprises a complementarity determining region 1 (VH CDR1) comprising the amino acid sequence of SEQ ID NO:6, a VH CDR2 comprising the amino acid sequence of SEQ ID NO:7 and a VH CDR3 comprising the amino acid sequence of SEQ ID NO:8; and wherein the VL comprises a VL CDR1 comprising the amino acid sequence of SEQ ID NO:9, a VL CDR2 comprising the amino acid sequence of SEQ ID NO: 10, and a VL CDR3 comprising the amino acid sequence of SEQ ID NO:11, and wherein the antibody or antigen-binding fragment thereof is conjugated to a reporter molecule.

12. A method for detecting circulating KRT14-positive cancer cells in a patient, the method comprising:
   (a) providing a blood sample from the patient;
   (b) contacting the blood sample with an antibody or antigen-binding fragment thereof that binds specifically to an extracellular portion of keratin-14 (KRT14) on cancer cells, wherein the antibody or antigen-binding fragment thereof comprises an immunoglobulin heavy chain variable domain (VH) and an immunoglobulin light chain variable domain (VL), wherein the VH comprises a complementarity determining region 1 (VH CDR1) comprising the amino acid sequence of SEQ ID NO:6, a VH CDR2 comprising the amino acid sequence of SEQ ID NO:7 and a VH CDR3 comprising the amino acid sequence of SEQ ID NO:8; and wherein the VL comprises a VL CDR1 comprising the amino acid sequence of SEQ ID NO:9, a VL CDR2 comprising the amino acid sequence of SEQ ID NO: 10, and a VL CDR3 comprising the amino acid sequence of SEQ ID NO:11 to determine the presence of KRT14 positive cancer cells in the sample.

13. An antibody or antigen-binding fragment thereof that binds specifically to an extracellular portion of keratin-14 (KRT14) on cancer cells, wherein the antibody or antigen-binding fragment thereof comprises an immunoglobulin heavy chain variable domain (VH) and an immunoglobulin light chain variable domain (VL), wherein the VH comprises a complementarity determining region 1 (VH CDR1) comprising the amino acid sequence of SEQ ID NO:6, a VH CDR2 comprising the amino acid sequence of SEQ ID NO:7 and a VH CDR3 comprising the amino acid sequence of SEQ ID NO:8; and wherein the VL comprises a VL CDR1 comprising the amino acid sequence of SEQ ID NO:9, a VL CDR2 comprising the amino acid sequence of SEQ ID NO: 10, and a VL CDR3 comprising the amino acid sequence of SEQ ID NO:11.

14. The antibody or antigen-binding fragment thereof of claim 13, wherein the VH comprises:
   (a) a VH framework region 1 (FR1) comprising an amino acid sequence having at least 80% sequence identity to SEQ ID NO: 12;
   (b) a VH FR2 comprising an amino acid sequence having at least 80% sequence identity to SEQ ID NO: 13;
   (c) a VH FR3 comprising an amino acid sequence having at least 80% sequence identity to SEQ ID NO: 14; and
   (d) a VH FR4 comprising an amino acid sequence having at least 80% sequence identity to SEQ ID NO: 15;
   and the VL comprises:
   (e) a VL FR1 comprising an amino acid sequence having at least 80% sequence identity to SEQ ID NO: 16;
   (f) a VL FR2 comprising an amino acid sequence having at least 80% sequence identity to SEQ ID NO: 17;
   (g) a VL FR3 comprising an amino acid sequence having at least 80% sequence identity to SEQ ID NO: 18; and
   (h) a VL FR4 comprising an amino acid sequence having at least 80% sequence identity to SEQ ID NO: 19.

15. The antibody or antigen-binding fragment thereof of claim 14, wherein:
   (a) the VH comprises the amino acid sequence of SEQ ID NO:3, and
   (b) the VL comprises the amino acid sequence of SEQ ID NO:5.

* * * * *

```
                            SEQUENCE LISTING

<160> NUMBER OF SEQ ID NOS: 19

<210> SEQ ID NO 1
<211> LENGTH: 28
<212> TYPE: PRT
<213> ORGANISM: Homo sapiens

<400> SEQUENCE: 1

Gly Phe Gly Gly Gly Tyr Gly Gly Gly Leu Gly Ala Gly Leu Gly Gly
1               5                   10                  15

Gly Phe Gly Gly Gly Phe Ala Gly Gly Asp Gly Leu
            20                  25

<210> SEQ ID NO 2
<211> LENGTH: 354
<212> TYPE: DNA
<213> ORGANISM: Mus musculus

<400> SEQUENCE: 2
caggtgcagc tgaaggagtc aggacctggc ctggtggcac cctcacagag cctgtccatc      60
acatgcactg tctctgggtt ctcattatcc agatatagtg tacactgggt tcgccagcct     120
ccaggaaagg gtctggagtg gctgggaatg atatggggtg gtggaagcac agactataat     180
tcagctctca aatccagact gagcatcagc aaggacaact ccaagagcca agttttctta     240
aaaatgaaca gtctgcaaac tgatgacaca gccatgtact actgtgccag aaaagactac     300
ggctactcct actttgacta ctggggccaa ggcaccactc tcacagtctc ctca           354

<210> SEQ ID NO 3
<211> LENGTH: 118
<212> TYPE: PRT
<213> ORGANISM: Mus musculus

<400> SEQUENCE: 3

Gln Val Gln Leu Lys Glu Ser Gly Pro Gly Leu Val Ala Pro Ser Gln
1               5                   10                  15
```

-continued

```
Ser Leu Ser Ile Thr Cys Thr Val Ser Gly Phe Ser Leu Ser Arg Tyr
            20              25              30

Ser Val His Trp Val Arg Gln Pro Pro Gly Lys Gly Leu Glu Trp Leu
            35              40              45

Gly Met Ile Trp Gly Gly Gly Ser Thr Asp Tyr Asn Ser Ala Leu Lys
    50              55              60

Ser Arg Leu Ser Ile Ser Lys Asp Asn Ser Lys Ser Gln Val Phe Leu
65              70              75              80

Lys Met Asn Ser Leu Gln Thr Asp Asp Thr Ala Met Tyr Tyr Cys Ala
                85              90              95

Arg Lys Asp Tyr Gly Tyr Ser Tyr Phe Asp Tyr Trp Gly Gln Gly Thr
            100             105             110

Thr Leu Thr Val Ser Ser
        115
```

<210> SEQ ID NO 4
<211> LENGTH: 363
<212> TYPE: DNA
<213> ORGANISM: Mus musculus

<400> SEQUENCE: 4

```
gatgttttga tgacccaaac tccactctcc ctgcctgtca gtcttggaga tcaagcctcc      60
atctcttgca gatctagtca gagcattgta catagtaatg aaacaccta tttagaatgg     120 tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttcca     300
ttcacgttcg gctcggggac aaagttggaa ataaaacggg ctgatgctgc accaactgta     360
tcc                                                                   363
```

<210> SEQ ID NO 5
<211> LENGTH: 121
<212> TYPE: PRT
<213> ORGANISM: Mus musculus

<400> SEQUENCE: 5

```
Asp Val Leu Met Thr Gln Thr Pro Leu Ser Leu Pro Val Ser Leu Gly
1               5               10              15

Asp Gln Ala Ser Ile Ser Cys Arg Ser Ser Gln Ser Ile Val His Ser
            20              25              30

Asn Gly Asn Thr Tyr Leu Glu Trp Tyr Leu Gln Lys Pro Gly Gln Ser
            35              40              45

Pro Lys Leu Leu Ile Tyr Lys Val Ser Asn Arg Phe Ser Gly Val Pro
    50              55              60

Asp Arg Phe Ser Gly Ser Gly Ser Gly Thr Asp Phe Thr Leu Lys Ile
65              70              75              80

Ser Arg Val Glu Ala Glu Asp Leu Gly Val Tyr Tyr Cys Phe Gln Gly
                85              90              95

Ser His Val Pro Phe Thr Phe Gly Ser Gly Thr Lys Leu Glu Ile Lys
            100             105             110

Arg Ala Asp Ala Ala Pro Thr Val Ser
        115             120
```

<210> SEQ ID NO 6
<211> LENGTH: 8

```
<212> TYPE: PRT
<213> ORGANISM: Mus musculus

<400> SEQUENCE: 6

Gly Phe Ser Leu Ser Arg Tyr Ser
1               5

<210> SEQ ID NO 7
<211> LENGTH: 7
<212> TYPE: PRT
<213> ORGANISM: Mus musculus

<400> SEQUENCE: 7

Ile Trp Gly Gly Gly Ser Thr
1               5

<210> SEQ ID NO 8
<211> LENGTH: 12
<212> TYPE: PRT
<213> ORGANISM: Mus musculus

<400> SEQUENCE: 8

Ala Arg Lys Asp Tyr Gly Tyr Ser Tyr Phe Asp Tyr
1               5                   10

<210> SEQ ID NO 9
<211> LENGTH: 11
<212> TYPE: PRT
<213> ORGANISM: Mus musculus

<400> SEQUENCE: 9

Gln Ser Ile Val His Ser Asn Gly Asn Thr Tyr
1               5                   10

<210> SEQ ID NO 10
<211> LENGTH: 3
<212> TYPE: PRT
<213> ORGANISM: Mus musculus

<400> SEQUENCE: 10

Lys Val Ser
1

<210> SEQ ID NO 11
<211> LENGTH: 9
<212> TYPE: PRT
<213> ORGANISM: Mus musculus

<400> SEQUENCE: 11

Phe Gln Gly Ser His Val Pro Phe Thr
1               5

<210> SEQ ID NO 12
<211> LENGTH: 25
<212> TYPE: PRT
<213> ORGANISM: Mus musculus

<400> SEQUENCE: 12

Gln Val Gln Leu Lys Glu Ser Gly Pro Gly Leu Val Ala Pro Ser Gln
1               5                   10                  15

Ser Leu Ser Ile Thr Cys Thr Val Ser
            20                  25

<210> SEQ ID NO 13
```

-continued

```
<211> LENGTH: 17
<212> TYPE: PRT
<213> ORGANISM: Mus musculus

<400> SEQUENCE: 13

Val His Trp Val Arg Gln Pro Pro Gly Lys Gly Leu Glu Trp Leu Gly
1               5                   10                  15

Met

<210> SEQ ID NO 14
<211> LENGTH: 38
<212> TYPE: PRT
<213> ORGANISM: Mus musculus

<400> SEQUENCE: 14

Asp Tyr Asn Ser Ala Leu Lys Ser Arg Leu Ser Ile Ser Lys Asp Asn
1               5                   10                  15

Ser Lys Ser Gln Val Phe Leu Lys Met Asn Ser Leu Gln Thr Asp Asp
            20                  25                  30

Thr Ala Met Tyr Tyr Cys
        35

<210> SEQ ID NO 15
<211> LENGTH: 11
<212> TYPE: PRT
<213> ORGANISM: Mus musculus

<400> SEQUENCE: 15

Trp Gly Gln Gly Thr Thr Leu Thr Val Ser Ser
1               5                   10

<210> SEQ ID NO 16
<211> LENGTH: 26
<212> TYPE: PRT
<213> ORGANISM: Mus musculus

<400> SEQUENCE: 16

Asp Val Leu Met Thr Gln Thr Pro Leu Ser Leu Pro Val Ser Leu Gly
1               5                   10                  15

Asp Gln Ala Ser Ile Ser Cys Arg Ser Ser
            20                  25

<210> SEQ ID NO 17
<211> LENGTH: 17
<212> TYPE: PRT
<213> ORGANISM: Mus musculus

<400> SEQUENCE: 17

Leu Glu Trp Tyr Leu Gln Lys Pro Gly Gln Ser Pro Lys Leu Leu Ile
1               5                   10                  15

Tyr

<210> SEQ ID NO 18
<211> LENGTH: 36
<212> TYPE: PRT
<213> ORGANISM: Mus musculus

<400> SEQUENCE: 18

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30
```

-continued

```
Val Tyr Tyr Cys
        35

<210> SEQ ID NO 19
<211> LENGTH: 19
<212> TYPE: PRT
<213> ORGANISM: Mus musculus

<400> SEQUENCE: 19

Phe Gly Ser Gly Thr Lys Leu Glu Ile Lys Arg Ala Asp Ala Ala Pro
1               5                   10                  15

Thr Val Ser
```